(12) United States Patent
Hirai et al.

(10) Patent No.: US 9,029,528 B2
(45) Date of Patent: *May 12, 2015

(54) SOLUTION-BASED METHOD OF MAKING OLIGONUCLEOTIDES VIA PHOSPHORAMIDITE COUPLING

(75) Inventors: Kunihiro Hirai, Kanagawa (JP); Satoshi Katayama, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 274 days.

This patent is subject to a terminal disclaimer.

(21) Appl. No.: 13/473,884

(22) Filed: May 17, 2012

(65) Prior Publication Data

US 2012/0296074 A1 Nov. 22, 2012

Related U.S. Application Data

(60) Provisional application No. 61/486,949, filed on May 17, 2011.

(30) Foreign Application Priority Data

May 17, 2011 (JP) ................. 2011/110872

(51) Int. Cl.
*C07H 21/00* (2006.01)
*C07C 41/16* (2006.01)
(52) U.S. Cl.
CPC .............. *C07H 21/00* (2013.01); *C07C 41/16* (2013.01)
(58) Field of Classification Search
CPC ......... C07H 21/00; C07C 41/16; C07C 43/23
See application file for complete search history.

(56) References Cited

U.S. PATENT DOCUMENTS 5,510,476 A 4/1996 Ravikumar et al.
5,714,597 A 2/1998 Ravikumar et al.

FOREIGN PATENT DOCUMENTS

| CN | 101370817 | 2/2009 |
|---|---|---|
| CN | 101679474 | 3/2010 |
| CN | 101684136 | 3/2010 |
| EP | 2816053 | 12/2014 |
| JP | 2010-275254 | 12/2010 |
| JP | 2011-225598 | 11/2011 |
| WO | 96/03417 | 2/1996 |
| WO | 99/62922 | 12/1999 |
| WO | 2005/085272 A1 | 9/2005 |

OTHER PUBLICATIONS

International Search Report issued in PCT/JP2012/062708 on Aug. 14, 2012.

Written Opinion issued in PCT/JP2012/062708 on Jul. 30, 2012.
Ravikumar V. T., et al. Tetrahedron Letters, vol. 36, No. 37 pp. 6587-6590 (1995).
S. L. Beaucage et al., In Current Protocols in Nucleic Acid Chemisitry, M. Egli, et al., Eds., John Wiley & Sons, 3.0.1-3 and 3.1.1-28 (2011).
G. M. Bonora et al., Nucleic Acids Research, vol. 18, No. 11, pp. 3155-3159 (1990).
G. M. Bonora et al., Nucleic Acids Research, vol. 21, No. 5, pp. 1213-1217 (1993).
G. M. Bonora et al., Bioconjugate Chemistry, vol. 8, No. 6, pp. 793-797 (1997).
C. B. Reese et al., Tetrahedron Letters, vol. 27, No. 20, pp. 2291-2294 (1986).
C. B. Reese et al., Tetrahedron Letters, vol. 45, pp. 2567-2570 (2004).
Chinese Office Action dated Dec. 31, 2014, in CN 201280020029.5 filed May 17, 2012.
Partial European Search Report dated Mar. 3, 2015, in EP 12785878. 5, filed May 17, 2012.

*Primary Examiner* — Lawrence E Crane
(74) *Attorney, Agent, or Firm* — Oblon, McClelland, Maier & Neustadt, L.L.P.

(57) ABSTRACT

A method of producing an n+p-mer oligonucleotide efficiently in a high yield, which includes use of, as a starting material, an n-mer oligonucleotide wherein the 3'-terminal hydroxyl group is protected, and the 5'-terminal hydroxyl group is protected by a temporary protecting group, and continuously performing, in a solution, (1) a deprotection step of the 5'-terminal hydroxyl group, (2) a 5'-terminal elongation step by the addition of a p-mer oligonucleotide wherein the 3'-position is phosphoramidited, and (3) an oxidation step or a sulfurization step of a phosphite triester moiety. The 3'-hydroxyl group of the n-mer oligonucleotide is protected by a solubilizing protecting group represented by formula: -L-Y—Z, where L is a group represented by formula (a1):

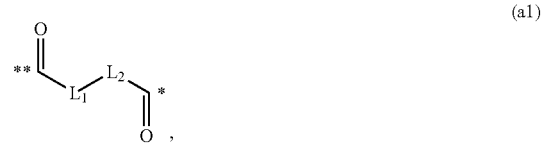

(a1)

Y is an oxygen atom, or NR wherein R is a hydrogen atom, an alkyl group or an aralkyl group, and Z is a group represented by formula (a2):

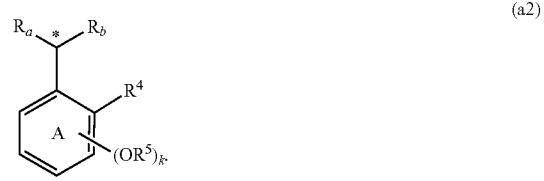

(a2)

33 Claims, No Drawings

SOLUTION-BASED METHOD OF MAKING OLIGONUCLEOTIDES VIA PHOSPHORAMIDITE COUPLING

CROSS-REFERENCES TO RELATED APPLICATIONS

The present application claims the benefits of priority to U.S. Provisional Application No. 61/486,949, filed May 17, 2011, and to Japanese Application No. 2011-110872, filed May 17, 2011.

TECHNICAL FIELD OF THE INVENTION

The present invention relates to a production method of a particular oligonucleotide. Moreover, the present invention relates to a particular pseudo solid phase protecting group, and a particular nucleoside.

BACKGROUND OF THE INVENTION

The synthesis method of oligonucleotide includes a phosphate triester method, an H-phosphonate method, a phosphoramidite method and the like, and solid phase synthesis (solid phase method) using a phosphoramidite method is most widely used at present (non-patent document 1). The solid phase method is advantageous from the aspect of speed, since process has been optimized and automation has progressed. However, it is associated with defects in that scaling-up is limited due to facility restriction, reagents and starting materials are used in excess, and confirmation of the progress status of the reaction in an intermediate step, analysis of intermediate structure and the like are difficult.

On the other hand, synthesis methods of oligonucleotide by a liquid phase method have also been studied. However, since the operation is complicated and the yield is low, a large-scale, rapid synthesis of long oligonucleotide is difficult.

In recent years, in an attempt to solve the respective defects of the liquid phase method and the solid phase method, an oligonucleotide production method using monomethoxy-polyethylene glycol (MPEG) as a protecting group is disclosed (non-patent documents 2 to 4). However, while synthetic examples of up to 20 mer DNA are disclosed, a crystallization isolation operation is essential for each reaction, and the progress status of the reaction and the like are difficult to confirm, since MPEG molecule itself is not a unimolecule.

In the meantime, a synthesis method of oligonucleotide comprising use of a hydrophobic group-linked nucleoside is disclosed (patent document 1). While it has been reported that the method affords synthesis of 21 mer oligonucleotide, the number of steps is markedly high and they are complicated, since a crystallization isolation operation is repeated in every step of deprotection of 5'-protecting group, coupling and oxidation.

DOCUMENT LIST

Patent Document patent document 1: JP-A-2010-275254

Non-Patent Documents non-patent document 1: S. L. Beaucage, D. E. Bergstorm, G. D. Glick, R. A. Jones, Current Protocols in Nucleic Acid Chemistry; John Wiley & Sons (2000)

non-patent document 2: Nucleic Acid Res., 1990, Vol. 18, No. 11, 3155-3159 non-patent document 3: Nucleic Acid Res., 1993, Vol. 21, No. 5, 1213-1217 non-patent document 4: Bioconjugate Chem., 1997, Vol. 8, No. 6, 793-797

SUMMARY OF THE INVENTION

Problems to be Solved by the Invention

The present inventors have conducted intensive studies in view of the aforementioned problems and found that, particularly, in the synthesis method of oligonucleotide as described in patent document 1, which uses a hydrophobic group-linked nucleoside, methanol used as a scavenger of a free protecting group (i.e., cation) in the deprotection step becomes an inhibitory substance for the coupling reaction in the next step, and therefore, needs to be completely removed and, for this object, a complicated operation such as a crystallization isolation step, an azeotropic distillation removal step and the like is essential.

In addition, it was clarified that when a cation scavenger other than methanol exemplified in patent document 1 is used, a side reaction such as re-protection of 5'-hydroxyl group and the like occurs in the neutralization step of an acid used as a deprotecting agent, and that the acid needs to be removed by crystallization isolation rather than neutralization.

Accordingly, the problem of the present invention is to provide an industrially advantageous production method without multistep procedures including a crystallization isolation step, which is an essential step in a synthesis method of oligonucleotide using a hydrophobic group-linked nucleoside.

More specifically, it is provision of a method of producing an n+p-mer oligonucleotide (n and p are each independently an integer of 1 or more) efficiently in a high yield which comprises use of, as a starting material, an n-mer oligonucleotide wherein the 3'-terminal hydroxyl group is protected by a pseudo solid phase protecting group, and the 5'-terminal hydroxyl group is protected by a temporary protecting group, and performing (1) a deprotection step of the 5'-terminal hydroxyl group protected by a temporary protecting group, (2) a 5'-terminal elongation step by the addition of a p-mer oligonucleotide wherein the 3'-position is phosphoramidited, and (3) an oxidation step or a sulfurization step of a phosphite triester moiety, wherein each step does not include crystallization and isolation, and is continuously performed in a solution.

Means of Solving the Problems

As a result of the intensive studies, the present inventors have found that the above-mentioned problems can be solved by adding a particular cation scavenger during or after deprotection of a 5'-terminal hydroxyl group protected by a temporary protecting group, applying a neutralization treatment with an organic base after completion of the deprotection reaction, and applying an oxidation treatment or sulfurization treatment using an oxidizing agent or sulfurizing agent.

The present invention includes the following.

[1] A method of producing an oligonucleotide comprising the following steps (1) to (4):
(1) a step of reacting, in a non-polar solvent,
(a) an n-mer oligonucleotide, wherein n is an integer of one or more, wherein the 3'-hydroxyl group is protected by a pseudo solid phase protecting group, and the 5'-hydroxyl group is protected by a temporary protecting group removable under acidic conditions, (b) an acid, and (c) at least one kind of cation scavenger selected from a pyrrole derivative and an indole derivative, to remove said temporary protecting group of said 5'-hydroxyl group, to obtain a reaction mixture;

(2) a step of neutralizing said reaction mixture with an organic base, to obtain a neutralized reaction mixture comprising an n-mer oligonucleotide in which the temporary protecting group at the 5'-hydroxyl group has been removed;

(3) a step of adding to said neutralized reaction mixture a p-mer oligonucleotide, wherein p is an integer of one or more, wherein the 3'-hydroxyl group is phosphoramidited, and the 5'-hydroxyl group is protected by a temporary protecting group removable under acidic conditions, to effect condensation with said n-mer oligonucleotide in which the temporary protecting group of the 5'-hydroxyl group has been removed, by forming a phosphite triester bond via the 5'-hydroxyl group thereof, to obtain a reaction mixture containing a n+p-mer oligonucleotide; and (4) a step of adding an oxidizing agent or a sulfurizing agent to said reaction mixture containing a n+p-mer oligonucleotide to convert the phosphite triester bond of said n+p-mer oligonucleotide, to a phosphate triester bond or a thiophosphate triester bond.

[2] The method of the above-mentioned [1], wherein p is 1.

[3] The method of the above-mentioned [1] or [2], further comprising the following steps (5) and (6):

(5) a step of adding a polar solvent to the reaction mixture containing a n+p-mer oligonucleotide, to precipitate said n+p-mer oligonucleotide; and (6) a step of obtaining said n+p-mer oligonucleotide by solid-liquid separation.

[4] The method of the above-mentioned [3], further comprising the following step (7):

(7) a step of removing all the protecting groups of said n+p-mer oligonucleotide.

[5] The method of any one of the above-mentioned [1] to [4], wherein the temporary protecting group removable under acidic conditions is a dimethoxytrityl group or a monomethoxytrityl group.

[6] The method of any one of the above-mentioned [1] to [5], wherein the non-polar solvent is a solvent selected from the group consisting of a halogenated solvent, an aromatic solvent, an ester solvent, an aliphatic solvent, a non-polar ether solvent, and a combination thereof.

[7] The method of any one of the above-mentioned [1] to [5], wherein the non-polar solvent is a solvent selected from the group consisting of dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and a combination thereof.

[8] The method of any one of the above-mentioned [3] to [7], wherein the polar solvent is an alcohol solvent or a nitrile solvent.

[9] The method of any one of the above-mentioned [3] to [7], wherein the polar solvent is methanol or acetonitrile.

[10] The method of any one of the above-mentioned [1] to [9], wherein the pyrrole derivative or the indole derivative is at least one kind selected from the group consisting of pyrrole, 3-methylpyrrole, 2,4-dimethylpyrrole, indole, 4-methylindole, 5-methylindole, 6-methylindole, 7-methylindole, 5,6-dimethylindole and 6,7-dimethylindole.

[11] The method of any one of the above-mentioned [1] to [10], wherein the oxidizing agent is iodine, (1S)-(+)-(10-camphorsulfonyl)oxaziridine, tert-butyl hydroperoxide, 2-butanone peroxide, 1,1-dihydroperoxycyclododecane, bis(trimethylsilyl)peroxide or m-chloroperbenzoic acid.

[12] The method of any one of the above-mentioned [1] to [10], wherein the sulfurizing agent is 3-((N,N-dimethylaminomethylidene)amino)-3H-1,2,4-dithiazole-5-thione, 3H-1,2-benzodithiol-3-one-1,1-dioxide, 3H-1,2-benzodithiol-3-one, phenylacetyl disulfide, tetraethylthiuram disulfide, 3-amino-1,2,4-dithiazole-5-thione or sulfur.

[13] The method of any one of the above-mentioned [1] to [12], wherein the acid is trifluoroacetic acid, dichloroacetic acid, trifluoromethanesulfonic acid, trichloroacetic acid, methanesulfonic acid, hydrochloric acid, acetic acid or p-toluenesulfonic acid.

[14] The method of any one of the above-mentioned [1] to [13], wherein the organic base is at least one kind selected from the group consisting of pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole.

[15] A method of producing an oligonucleotide by a continuous phosphoramidite method, comprising conducting at least one deprotection step in the presence of at least one cation scavenger selected from a pyrrole derivative and an indole derivative.

[16] A pseudo solid phase protecting group represented by the formula (I):

wherein

L is a group represented by the formula (a1):

wherein * shows the bonding position to Y;

** indicates the bonding position to a group to be protected;

$L_1$ is an optionally substituted divalent $C_{1-22}$ hydrocarbon group; and $L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom or NR wherein R is a hydrogen atom, an alkyl group or an aralkyl group, and Z is a group represented by the formula (a2):

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

$R^5$ in the number of k are each independently an organic group having an aliphatic hydrocarbon group having 10 or more carbon atoms;

k is an integer of 1 to 4;

ring A optionally further has, in addition to $OR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by the formula (a3):

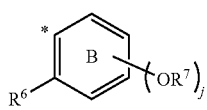

(a3)

wherein * shows a bonding position;

j is an integer of 0 to 4;

$R^7$ in the number of j are each independently an organic group having an aliphatic hydrocarbon group having 10 or more carbon atoms;

$R^6$ is a hydrogen atom, or optionally a single bond or —O— in combination with $R^4$ to form a fluorenyl group or a xanthenyl group together with ring A; and ring B optionally further has, in addition to $OR^7$ in the number of j, substituent(s) selected from the group consisting of a halogen atom, a $C_{1-4}$ alkyl group optionally substituted by a halogen atom, and a $C_{1-6}$ alkoxy group optionally substituted by a halogen atom.

[17] A nucleotide represented by the formula (II):

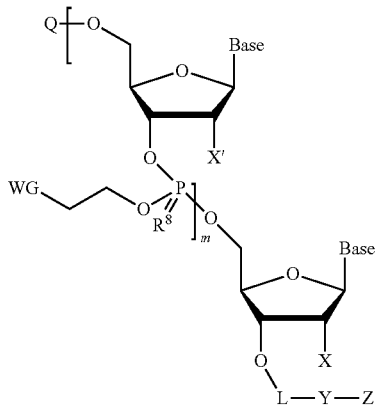

(II)

wherein m is an integer of 0 or more,

Base in the number of m+1 are each independently an optionally protected nucleic acid base, Q is a hydrogen atom, or a temporary protecting group removable under acidic conditions, X is a hydrogen atom, a halogen atom, or an optionally protected hydroxyl group, X' in the number of m are each independently a hydrogen atom, a halogen atom, or an optionally protected hydroxyl group, $R^8$ in the number of m are each independently an oxygen atom or a sulfur atom, WG in the number of m are each independently an electron-withdrawing group, L is a group represented by the formula (a1):

(a1)

wherein * shows the bonding position to Y;

** indicates the bonding position to a 3'-hydroxy group of the nucleotide;

$L_1$ is an optionally substituted divalent $C_{1-22}$ hydrocarbon group; and $L_2$ is a single bond, or a group represented by C(=O)C)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom, or NR wherein R is a hydrogen atom, an alkyl group or an aralkyl group, and Z is a group represented by the formula (a2):

(a2)

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

$R^5$ in the number of k are each independently is an organic group having an aliphatic hydrocarbon group having 10 or more carbon atoms;

k is an integer of 1 to 4;

ring A optionally further has, in addition to $OR^5$ in the number of k, substituent(s) selected from the group consisting of a halogen atom, a $C_{1-6}$ alkyl group optionally substituted by a halogen atom, and a $C_{1-6}$ alkoxy group optionally substituted by halogen atom;

$R_a$ is a hydrogen atom; and $R_b$ is a hydrogen atom, or a group represented by the formula (a3):

(a3)

wherein * shows a bonding position;

j is an integer of 0 to 4;

$R^7$ in the number of j are each independently is an organic group having an aliphatic hydrocarbon group having 10 or more carbon atoms;

$R^6$ is a hydrogen atom, or optionally a single bond or —O— in combination with $R^4$ to form a fluorenyl group or a xanthenyl group together with ring A; and ring B optionally further has, in addition to OR$^7$ in the number of j, substituent(s) selected from the group consisting of a halogen atom, a $C_{1-6}$ alkyl group optionally substituted by a halogen atom, and a $C_{1-6}$ alkoxy group optionally substituted by halogen atom.

[18] The nucleotide of the above-mentioned [17], wherein m is 0.

[19] The nucleotide of the above-mentioned [17] or [18], wherein
L in the formula (II) is a succinyl group, and
R$^5$ and/or R$^7$ are/is an alkyl group having 10 to 40 carbon atoms.

[20] The nucleotide of the above-mentioned [17] or [18], wherein
L in the formula (II) is a succinyl group, and
R$_a$ and R$_b$ are both hydrogen atoms, and
R$^5$ is an alkyl group having 10 to 40 carbon atoms.

[21] The nucleotide of the above-mentioned [17] or [18], wherein
L in the formula (II) is a succinyl group, and
R$^5$ and/or R$^7$ are/is an alkyl group having 12 to 30 carbon atoms.

[22] The nucleotide of the above-mentioned [17] or [18], wherein
L in the formula (II) is a succinyl group, and
Y—Z is a group selected from the group consisting of
a 3,4,5-tri(octadecyloxy)benzyloxy group,
a 3,5-di(docosyloxy)benzyloxy group,
a 3,5-di[3',4',5'-tri(octadecyloxy)benzyloxy]benzyloxy group,
a 3,4,5-tri[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-di[3',4',5'-tri(octadecyloxy)benzyloxy]benzylamino group, and
a 3,4,5-tri[3',4',5'-tri(octadecyloxy)benzyloxy]benzylamino group.

[23] The nucleotide of any one of the above-mentioned [17] to [22], wherein Q is a monomethoxytrityl group or a dimethoxytrityl group.

Effect of the Invention

A method of producing an n+p-mer oligonucleotide efficiently in a high yield can be provided, which includes use of an n-mer oligonucleotide, wherein the 3'-terminal hydroxyl group is protected by a pseudo solid phase protecting group, and the 5'-terminal hydroxyl group is protected by a temporary protecting group, as a starting material, and (1) a deprotection step of the 5'-terminal hydroxyl group protected by a temporary protecting group, (2) a 5'-terminal elongation step by the addition of a p-mer oligonucleotide wherein the 3'-position is phosphoramidited, and (3) an oxidation step or a sulfurization step of a phosphite triester moiety, by continuously performing the steps in this order in a solution, adding a particular cation scavenger during or after the deprotection of a 5'-terminal hydroxyl group protected by a temporary protecting group, applying a neutralization treatment after completion of the deprotection reaction, and using a particular oxidizing agent or sulfurizing agent in the oxidation step or sulfurization step.

DESCRIPTION OF EMBODIMENTS

The present invention provides a method of producing an n+p-mer oligonucleotide efficiently in a high yield, which includes use of, as a starting material, an n-mer oligonucleotide wherein the 3'-terminal hydroxyl group is protected by a pseudo solid phase protecting group, and the 5'-terminal hydroxyl group is protected by a temporary protecting group, and (1) a deprotection step of the 5'-terminal hydroxyl group protected by a temporary protecting group, (2) a 5'-terminal elongation step by the addition of a p-mer oligonucleotide wherein the 3'-position is phosphoramidited, and (3) an oxidation step or a sulfurization step of a phosphite triester moiety, by continuously performing the steps in this order in a solution, adding a particular cation scavenger during or after the deprotection of a 5'-terminal hydroxyl group protected by a temporary protecting group, applying a neutralization treatment after completion of the deprotection reaction, and using a particular oxidizing agent or sulfurizing agent in the oxidation step or sulfurization step.

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" to be the constituent unit of oligonucleotide means a compound wherein a nucleic acid base is bonded to the 1'-position of a sugar (e.g., ribose) by N-glycosidation.

In the present specification, the "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like. The "optionally protected nucleic acid base" means, for example, that an amino group may be protected in an adenyl group, a guanyl group or a cytosyl group, which is a nucleic acid base having an amino group, and a nucleic acid base wherein the amino group therein is protected by a protecting group sustainable under the deprotection conditions of the 5'-position is preferable. The "amino-protecting group" is not particularly limited, and examples thereof include the protecting groups described in PROTECTIVE GROUPS IN ORGANIC SYNTHESIS, 3rd edition, JOHN WILLY & SONS, 1999 and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the like. In some cases, the carbonyl-protecting group does not need to be particularly introduced. Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, monoalkylamino, dialkylamino, carboxy, cyano, nitro etc.) at any position(s), are also encompassed in the "nucleic acid base".

In the present specification, the "halogen atom" means a fluorine atom, a chlorine atom, a bromine atom or iodine atom.

In the present specification, examples of the "alkyl (group)" include a linear or branched chain alkyl group having one or more carbon atoms. When the carbon number is not particularly limited, it is preferably a $C_{1-10}$ alkyl group, more preferably a $C_{1-6}$ alkyl group. When the carbon number is not particularly limited, for example, methyl, ethyl, propyl, isopropyl, butyl, isobutyl, sec-butyl, tert-butyl, pentyl, hexyl and the like are preferable, and methyl and ethyl are particularly preferable.

In the present specification, the "aralkyl (group)" means a $C_{7-20}$ aralkyl group, preferably a $C_{7-16}$ aralkyl group (a $C_{6-10}$ aryl-$C_{1-6}$ alkyl group). Preferable specific examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, examples of the "alkoxy (group)" include an alkoxy group having one or more carbon atoms. When the carbon number is not particularly limited, it is preferably a $C_{1-10}$ alkoxy group, more preferably a $C_{1-6}$ alkoxy group. When the carbon number is not particularly limited, methoxy, ethoxy, propoxy, isopropoxy, butoxy, isobutoxy, sec-butoxy, tert-butoxy, pentyloxy, hexyloxy and the like are preferable, and methoxy and ethoxy are particularly preferable.

In the present specification, examples of the "acyl (group)" include a linear or branched chain $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, examples of the "alkenyl (group)" include a linear or branched chain $C_{2-6}$ alkenyl group and the like. Preferable examples thereof include vinyl, 1-propenyl, allyl, isopropenyl, butenyl, isobutenyl and the like. Among them, a $C_2$-$C_4$ alkenyl group is preferable.

In the present specification, examples of the "alkynyl (group)" include a $C_{2-6}$ alkynyl group and the like. Preferable examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_3$-$C_6$ cycloalkyl group such as cyclopropyl, cyclobutyl, cyclopentyl, cyclohexyl and the like is preferable, and cyclohexyl is particularly preferable.

In the present specification, the "aryl (group)" means an aromatic monocyclic or polycyclic (fused) hydrocarbon group. Specific examples thereof include a $C_{6-14}$ aryl group such as phenyl, 1-naphthyl, 2-naphthyl, biphenylyl, 2-anthryl and the like, and the like. Among them, a $C_{6-10}$ aryl group is more preferably and phenyl is particularly preferable.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like. Specific examples thereof include a monovalent group such as an alkyl group, an alkenyl group, an alkynyl group, a cycloalkyl group, an aryl group, an aralkyl group and the like, and a divalent group derived therefrom.

In the present specification, the "organic group having a hydrocarbon group" means a group having the aforementioned "hydrocarbon group", and the moiety other than the "hydrocarbon group" of the "organic group having a hydrocarbon group" can be determined freely. For example, the organic group optionally has, as a linker, a moiety such as —O—, —S—, —COO—, —OCONH—, —CONH— and the like.

[Pseudo Solid Phase Protecting Group]

The pseudo solid phase protecting group used in the present invention is not particularly limited as long as it is a protecting group simultaneously satisfying the reactivity and easiness of work-up, by binding to a reactive substrate to solubilize same in a non-polar solvent, thus enabling reaction in the liquid phase, and forming precipitation upon addition of a polar solvent to enable solid-liquid separation, and stable under acidic conditions capable of removing the 5'-terminal hydroxyl-protecting group. While examples of the pseudo solid phase protecting group include a group disclosed in non-patent documents 2 to 4, patent document 1 and the like, particularly, a pseudo solid phase protecting group represented by the following formula (I) is preferable, since a high yield can be achieved in the objective production method of oligonucleotide.

A group represented by the formula (I):

wherein

L is a group (linker) represented by the formula (a1):

wherein * shows the bonding position to Y;
** indicates the bonding position to a group to be protected;

$L_1$ is an optionally substituted divalent $C_{1-22}$ hydrocarbon group; and $L_2$ is a single bond, or a group (linker) represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is a single bond, an oxygen atom or NR wherein R is a hydrogen atom, an alkyl group or an aralkyl group, and Z is a group represented by the formula (a2):

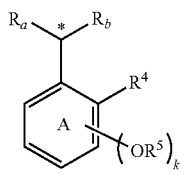

(a2)

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

$R^5$ in the number of k are each independently an organic group having an aliphatic hydrocarbon group having 10 or more carbon atoms;

k is an integer of 1 to 4;

ring A optionally further has, in addition to $OR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by the formula (a3):

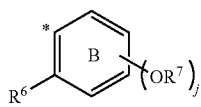

(a3)

wherein * shows a bonding position;

j is an integer of 0 to 4;

$R^7$ in the number of j are each independently an organic group having an aliphatic hydrocarbon group having 10 or more carbon atoms;

$R^6$ is a hydrogen atom, or optionally a single bond or —O— in combination with $R^4$ to form a fluorenyl group or a xanthenyl group together with ring A; and ring B optionally further has, in addition to $OR^7$ in the number of j, substituent(s) selected from the group consisting of a halogen atom, a $C_{1-6}$ alkyl group optionally substituted by a halogen atom, and a alkoxy group optionally substituted by a halogen atom, or a group represented by the formula (a2'):

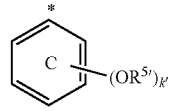

(a2')

wherein * shows a bonding position;

$R^{5'}$ in the number of k' are each independently is an organic group having an aliphatic hydrocarbon group having 10 or more carbon atoms;

k' is an integer of 1 to 4; and ring C optionally further has, in addition to $OR^{5'}$ in the number of k', substituent(s) selected from the group consisting of a halogen atom, a $C_{1-6}$ alkyl group optionally substituted by a halogen atom, and a $C_{1-6}$ alkoxy group optionally substituted by a halogen atom.

Examples of a group to be protected by the pseudo solid phase protecting group represented by the formula (I) include a hydroxy group, an amino group and the like, particularly a 3'-hydroxy group of a nucleoside or a nucleotide is preferable.

Preferable embodiment of the linker L represented by the above-mentioned formula (a1) is a group wherein, in the formula (a1), $L_1$ is an ethylene group or $CH_2$—O-1,4-phenylene-O—$CH_2$; and $L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-6}$ alkylene group, and $R^2$ and $R^3$ are each independently a hydrogen atom or an optionally substituted $C_{1-6}$ alkyl group, or $R^2$ and $R^3$ are optionally joined to form an optionally substituted $C_{1-6}$ alkylene bond.

Another preferable embodiment of the linker L represented by the above-mentioned formula (a1) is a group wherein, in the formula (a1), $L_1$ is an ethylene group; and $L_2$ is a single bond.

Another preferable embodiment of the linker L represented by the above-mentioned formula (a1) is a group wherein, in the formula (a1), $L_1$ is an ethylene group; and the moiety N($R^2$)—$R^1$—N($R^3$) of $L_2$ is a piperazinylene group.

Another preferable embodiment of the linker L represented by the above-mentioned formula (a1) is a group wherein, in the formula (a1), $L_1$ is an ethylene group; and $L_2$ is a group represented by C(=O)N($R^2$)—$R^1$—N($R^3$)* wherein  shows the bonding position to $L_1$, * shows the bonding position to C=O, $R^1$ is a pentylene group or a hexylene group, and $R^2$ and $R^3$ are each independently hydrogen atom or a methyl group.

A particularly preferable example of the above-mentioned linker L is a succinyl group since it is economical and easily available.

Preferable embodiment of Y is an oxygen atom, or NR wherein R is a hydrogen atom, an alkyl group or an aralkyl group.

R is preferably a hydrogen atom, a $C_{1-6}$ alkyl group or a $C_{7-16}$ aralkyl group, more preferably a hydrogen atom, methyl, ethyl or benzyl, particularly preferably a hydrogen atom.

Preferable embodiment of Z is a group represented by the formula (a2).

Preferable embodiment of Z represented by the above-mentioned formula (a2) is a group wherein, in the formula (a2), $R_a$ and $R_b$ are both hydrogen atoms;
$R^4$ is a hydrogen atom,
$R^5$ in the number of k are each independently is an organic group having an aliphatic hydrocarbon group having 10 or more carbon atoms (e.g., $C_{10-40}$ alkyl group); and
k is an integer of 1 to 3.

Another preferable embodiment of Z represented by the above-mentioned formula (a2) is a group wherein, in the formula (a2),
k is an integer of 1 to 3;
$R_a$ and $R_b$ are both hydrogen atoms;
$R^4$ is a hydrogen atom;
$R^5$ in the number of k are each independently benzyl group having 1 to 3 aliphatic hydrocarbon groups having 10 or more carbon atoms, or a cyclohexyl group having 1 to 3 aliphatic hydrocarbon groups having 10 or more carbon atoms; and ring A optionally further has, in addition to $OR^5$ in the number of k, substituent(s) selected from the group consisting of a halogen atom, a $C_{1-6}$ alkyl group optionally substituted by a halogen atom, and a $C_{1-6}$ alkoxy group optionally substituted by a halogen atom.

Another preferable embodiment of Z represented by the above-mentioned formula (a2) is a group wherein, in the formula (a2),
$R_a$ is a hydrogen atom; and
$R_b$ is a group represented by the above-mentioned formula (a3) wherein * shows a bonding position; j is an integer of 0 to 3; $R^7$ in the number of j are each independently a $C_{10-40}$ alkyl group; and $R^4$ and $R^6$ are both hydrogen atoms.

Another preferable embodiment of Z represented by the above-mentioned formula (a2) is a group wherein, in the formula (a2),
$R_a$ is a hydrogen atom;
$R_b$ is a group represented by the above-mentioned formula (a3) wherein * shows a bonding position; j is an integer of 0 to 3;
$R^7$ in the number of j are each independently a $C_{10-40}$ alkyl group;
$R^6$ is joined with $R^4$ of ring A to form a single bond or —O—, and therefore, ring A and ring B form a fluorenyl group or a xanthenyl group in combination.

The pseudo solid phase protecting group represented by the above-mentioned formula (I) is preferably a group difficult to cleave under acidic conditions that permit removal of the protecting group of 5'-terminal hydroxyl and easy to cleave under basic conditions.

Representative examples of the pseudo solid phase protecting group include a group wherein, in the above-mentioned of the formula (I),
L is a group represented by the above-mentioned formula (a1) (preferably a succinyl group etc.), and
Y—Z is the following group:
a 3,4,5-tri(octadecyloxy)benzyloxy group,
a 3,5-di(docosyloxy)benzyloxy group,
a 3,5-di[3',4',5'-tri(octadecyloxy)benzyloxy]benzyloxy group,
a 3,4,5-tri[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-di[3',4',5'-tri(octadecyloxy)benzyloxy]benzylamino group, or
a 3,4,5-tri[3',4',5'-tri(octadecyloxy)benzyloxy]benzylamino group.

[Nucleotide Wherein the 3'-Hydroxyl Group is Protected by a Pseudo Solid Phase Protecting Group and the 5'-Hydroxyl Group is Protected by a Temporary Protecting Group]

The nucleotide suitable for pseudo solid phase synthesis can be produced by bonding a pseudo solid phase protecting group used in the present invention to a 3'-hydroxyl group of nucleotide.

A particularly preferable nucleotide to achieve a high yield in the objective production method of oligonucleotide is, for example, a compound represented by the following formula (II) (hereinafter sometimes to be referred to as the compound of the present invention).

The formula (II):

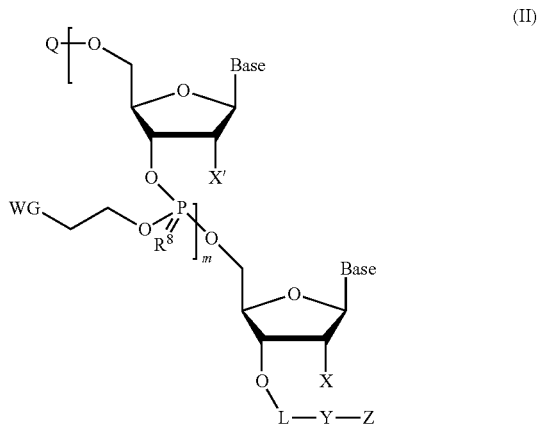

wherein
m is an integer of 0 or more,
Base in the number of m+1 are each independently an optionally protected nucleic acid base,
Q is a hydrogen atom or a temporary protecting group removable under acidic conditions,
X is a hydrogen atom, a halogen atom or an optionally protected hydroxyl group,
X' in the number of m are each independently a hydrogen atom, a halogen atom, or an optionally protected hydroxyl group,
$R^8$ in the number of m are each independently an oxygen atom or a sulfur atom,
WG in the number of m are each independently an electron-withdrawing group,
Y is a single bond, an oxygen atom or NR wherein R is a hydrogen atom, an alkyl group or an aralkyl group, and
L and Z are as defined above, except that ** for the formula (Ia) indicates the bonding position to a 3'-hydroxy group of the nucleoside.

Of the compounds of the present invention, a compound of the formula (II) wherein Y is an oxygen atom or NR wherein R is a hydrogen atom, an alkyl group or an aralkyl group is a novel compound.

In the compound of the present invention, p-mer oligonucleotide (p is an integer of one or more) wherein the 3'-hydroxyl group is phosphoramidited and the 5'-hydroxyl group is protected by a temporary protecting group is bonded via oxygen atom of 5'-hydroxyl group to form m+l+p-mer oligonucleotide (p is an integer of one or more).

When m is 0, the compound of the present invention is to be understood as "nucleoside", which is a starting compound of 3'-terminal in the oligonucleotide synthesis. In addition, the compound of the present invention also encompasses a compound wherein 5'-hydroxyl group is not protected (Q is a hydrogen atom) in a wide sense.

m is an integer of 0 or more, preferably 0. While the upper limit of m is not particularly limited, it is preferably 49 or less, more preferably 29 or less, and further preferably 19 or less.

Group X and X' in the number of m at the 2-position of ribose residue constituting nucleotide, which is the compound of the present invention, are each independently a hydrogen atom, a halogen atom or an optionally protected hydroxyl group.

As the halogen atom, a fluorine atom or a chlorine atom is preferable, and a fluorine atom is more preferable.

While the protecting group of the "optionally protected hydroxyl group" is not particularly limited, for example, any protecting group described in PROTECTIVE GROUPS IN ORGANIC SYNTHESIS, 3rd ed., JOHN WILLY & SONS (1999) and the like can be mentioned. Specifically, methyl group, benzyl group, p-methoxybenzyl group, tert-butyl group, methoxymethyl group, methoxyethyl group, 2-tetrahydropyranyl group, ethoxyethyl group, cyanoethyl group, cyanoethoxymethyl group, phenylcarbamoyl group, 1,1-dioxothiomorpholine-4-thiocarbamoyl group, acetyl group, pivaloyl group, benzoyl group, trimethylsilyl group, triethylsilyl group, triisopropylsilyl group, tert-butyldimethylsilyl group, [(triisopropylsilyl)oxy]methyl(Tom) group, 1-(4-chlorophenyl)-4-ethoxypiperidin-4-yl(Cpep) group and the like can be mentioned. Among these, triethylsilyl group, triisopropylsilyl group and tert-butyldimethylsilyl group are preferable. From the aspects of economic efficiency and easy availability, tert-butyldimethylsilyl group is particularly preferable.

Temporary protecting group Q that can be used as 5'-hydroxyl-protecting group of the compound of the present invention is not particularly limited as long as it can be deprotected under acidic conditions and can be used as a hydroxyl-protecting group and, for example, trityl group, 9-(9-phenyl) xanthenyl group, 9-phenylthioxanthenyl group, $di(C_{1-6}$ alkoxy)trityl groups such as 1,1-bis(4-methoxyphenyl)-1-phenylmethyl group (dimethoxytrityl group) and the like, mono($C_{1-18}$ alkoxy)trityl groups such as 1-(4-methoxyphenyl)-1,1-diphenylmethyl group (monomethoxytrityl group) and the like can be mentioned. Among these, monomethoxytrityl group and dimethoxytrityl group are preferable, and dimethoxytrityl group is more preferable, from the aspects of easy deprotection and easy availability.

$R^8$ in the number of m are each independently an oxygen atom or a sulfur atom, preferably an oxygen atom.

WG in the number of m are each independently an electron-withdrawing group. Examples of the electron-withdrawing group include a cyano group, a nitro group and the like, preferably a cyano group.

The "organic group having an aliphatic hydrocarbon group having 10 or more carbon atoms" for $R^5$ or $R^7$ in the present specification is a monovalent organic group having an aliphatic hydrocarbon group having a carbon number of 10 or more in the molecule structure thereof.

The "aliphatic hydrocarbon group" of the "aliphatic organic group having a hydrocarbon group" is a straight chain or branched saturated or unsaturated aliphatic hydrocarbon group, and an aliphatic hydrocarbon group having a carbon number of 10 or more is preferable, an aliphatic hydrocarbon group having a carbon number of 10 to 40 is more preferable, and an aliphatic hydrocarbon group having a carbon number of 12 to 30 is particularly preferable.

The position of the "aliphatic hydrocarbon group" of the "aliphatic organic group having a hydrocarbon group" is not particularly limited, and may be present on the terminal (monovalent group) or a position other than the terminal (for example, divalent group).

As the "aliphatic hydrocarbon group", a monovalent group such as a linear or branched chain alkyl group having a carbon number of not less than 10, a linear or branched chain alkenyl group and the like, and a divalent group induced therefrom can be mentioned. Of these, an alkyl group having a carbon number of 10 to 40 is preferable, and an alkyl group having a carbon number of 12 to 30 is particularly preferable. Specific examples of the "aliphatic hydrocarbon group" include monovalent groups such as decyl group, dodecyl group, tridecyl group, myristyl group, cetyl group, stearyl group, oleyl group, linoleyl group, arachyl group, behenyl group, isostearyl group and the like and divalent groups induced therefrom.

The moiety other than the "aliphatic hydrocarbon group" of the "aliphatic organic group having a hydrocarbon group" can be optionally determined. For example, as a linker, a moiety such as —O—, —S—, —COO—, —OCONH— and —CONH—, as well as a hydrocarbon group (monovalent group or divalent group) and the like may be present. Examples of the "hydrocarbon group" include an aliphatic hydrocarbon group, an aromatic-aliphatic hydrocarbon group, a monocyclic saturated hydrocarbon group, an aromatic hydrocarbon group and the like, and specific examples thereof include monovalent groups such as an alkyl group, an alkenyl group, an alkynyl group, a cycloalkyl group, an aryl group, an aralkyl group and the like and a divalent group induced therefrom. As "alkyl group", "alkenyl group", "alkynyl group", "cycloalkyl group", "aryl group", or "aralkyl group" as the moiety other than "aliphatic hydrocarbon group", those similar to the aforementioned groups can be mentioned.

The "hydrocarbon group" is optionally substituted by a substituent selected from a halogen atom (chlorine atom, bromine atom, fluorine atom, iodine atom), a $C_{1-6}$ alkyl group optionally substituted by one or more halogen atoms, an oxo group and the like.

In the present specification, R constituting Y in the formula (II) is a hydrogen atom, an alkyl group or an aralkyl group, preferably a hydrogen atom, a $C_{1-6}$ alkyl group or a $C_{7-16}$ aralkyl group, more preferably a hydrogen atom, methyl, ethyl or benzyl, and particularly preferably a hydrogen atom.

The "aliphatic organic group having a hydrocarbon group" for "$R^5$(group)" and/or "$R^7$(group)" constituting Z in the above-mentioned formula (II) may contain plural "aliphatic hydrocarbon groups" due to a branch and the like. When plural "aliphatic hydrocarbon groups" are present in the "aliphatic organic group having a hydrocarbon group", they may be the same or different.

The lower limit of the total carbon number of the "aliphatic organic group having a hydrocarbon group" for "$R^5$(group)" and/or "$R^7$(group)" constituting Z in the above-mentioned formula (II) is preferably 10 or more, more preferably 12 or more, further preferably 14 or more, still more preferably 18 or more, and particularly preferably 30 or more. On the other hand, the upper limit of the total carbon number of the "aliphatic organic group having a hydrocarbon group" for "$R^5$ (group)" and/or "$R^7$(group)" is preferably 200 or less, more preferably 150 or less, further preferably 120 or less, still more preferably 100 or less, especially preferably 80 or less, and particularly preferably 60 or less. When the carbon number is higher, the crystallinity of the compound of the present invention in a polar solvent is fine even when oligonucleotide has a long chain.

A preferable embodiment of Y—Z in the formula (II) is the same as the preferable embodiment of Y—Z in the aforementioned formula (I).

A preferable embodiment of the compound represented by the formula (II) of the present invention is a compound of the formula (II), wherein m is 0,
Base is a cytosyl group, a uracil group, a thyminyl group, an adenyl group, or a guanyl group, each of which is optionally protected;
Q is a di($C_{1-6}$alkoxy)trityl group, or a mono($C_{1-6}$ alkoxy)trityl group;
X is a hydrogen atom, a halogen atom, or an optionally protected hydroxyl group; and
L-Y—Z is the combination of each group shown as a preferable embodiment in the aforementioned formula (I).

Another preferable embodiment of the compound represented by the formula (II) of the present invention is a compound of the formula (II), wherein m is 0,
Base is a cytosyl group, a uracil group, a thyminyl group, an adenyl group, or a guanyl group, each of which is optionally protected;
Q is a dimethoxytrityl group or a monomethoxytrityl group;
X is a hydrogen atom, a halogen atom, or an optionally protected hydroxyl group; and
L-Y—Z is the combination of each group shown as a preferable embodiment in the aforementioned formula (I).

A still another preferable embodiment of the compound represented by the formula (II) of the present invention is a compound of the formula (II), wherein m is 0,
Base is a cytosyl group, a uracil group, a thyminyl group, an adenyl group, or a guanyl group, each of which is optionally protected;
Q is a dimethoxytrityl group;
X is a hydrogen atom, a fluorine atom, a methoxy group, an acetoxy group, or a tert-butyldimethylsilyloxy group; and
L-Y—Z is the combination of each group shown as a preferable embodiment in the aforementioned formula (I). compound.

[Production Method of Precursor (Z—Y—H) (Alcohol or Amine) of Pseudo Solid Phase Protecting Group]

While the production method of a precursor of the aforementioned pseudo solid phase protecting group is not particularly limited, it can be produced from a starting material compound according to a method known per se (e.g., Bull. Chem. Soc. Jpn. 2001, 74, 733-738, JP-A-2000-44493, WO2006/104166, WO2007/034812, WO2007/122847, WO2010/113939 etc.) or a method analogous thereto.

A compound to be used as a starting material compound, for example, a halide corresponding to $R^5$ and $R^7$ constituting Z in the formula (II) and the like is a commercially available product, or can be produced according to a method known per se or a method analogous thereto.

While the production method of the compound represented by the formula (II) of the present invention wherein m is 0, hereinafter referred to as "the formula (IIa)", is not particularly limited, it can be produced from the above-mentioned precursor of a pseudo solid phase protecting group by a method known per se (Richard T. Pon et al., Nucleic Acids Research 2004, 32, 623-631) or a method analogous thereto.

The precursor (Z—Y—H) of the pseudo solid phase protecting group can be produced by a method known per se or a method analogous thereto, as mentioned above. When a starting material compound has a substituent (e.g., hydroxyl group, amino group, carboxy group) that influences the reaction, the starting material compound is generally protected in advance by a suitable protecting group according to a known method and then subjected to the reaction. Such protecting group can be removed after the reaction by a known method such as an acid treatment, an alkali treatment, a catalytic reduction and the like.

A general production method of a compound of the above-mentioned formula (IIa) wherein L is a succinyl group is shown below.

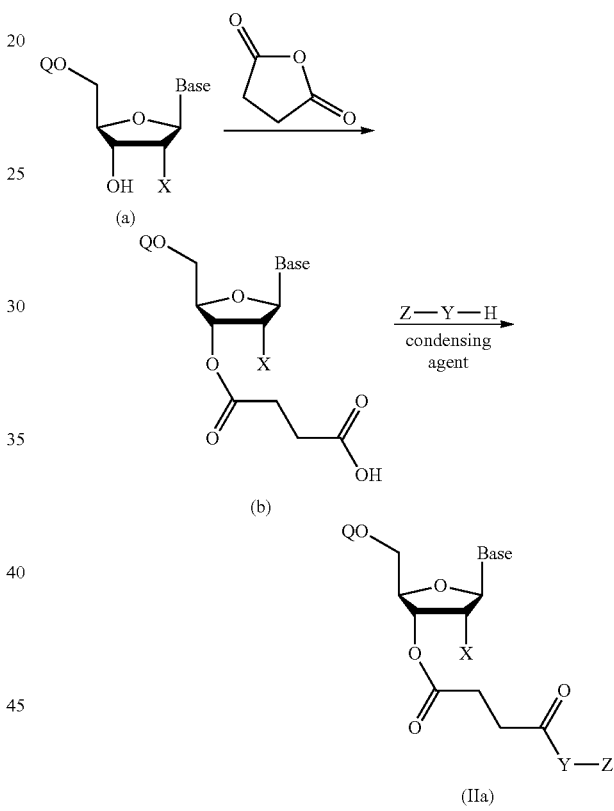

wherein each symbol is as defined above.

Nucleoside (a) wherein 5'-hydroxyl group is protected by protecting group Q is reacted with succinic anhydride in the presence of a base to give compound (b) wherein succinic acid is introduced into 3'-hydroxyl group. A compound represented by the formula (IIa) can be obtained by dehydration condensation of compound (b) with Z—Y—H in the presence of a condensing agent.

The conversion step of the above-mentioned nucleoside (a) to compound (b) is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, aliphatic hydrocarbon solvents such as pentane, hexane, heptane, octane and the like, ether solvents such as diethylether, tetrahydrofuran, cyclopentyl methyl ether and the like, and mixed solvents thereof are preferable. Of these, dichloromethane and chloroform are particularly preferable.

While the base is not particularly limited, for example, an organic base mentioned below can be used, with preference given to triethylamine.

The above-mentioned dehydrating condensation step is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, or aliphatic hydrocarbon solvents such as pentane, hexane, heptane, octane and the like, and mixed solvents thereof are preferable. Of these, dichloromethane and chloroform are particularly preferable.

Examples of the condensing agent used for the condensation reaction of compound (b) with Z—Y—H include dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy) tripyrrolidinophosphonium hexafluorophosphate (PyBop), 0-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like. Of these, HBTU, HCTU, N-ethyl-N'-3-dimethylaminopropylcarbodiimide and hydrochloride thereof (EDC HCl) are preferable.

The amount of the condensing agent to be used is 1 to 10 mol, preferably 1 to 5 mol, per 1 mol of compound (b). The amount of Z—Y—H to be used is 1 to 10 mol, preferably 1 to 5 mol, per 1 mol of compound (b). While the reaction temperature is not particularly limited as long as the reaction proceeds, it is preferably −10° C. to 50° C., more preferably 0° C. to 30° C. The reaction time is 30 min to 70 hr.

A compound of the above-mentioned formula (IIa) wherein L is other than a succinyl group can also be produced by performing a reaction similar to the above-mentioned production method except that a corresponding acid anhydride, a corresponding dicarboxylic acid halide, an activated ester of corresponding dicarboxylic acid and the like is used instead of succinic anhydride.

A compound of the formula (II) wherein m is an integer of one or more can be produced by repeating the 5'-terminal elongation process according to the below-mentioned production method of the present invention using the compound of the formula (IIa) as a starting material.

[Production Method of the Present Invention]

The production method of oligonucleotide of the present invention (hereinafter to be also referred to as the "production method of the present invention") is explained. Specifically, a production method from appropriately protected n-mer oligonucleotide to appropriately protected n+p-mer oligonucleotide is explained. For example, when n=1, n-mer oligonucleotide is to be understood as "nucleoside", and when p=1, p-mer oligonucleotide is to be understood as "nucleoside" and n+p-mer oligonucleotide is to be understood as "dinucleotide".

The present invention is a production method of oligonucleotide, containing the following steps (1) to (4).

(1) a step of reacting, in a non-polar solvent,
(a) an n-mer oligonucleotide, wherein n is an integer of one or more, wherein the 3'-hydroxyl group is protected by a pseudo solid phase protecting group, and the 5'-hydroxyl group is protected by a temporary protecting group removable under acidic conditions,
(b) an acid, and
(c) at least one kind of cation scavenger selected from a pyrrole derivative and an indole derivative,
to remove said temporary protecting group of said 5'-hydroxyl group, to obtain a reaction mixture;

(2) a step of neutralizing said reaction mixture with an organic base, to obtain a neutralized reaction mixture comprising an n-mer oligonucleotide in which the temporary protecting group at the 5'-hydroxyl group has been removed;

(3) a step of adding to said neutralized reaction mixture a p-mer oligonucleotide, wherein p is an integer of one or more, wherein the 3'-hydroxyl group is phosphoramidited, and the 5'-hydroxyl group is protected by a temporary protecting group removable under acidic conditions,
to effect condensation with said n-mer oligonucleotide in which the temporary protecting group of the 5'-hydroxyl group has been removed, by forming a phosphite triester bond via the 5'-hydroxyl group thereof, to obtain a reaction mixture containing a n+p-mer oligonucleotide; and (4) a step of adding an oxidizing agent or a sulfurizing agent to said reaction mixture containing a n+p-mer oligonucleotide to convert the phosphite triester bond of said n+p-mer oligonucleotide, to a phosphate triester bond or a thiophosphate triester bond.

While the upper limit of n is not particularly limited, it is preferably 50 or less, more preferably 30 or less, and further preferably 20 or less.

While the upper limit of p is not particularly limited, it is preferably 50 or less, more preferably 30 or less, further preferably 20 or less, still more preferably 5 or less, and particularly preferably 3 or less.

Furthermore, by including the following steps (5) and (6), n+p-mer oligonucleotide can be purified conveniently and effectively by removing excess starting materials and by-products:

(5) a step of adding a polar solvent to the reaction mixture containing a n+p-mer oligonucleotide, to precipitate said n+p-mer oligonucleotide; and (6) a step of obtaining said n+p-mer oligonucleotide by solid-liquid separation.

The steps (5) and (6) of the present invention are unique to a pseudo solid phase protecting group and is absent in liquid phase methods and solid phase methods.

When the amount of the by-product generated can be controlled by the management of equivalent of the starting materials and controlling the reaction, it is preferable to repeat step (1) to step (4) as a basic unit, which includes steps (5) and (6).

Since the generation of by-product can be strictly managed and controlled and highly pure oligonucleotide can be obtained, it is preferable to repeat step (1) to step (6) as a basic unit.

Oligonucleotide can be isolated and produced by further including step (7) in the production method of the present invention:

(7) a step of removing all the protecting groups of said n+p-mer oligonucleotide.

Each step is explained in detail in the following.

Step (1) (Deprotection Step) and Step (2) (Neutralizing Step)

In this step, in a non-polar solvent, temporary protecting group Q (Q is as defined above) of the 5'-terminal hydroxyl group of an n-mer oligonucleotide (i), wherein m is any integer of 0 or more, and when m=0, it is nucleoside, wherein the 3'-hydroxyl group is protected by a pseudo solid phase protecting group, and the 5'-hydroxyl group is protected by a temporary protecting group removable under acidic conditions is removed by adding an acid, and the mixture is neutralized by adding an organic base (deprotection step).

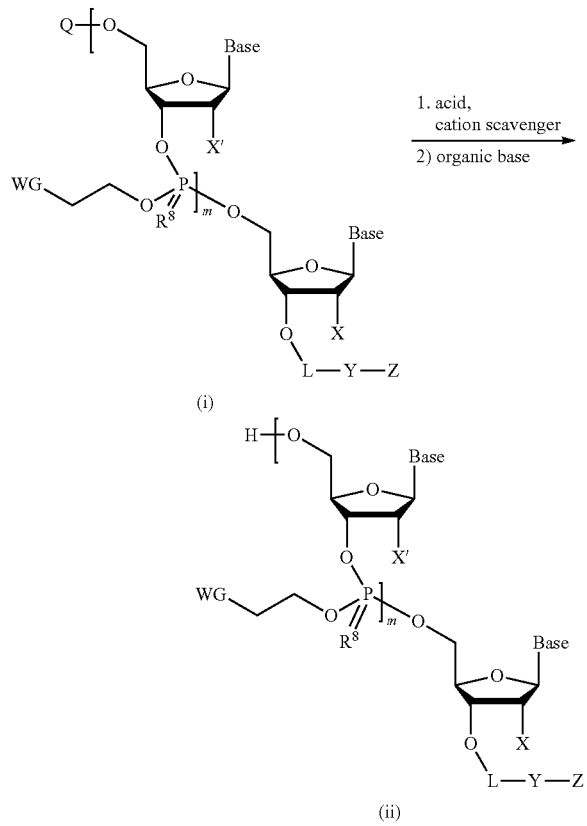

wherein $R^8$ in the number of m is an oxygen atom or a sulfur atom, WG in the number of m is an electron-withdrawing group (e.g., cyano group), X' in the number of m is each independently as defined for X, and other symbols are as defined above.

This step is performed in a solvent that does not influence the reaction. Since a higher solubility of the solvent is expected to afford superior reactivity, a non-polar solvent showing high solubility of the compound of the present invention is preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Two or more kinds of these solvents may be used in a mixture in an appropriate ratio. In addition, the above-mentioned non-polar solvent may be mixed with a polar solvent at an appropriate ratio, such as nitrile solvents such as acetonitrile, propionitrile and the like, amide solvents such as N,N-dimethylformamide, N,N-dimethylacetamide, N-methylpiperidone and the like, as long as n-mer oligonucleotide is dissolved. Among them, dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, combinations thereof and the like are preferable, and chloroform, dichloromethane and toluene are particularly preferable.

In this step, the concentration of n-mer oligonucleotide (i) in a solvent is not particularly limited as long as the oligonucleotide is dissolved, it is preferably 1 to 30 wt %.

To continuously perform the deprotection step, subsequent condensation step, and oxidation step in a solution, it is essential to use a cation scavenger in this step during or after the removal reaction of a temporary protecting group Q of 5'-hydroxyl group in n-mer oligonucleotide (i).

While the cation scavenger is not particularly limited as long as re-protection (returning to starting material) with the removed protecting group Q and side reaction with the deprotected functional group do not proceed, pyrrole derivatives such as pyrrole, 2-methylpyrrole, 3-methylpyrrole, 2,3-dimethylpyrrole, 2,4-dimethylpyrrole and the like; and indole derivatives such as indole, 4-methylindole, 5-methylindole, 6-methylindole, 7-methylindole, 5,6-dimethylindole, 6,7-dimethylindole and the like can be used. Since a good cation trap effect can be obtained, pyrrole, 3-methylpyrrole, 2,4-dimethylpyrrole, indole, 4-methylindole, 5-methylindole, 6-methylindole, 7-methylindole, 5,6-dimethylindole and 6,7-dimethylindole are preferable, pyrrole, 3-methylpyrrole and indole are more preferable, pyrrole and indole are more preferable, and pyrrole is particularly preferable.

The amount of cation scavenger to be used in this step is 1 to 50 mol, preferably 5 to 20 mol, per 1 mol of n-mer oligonucleotide (i).

While the acid to be used in this step is not particularly limited as long as good deprotection can be achieved, trifluoroacetic acid, dichloroacetic acid, trifluoromethanesulfonic acid, trichloroacetic acid, methanesulfonic acid, hydrochloric acid, acetic acid, p-toluenesulfonic acid and the like are preferably used. Since good reaction can be achieved, trifluoroacetic acid, dichloroacetic acid, trifluoromethanesulfonic acid and trichloroacetic acid are more preferable, trifluoroacetic acid, dichloroacetic acid and trifluoromethanesulfonic acid are more preferable, trifluoroacetic acid and trifluoromethanesulfonic acid are still more preferable, and trifluoroacetic acid is particularly preferable. These acids may be diluted with the above-mentioned non-polar solvent. When the aforementioned acid is used, it may be combined with a particular base to appropriately adjust the acidity before use.

The amount of the acid to be used in this step is 1 to 100 mol, preferably 1 to 40 mol, per 1 mol of n-mer oligonucleotide (i).

While the reaction temperature in this step is not particularly limited as long as the reaction proceeds, it is preferably −10° C. to 50° C., more preferably 0° C. to 40° C. While the reaction time varies depending on the kind of n-mer oligonucleotide to be used, the kind of acid, the kind of solvent, the reaction temperature and the like, it is 5 min to 5 hr.

When an acid used as a deprotecting agent is present in the condensation step of the next step, deprotection of protecting group Q of p-mer oligonucleotide (iii) wherein the 5'-hydroxyl group is protected by temporary protecting group Q, and the 3'-hydroxyl group is phosphoramidited is induced. Therefore, the acid needs to be removed or neutralized. Since condensation step is continuously performed in the reaction mixture in the present invention, neutralization by an organic base is performed.

The organic base to be used for neutralization is not particularly limited as long as it can neutralize the above-mentioned acids, and the obtained salt can function as a condensing agent. Since the reaction proceeds smoothly, pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole are preferable, pyridine, 2,4,6-trimethylpyridine, benzimidazole, 1,2,4-triazole, N-phenylimidazole, N-methylimidazole, 2-amino-4,6-dimethylpyrimidine and 1,10-phenanthroline are more preferable, pyridine, 2,4,6-trimethylpyridine, benzimidazole, triazole and N-phenylimidazole are further preferable, pyridine, 2,4,6-trimethylpyridine, benzimidazole and 1,2,4-triazole are still more preferable, and pyridine, 2,4,6-trimethylpyridine and benzimidazole are particularly preferable.

The amount of the organic base to be used in this step is 1 to 10 mol, preferably 1 to 3 mol, per 1 mol of acid.

A particularly preferable combination of acid and organic base in this step is trifluoroacetic acid and pyridine, trifluoroacetic acid and 2,4,6-trimethylpyridine or trifluoromethanesulfonic acid and benzimidazole.

Step (3) (Condensation Step)

In this step, n-mer oligonucleotide (ii) wherein the 5'-hydroxyl group is deprotected, which is obtained in the aforementioned steps (1) and (2), and p-mer oligonucleotide (iii) (q is any integer of 0 or more, when q=0, it is nucleoside) wherein the 5'-hydroxyl group is protected by temporary protecting group Q, and the 3'-hydroxyl group is phosphoramidited are condensed.

As the p-mer oligonucleotide (iii) wherein the 5'-hydroxyl group is protected by temporary protecting group Q, the 3'-hydroxyl group is phosphoramidited, the compound wherein p is 1 (i.e., nucleoside wherein the 5'-hydroxyl group is protected by temporary protecting group Q, and the 3'-hydroxyl group is phosphoramidited) is preferable.

While the upper limit of q is not particularly limited, it is preferably 49 or less, more preferably 29 or less, further preferably 19 or less, still more preferably 4 or less, and particularly preferably 2 or less.

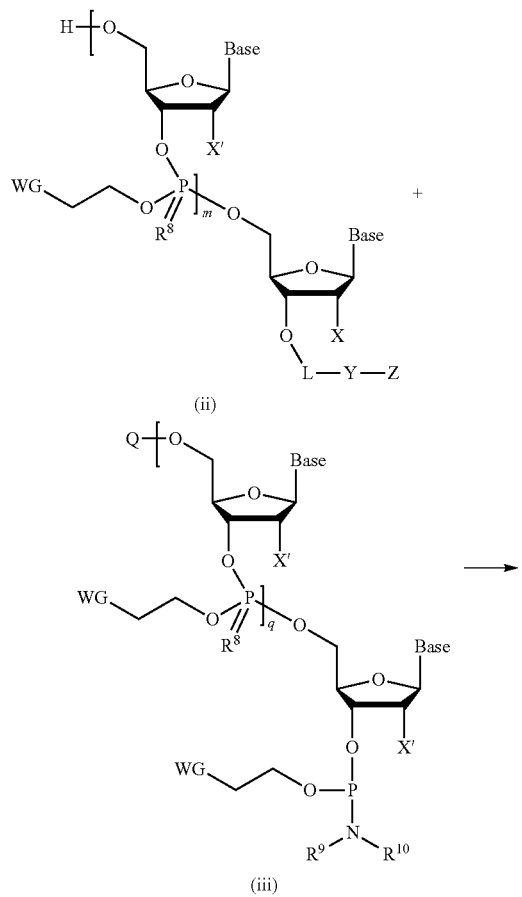

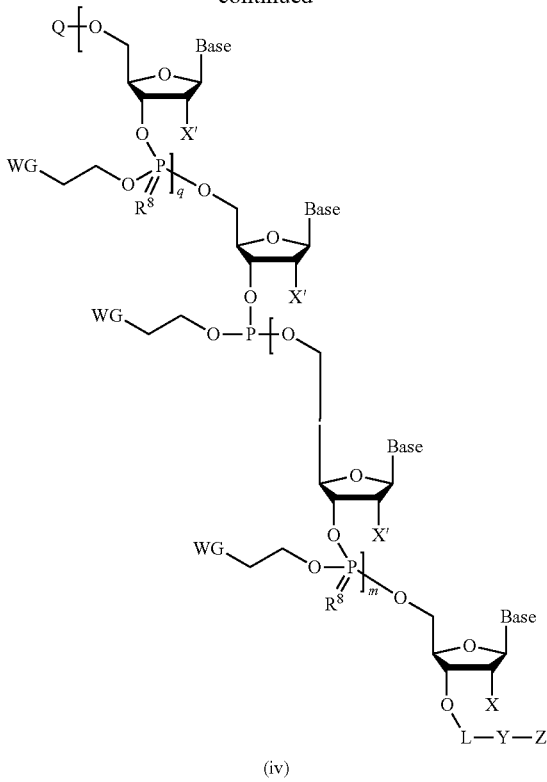

wherein X' is as defined for X, $R^9$ and $R^{10}$ are each independently an alkyl group, or a 5- or 6-membered saturated cyclic amino group formed together with the adjacent nitrogen atom. The saturated cyclic amino group optionally has one oxygen atom or sulfur atom as a ring-constituting atom besides nitrogen atom. Other symbols are as defined above.

This step can be simply performed by directly adding p-mer oligonucleotide (iii) wherein the 5'-hydroxyl group is protected by temporary protecting group Q, and the 3'-hydroxyl group is phosphoramidited to the reaction mixture after steps (1) and (2) without isolation of n-mer oligonucleotide (ii) wherein 5'-hydroxyl group is deprotected, which is obtained in the aforementioned step (2). In this condensation step, the salt (e.g., pyridine trifluoroacetate), which is formed by the acid added during deprotection step (1) and the organic base added during neutralization reaction, acts as a condensing agent. Therefore, steps (1) to (3) continuously performed in a solution provide advantages of not only omission of an isolation operation but also improved reaction efficiency. When the condensation reaction proceeds slowly, the reaction efficiency can also be further improved by additionally adding a separate condensing agent (e.g., pyridine trifluoroacetate, tetrazole, 5-benzylthio-1H-tetrazole, 4,5-dicyanoimidazole etc.).

In this step, moreover, when the acidity of the reaction mixture becomes high, a side reaction removing temporary protecting group Q may occur. Therefore, N-methylimidazole is preferably added to suppress acidification of the reaction mixture.

The amount of N-methylimidazole to be added to adjust the acidity is 0.1 to 1 mol, preferably 0.5 mol, per 1 mol of organic base.

The p-mer oligonucleotide (iii) wherein the 5'-hydroxyl group is protected by temporary protecting group Q, and the 3'-hydroxyl group is phosphoramidited to be used in this step is, for example, p-mer oligonucleotide wherein a group represented by the following formula:

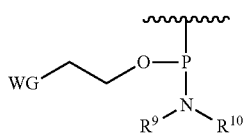

wherein each symbol is as defined above, is bonded. As the nucleic acid base of the p-mer oligonucleotide, the groups as defined above can be mentioned.

The p-mer oligonucleotide (iii) wherein the 5'-hydroxyl group is protected by temporary protecting group Q, and the 3'-hydroxyl group is phosphoramidited to be used in this step can be produced by a known method (M. H. Caruthers et al., Method in Enzymology 1987, 154, 287-313; S. L. Beaucage and M. H. Caruthers, Tetrahedron Letters 1981, 22, 1859-1862), including reacting p-mer oligonucleotide wherein the 5'-hydroxyl group is protected by temporary protecting group Q, and the 3'-hydroxyl group is not protected with a phosphoramiditing reagent represented by the following formulas (c) or (d);

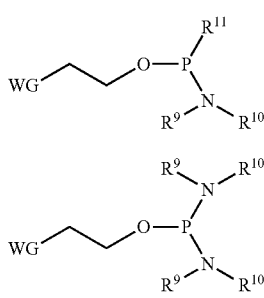

In the formula (c), (d), $R^{11}$ is a halogen atom, and other symbols are as defined above.

This step is performed in a solvent that does not influence the reaction. Specifically, a non-polar solvent similar to the one used in the aforementioned step (1) can be mentioned. The above-mentioned non-polar solvent may be mixed with nitrile solvents such as acetonitrile, propionitrile and the like; ketone solvents such as acetone, 2-butanone and the like; amide solvents such as N,N-dimethylformamide, N,N-dimethylacetamide, N-methylpyrrolidone and the like; polar ether solvents such as 1,4-dioxane, tetrahydrofuran and the like; sulfoxide solvents such as dimethylsulfoxide and the like at an appropriate ratio, as long as n-mer oligonucleotide (ii) wherein the temporary protecting group of 5'-hydroxyl group is removed can be dissolved.

In this case, as the polar solvent, amide solvent, nitrile solvent, and a combination thereof are preferable, acetonitrile, N,N-dimethylformamide, N-methylpiperidone, and a combination thereof are more preferable, and acetonitrile is particularly preferable.

A polar solvent may be added as a solution of p-mer oligonucleotide (iii) wherein the 5'-hydroxyl group is protected by temporary protecting group Q, and the 3'-hydroxyl group is phosphoramidited, a condensing agent and the like.

The amount of p-mer oligonucleotide (iii) wherein the 5'-hydroxyl group is protected by temporary protecting group Q, and the 3'-hydroxyl group is phosphoramidited to be used is 1 to 10 mol, preferably 1 to 5 mol, per 1 mol of the n-mer oligonucleotide (ii) obtained in step (1), wherein the temporary protecting group of 5'-hydroxyl group is removed.

While the reaction temperature is not particularly limited as long as the reaction proceeds, 0° C. to 100° C. is preferable, and 20° C. to 50° C. is more preferable. While the reaction time varies depending on the kind of n-mer oligonucleotide to be condensed, the reaction temperature and the like, it is 5 min to 24 hr.

Step (4) (Oxidation Step or Sulfurization Step)

The n+p-mer oligonucleotide (iv) obtained in step (3) is reacted with an oxidizing agent or sulfurizing agent to convert the phosphite triester bond in the n+p-mer oligonucleotide (iv) to a phosphate triester bond or a thiophosphate triester bond.

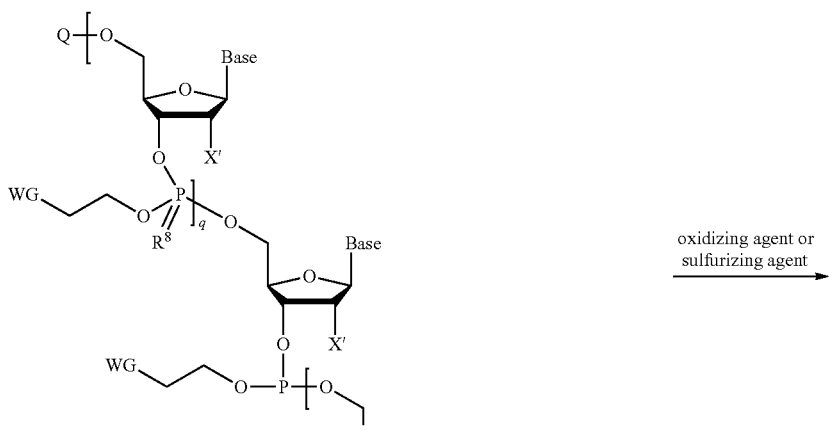

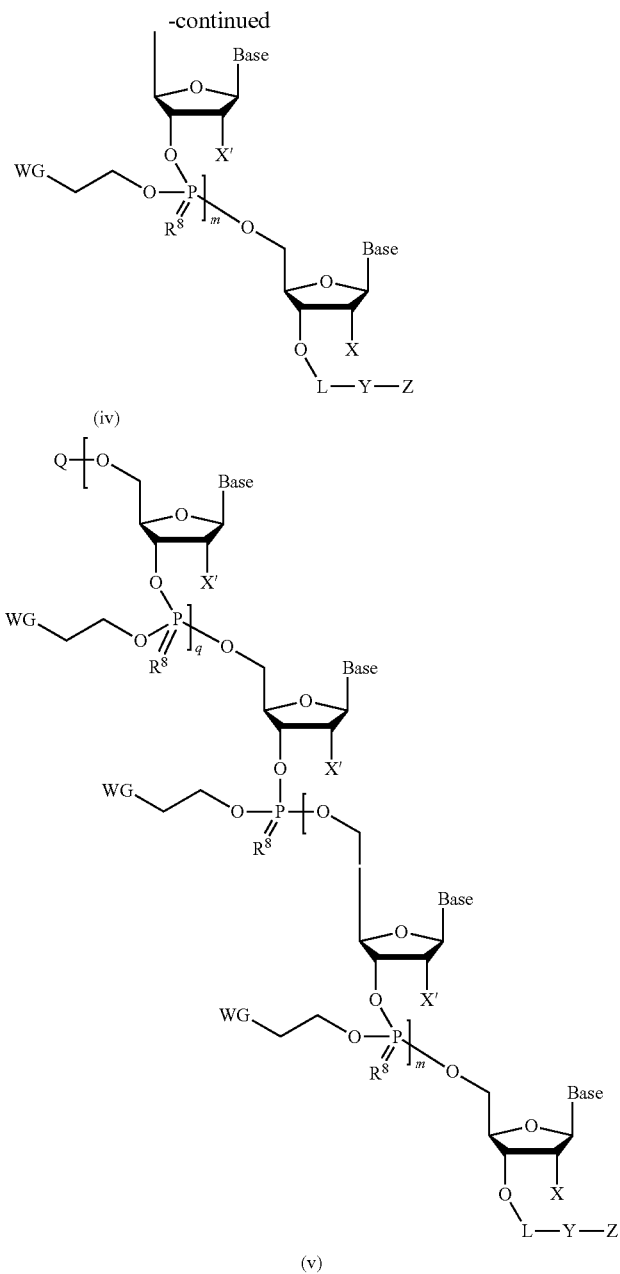

(v)

wherein each symbol is as defined above.

This step can be simply performed by directly adding an oxidizing agent or sulfurizing agent to the reaction mixture after step (3), without isolating the n+p-mer oligonucleotide (iv) obtained in step (3).

While the "oxidizing agent" to be used in this step is not particularly limited as long as it can oxidize a phosphite triester bond into a phosphate triester bond without oxidizing other moieties, iodine, (1S)-(+)-(10-camphorsulfonyl)oxaziridine, tert-butyl hydroperoxide (TBHP), 2-butanone peroxide, 1,1-dihydroperoxycyclododecane, bis(trimethylsilyl) peroxide or m-chloroperbenzoic acid is preferably used. Since good oxidation reaction can be achieved, iodine, (1S)-(+)-(10-camphorsulfonyl)oxaziridine, tert-butyl hydroperoxide, 2-butanone peroxide and 1,1-dihydroperoxycyclododecane are more preferable, iodine, (1S)-(+)-(10-camphorsulfonyl)oxaziridine, tert-butyl hydroperoxide and 2-butanone peroxide are more preferable, iodine and tert-butyl hydroperoxide are still more preferable, and iodine is particularly preferable. The oxidizing agent can be used after diluting with a suitable solvent to achieve a concentration of 0.05 to 2M. While the dilution solvent is not particularly limited as long as it is inert to the reaction, pyridine, THF, dichloromethane, water and a mixed solvent of any of them can be mentioned. Among them, for example, iodine/water/pyridine-THF or iodine/pyridine-acetic acid, peroxide (TBHP)/dichloromethane or tert-butyl hydroperoxide/nonane is preferably used.

The "sulfurizing agent" to be used in this step is not particularly limited as long as it can convert a phosphite triester bond to a thiophosphate triester bond, 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), 3-amino-1,2,4-dithiazole-5-thione (ADTT) or sulfur is preferably used. Since a good reaction proceeds, 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one and phenylacetyl disulfide (PADS) are more preferable, 3-((N,N-dimethylaminomethylidene)amino)-3H-1,2,4-dithiazole-5-thione and 3H-1,2-benzodithiol-3-one-1,1-dioxide are further preferable, and 3-((N,N-dimethylaminomethylidene)amino)-3H-1,2,4-dithiazole-5-thione is particularly preferable. The sulfurizing agent can be used after diluting with a suitable solvent to achieve a concentration of 0.05 to 2M. While the dilution solvent is not particularly limited as long as it is inert to the reaction, for example, dichloromethane, acetonitrile, pyridine and a mixed solvent of any of them can be mentioned.

The amount of the oxidizing agent or sulfurizing agent to be used is 1 to 50 mol, preferably 1 to 5 mol, per 1 mol of the n+p-mer oligonucleotide (iv) obtained in step (3).

While the reaction temperature is not particularly limited as long as the reaction proceeds, 0° C. to 100° C. is preferable, and 20° C. to 50° C. is more preferable. While the reaction time varies depending on the kind of n+p-mer oligonucleotide (iv), the kind of oxidizing agent or sulfurizing agent to be used, the reaction temperature and the like, it is 1 min to 3 hr.

Steps (5) and (6) (Precipitation and Solid-Liquid Separation Steps)

In this step, a polar solvent is added to a reaction mixture containing n+p-mer oligonucleotide (v) having a phosphate triester bond or a thiophosphate triester bond, which is obtained in step (4), to allow precipitation of the n+p-mer oligonucleotide (v), and the precipitate is obtained by solid-liquid separation.

Examples of the polar solvent used to precipitate the object product n+p-mer oligonucleotide (v) in this step include alcohol solvents such as methanol, ethanol, isopropanol and the like; nitrile solvents such as acetonitrile, propionitrile and the like; ketone solvents such as acetone, 2-butanone and the like; polar ether solvents such as 1,4-dioxane, tetrahydrofuran and the like; amide solvents such as dimethylformamide, dimethylacetamide, N-methylpiperidone and the like, sulfoxide solvents such as dimethylsulfoxide and the like; water etc., and mixed solvent of two or more kinds thereof. Among them, alcohol solvents and nitrile solvents are preferably used, and methanol and acetonitrile are more preferably used. The polar solvent in the present invention is preferably methanol, particularly from the practical aspects.

The polar solvent may contain water to minimize the loss of the object product in a polar solvent. Particularly, when acetonitrile is used as a polar solvent, the object product tends to dissolve in the polar solvent to increase the loss. Using acetonitrile containing a small amount of water, the loss can be minimized.

In this case, the content of water in the polar solvent is preferably 1 to 10% (v/v), more preferably 3 to 8% (v/v). When the water content is too low, the loss of the object product in a polar solvent tends to increase, and when the water content is too high, removal of unnecessary substances such as excess monomer etc. into a polar solvent tends to be insufficient.

In precipitation where iodine is used as an oxidizing agent, the color development due to iodine can be removed by using a solution of methanol, which is a precipitation solvent, saturated with sodium thiosulfate (hypo), and therefore, n+p-mer oligonucleotide (v) wherein the 5'-hydroxyl group is protected can be isolated with high purity.

In precipitation where a sulfurizing agent is used, n+p-mer oligonucleotide (v) wherein the 5'-hydroxyl group is protected can be isolated with high purity by using a solution of methanol, which is a precipitation solvent, saturated with a reducing agent such as a trivalent phosphite reagent (e.g., trimethylphosphite, triethylphosphite, tris(2-carboxyethyl) phosphine etc.), hypo and the like.

The production method of oligonucleotide of the present invention can afford the object oligonucleotide with high purity and in a high yield by repeating the above-mentioned steps (1) to (6) a desired number of times.

Step (7) (Deprotection, Oligonucleotide Isolation Step)

In the production method of oligonucleotide of the present invention, deprotection is performed after step (6) according to the kind and properties of the protecting group, whereby oligonucleotide is isolated. All protecting groups can be removed from oligonucleotide according to the deprotection method described in PROTECTIVE GROUPS IN ORGANIC SYNTHESIS, 3rd ed., JOHN WILLY & SONS (1999) and the like. To be specific, the pseudo solid phase protecting group in the present invention, as well as the protecting group of nucleic acid base such as phenoxyacetyl group, acetyl group and the like, and cyanoethyl group and the like for protection of phosphate backbone can all be removed by a treatment with aqueous ammonia, aqueous ammonia/ethanol solution, or a mixture of aqueous ammonia and aqueous methylamine solution. In addition, nucleotide 5' hydroxyl-protecting group can be removed by a treatment with the acid used in step (1) or an appropriately diluted solution of such acid.

Since oligonucleotide without a protecting group is easily degraded by an enzyme, oligonucleotide is preferably isolated under appropriate air contamination control.

The progress of the reaction in each of the above-mentioned steps can be confirmed by a method similar to conventional liquid phase organic synthesis reaction. That is, the reaction can be traced by thin layer silica gel chromatography, high performance liquid chromatography and the like.

The oligonucleotide obtained by steps (5) and (6), or step (7) can also be led to a desired oligonucleotide derivative by further applying an organic synthesis reaction.

The oligonucleotide produced by the present invention can be used for various applications such as various human or veterinary pharmaceutical products (RNA, DNA, oligonucleic acid medicine, etc.), functional food, specified health food, food, chemical product, polymer material for human or industrial use, and the like.

EXAMPLES

The present invention is explained in more detail in the following by referring to Examples, which are not to be construed as limiting the scope of the present invention. The reagents, apparatuses and materials used in the present invention are commercially available unless otherwise specified. In the present specification, when indicated by abbreviation, each indication is based on the abbreviation of the IUPAC-IUB Commission on Biochemical Nomenclature or conventional abbreviations in the art.

Reference Example 1

Synthesis of 3,4,5-tris(octadecyloxy)benzyl amine

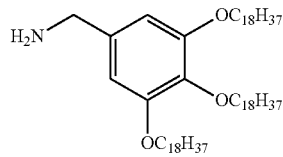

(1) Synthesis of 3,4,5-tris(octadecyloxy)benzyl chloride

Under an argon atmosphere, 3,4,5-tris(octadecyloxy)benzyl alcohol (10.0 g, 11.0 mmol) was dissolved in dichloromethane (100 mL), N,N-dimethylformamide (84.0 μL, 1.10 mmol) and thionyl chloride (1.20 ml, 16.4 mmol) were added, and the mixture was stirred at 30° C. for 90 min. After completion of the reaction, the reaction mixture was concentrated under reduced pressure, acetonitrile was added, and the precipitated solid was filtered. The obtained solid was dried under reduced pressure to give the title compound (10.0 g, 98.2%) as a white solid.

(2) Synthesis of 3,4,5-tris(octadecyloxy)benzyl azide 3,4,5-Tris(octadecyloxy)benzyl chloride (4.02 g, 4.31 mmol) was dissolved in a mixed solvent of chloroform (40 mL) and N,N-dimethylformamide (120 mL), sodium azide (418 mg, 6.42 mmol) was added, and the mixture was stirred at 80° C. for 3 hr. After completion of the reaction, the reaction mixture was cooled to room temperature and washed with purified water (150 mL). The organic layer was dried over sodium sulfate and filtered. The filtrate was concentrated under reduced pressure, methanol was added thereto, and the precipitated solid was collected by filtration. The obtained solid was dried under reduced pressure to give the title compound (3.92 g, 97.4%) as a white solid.

(3) Synthesis of 3,4,5-tris(octadecyloxy)benzyl amine

Under an argon atmosphere, 3,4,5-tris(octadecyloxy)benzyl azide (3.00 g, 3.21 mmol) was dissolved in dehydrating tetrahydrofuran (35 mL) and, under ice-cooling, lithium aluminum hydride (162 mg, 4.30 mmol) was added. The reaction mixture was stirred at room temperature for 2 hr. After completion of the reaction, purified water (2 mL) and 4.0 mol/L aqueous sodium hydroxide solution (2 mL) were added dropwise to the reaction mixture to decompose unreacted lithium aluminum hydride, and the reaction mixture was filtered through celite. The filtrate was concentrated under reduced pressure, acetonitrile was added, and the precipitated solid was collected by filtration and dried under reduced pressure to quantitatively give the title compound (3.09 g) as a white solid.

TLC: Rf=0.80 (dichloromethane:hexane=1:1)

$^1$H-NMR (400 MHz): δ 0.88 (t, 9H, J=7.0 Hz, H$_3$C, -octadecyloxy), 1.27-1.46 (m, 96H, —CH$_2$-octadecyloxy), 1.70-1.82 (m, 6H, —CH$_2$-octadecyloxy), 3.76 (s, 2H, H$_2$N—CH$_2$-benzyl), 3.92 (t, 2H, J=6.6 Hz, —O—CH$_2$-octadecyloxy), 3.97 (t, 4H, J=6.6 Hz, —O—CH$_2$-octadecyloxy), 6.50 (s, 2H, -benzyl)

Reference Example 2

Synthesis of 3,5-bis(docosyloxy)benzyl alcohol

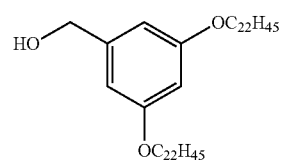

(1) Synthesis of methyl [3,5-bis(docosyloxy)]benzoate

Potassium carbonate (19.9 g, 144 mmol) was suspended in dehydrating N,N-dimethylformamide (200 mL), 1-bromodocosane (15.6 g, 46.7 mmol) and methyl (3,5-dihydroxy)benzoate (3.60 g, 21.4 mmol) were added, and the mixture was stirred at 90° C. overnight. After completion of the reaction, the reaction mixture was poured into purified water (800 mL), the mixture was stirred for 1 hr, and the precipitated solid was collected by filtration. The obtained solid was dissolved again in dichloromethane (800 mL), and the insoluble material was filtered off. The filtrate was concentrated under reduced pressure, and acetone was added again to precipitate a solid. The solid was collected by filtration and slurry-washed in methanol. After filtration, the obtained solid was dried under reduced pressure to give the title compound (13.9 g, 96.5%) as a white solid.

(2) Synthesis of 3,5-bis(docosyloxy)benzyl alcohol

Under an argon atmosphere, methyl [3,5-bis(docosyloxy)]benzoate (2.03 g, 2.59 mmol) was dissolved in dehydrating tetrahydrofuran (50 mL) and, under ice-cooling, lithium aluminum hydride (148 mg, 3.93 mmol) was added, and the mixture was stirred at 40° C. for 1 hr. Ethyl acetate was added dropwise to decompose unreacted lithium aluminum hydride. Diethyl ether was added, and the mixture was washed with aqueous hydrochloric acid. The organic layer was concentrated under reduced pressure, methanol was added to the concentrated solution, and the precipitated solid was collected by filtration. The obtained solid was dried under reduced pressure to give the title compound (1.73 g, 88.0%) as a white solid.

TLC: Rf=0.80 (ethyl acetate:hexane=1:4)

$^1$H-NMR (400 MHz): δ 0.88 (t, 6H, J=7.0 Hz, H$_3$C-docosyloxy), 1.25-1.80 (m, 84H, —CH$_2$-docosyloxy), 3.93 (t, 4H, J=6.6 Hz, —O—CH$_2$-docosyloxy), 4.62 (d, 2H, J=6.1 Hz, HO—CH$_2$-benzyl), 6.38 (s, 1H, -benzyl), 6.50 (s, 2H, -benzyl)

Reference Example 3

Synthesis of 3,5-bis(docosyloxy)benzyl amine

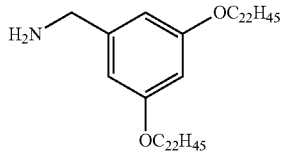

The title compound was synthesized from 3,5-bis(docosyloxy)benzyl alcohol according to the method of Reference Example 1.

TLC: Rf=0.50 (dichloromethane:hexane=1:4)

$^1$H-NMR (400 MHz): δ 0.88 (t, 6H, J=7.0 Hz, H$_3$C-docosyloxy), 1.25-1.79 (m, 84H, —CH$_2$-docosyloxy), 3.79 (s, 2H, H$_2$N—CH$_2$-benzyl), 3.93 (t, 4H, J=6.6 Hz, —O—CH$_2$-docosyloxy), 6.34 (s, 1H, -benzyl), 6.44 (s, 2H, -benzyl)

Reference Example 4

Synthesis of 2,4-bis(docosyloxy)benzyl alcohol

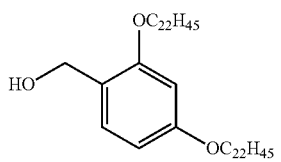

(1) Synthesis of 2,4-bis(docosyloxy)benzaldehyde

Under an argon atmosphere, 2,4-dihydroxybenzaldehyde (3.00 g, 21.7 mmol), potassium carbonate (30.0 g, 217 mmol) and 1-bromodocosane (17.3 g, 44.5 mmol) were added to dehydrating N,N-dimethylformamide (150 mL), and the mixture was stirred at 70° C. overnight. After completion of the reaction, the reaction mixture was poured into purified water (1 L), the mixture was stirred for 1 hr, and the precipitated solid was collected by filtration. The obtained solid was slurry-washed in methanol and filtered, and the obtained solid was dried under reduced pressure to give the title compound (16.3 g, 99.3%) as a white solid.

(2) Synthesis of 2,4-bis(docosyloxy)benzyl alcohol

Under an argon atmosphere, 2,4-bis(docosyloxy)benzaldehyde (2.99 g, 3.96 mmol) was dissolved in a mixed solvent of dehydrating tetrahydrofuran (60 mL) and methanol (6.0 mL), sodium borohydride (375 mg, 9.91 mmol) was added, and the mixture was stirred at 40° C. for 2 hr. After completion of the reaction, purified water (2.0 mL) was added dropwise to decompose unreacted sodium borohydride and the mixture was filtered through celite. The filtrate was concentrated under reduced pressure, methanol was added, and the precipitated solid was collected by filtration. The obtained solid was dried under reduced pressure to give the title compound (2.77 g, 92.9%) as a white solid.

TLC: Rf=0.80 (ethyl acetate:hexane=1:4)

$^1$H-NMR (400 MHz): δ 0.88 (t, 6H, J=7.0 Hz, H$_3$C-docosyloxy), 1.25-1.80 (m, 84H, —CH$_2$-docosyloxy), 2.23 (t, 1H, J=6.5 Hz, HO-benzyl), 3.94 (t, 2H, J=6.6 Hz, —O—CH$_2$-docosyloxy), 3.98 (t, 2H, J=6.6 Hz, —O—CH$_2$-docosyloxy), 4.61 (d, 2H, J=6.5 Hz, HO—CH$_2$-benzyl), 6.42 (d, 1H, J=8.2 Hz, -benzyl), 6.45 (s, 1H, -benzyl), 7.12 (d, 1H, J=8.2 Hz, -benzyl)

Reference Example 5

Synthesis of 2,4-bis(docosyloxy)benzyl amine

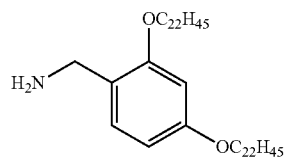

The title compound was synthesized from 2,4-bis(docosyloxy)benzyl alcohol according to the method of Reference Example 1.

TLC: Rf=0.40 (dichloromethane:methanol=9:1)

$^1$H-NMR (400 MHz): δ 0.88 (t, 6H, J=7.0 Hz, H$_3$C-docosyloxy), 1.25-1.81 (m, 84H, —CH$_2$-docosyloxy), 3.75 (s, 2H, H$_2$N—CH$_2$-benzyl), 3.91-3.97 (m, 4H, —O—CH$_2$-docosyloxy), 6.39 (d, 1H, -benzyl), 6.44 (s, 1H, -benzyl), 7.07 (d, 1H, J=8.2 Hz, -benzyl)

Reference Example 6

Synthesis of 2,3,4-tris(octadecyloxy)benzhydryl amine

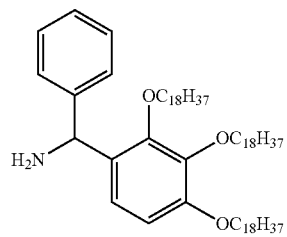

(1) Synthesis of 2,3,4-tris(octadecyloxy)benzophenone

Under an argon atmosphere, 2,3,4-trihydroxybenzophenone (1.61 g, 7.00 mmol), 1-bromooctadecane (7.32 g, 22.0 mmol) and potassium carbonate (4.35 g, 31.5 mmol) were added to dehydrating N,N-dimethylformamide (30 mL), and the mixture was stirred at 80° C. overnight. After completion of the reaction, purified water (200 mL) was added to the reaction mixture, the mixture was stirred for 1 hr, and the precipitated solid was collected by filtration. The obtained solid was slurry-washed in methanol and, after filtration, dried under reduced pressure to give the title compound (6.31 g, 91.1%) as a white solid.

(2) Synthesis of 2,3,4-tris(octadecyloxy)benzhydryl alcohol 2,3,4-Tris(octadecyloxy)benzophenone (3.00 g, 3.04 mmol) was dissolved in a mixed solvent of chloroform (30 mL) and methanol (10 mL), sodium borohydride (360 mg, 9.51 mmol) was added, and the mixture was stirred at 45° C. for 2 hr. After completion of the reaction, 0.1 mol/L aqueous hydrochloric acid was added dropwise to decompose unreacted sodium borohydride and the mixture was washed with 1.0 mol/L aqueous hydrochloric acid. The organic layer was dried over sodium sulfate and filtered, and the filtrate was concentrated under reduced pressure. Methanol was added to the concentrated solution, and the precipitated solid was collected by filtration and dried under reduced pressure to give the title compound (2.98 g, 99.0%) as a white solid.

(3) Synthesis of N-(9-fluorenylmethoxycarbonyl)-2,3,4-tris(octadecyloxy)benzhydryl amine Under an argon atmosphere, 2,3,4-tris(octadecyloxy)benzhydryl alcohol (2.44 g, 2.46 mmol) and 9-fluorenylmethylcarbamate (1.06 g, 4.41 mmol) were dissolved in dehydrating toluene (40 mL) at 50° C., methanesulfonic acid (51.4 μL, 740 mol) was added, and the mixture was stirred at 100° C. overnight. After completion of the reaction, the reaction mixture was concentrated under reduced pressure, methanol was added, and the precipitated solid was collected by filtration. The obtained solid was dried under reduced pressure to give the title compound (3.37 g, 98.1%) as a white solid.

(4) Synthesis of 2,3,4-tris(octadecyloxy)benzhydryl amine

N-(9-Fluorenylmethoxycarbonyl)-2,3,4-tris(octadecyloxy)benzhydryl amine (3.37 g, 2.89 mmol) was dissolved in a mixed solvent of chloroform (30 mL) and acetonitrile (15 mL), 20% piperidine [1-methyl-2-pyrrolidone solution] (28.6 mL, 57.9 mmol) was added, and the mixture was stirred at room temperature for 30 min. After completion of the reaction, the reaction mixture was concentrated under reduced pressure, methanol was added, and the precipitated solid was collected by filtration. The obtained solid was dried under reduced pressure to give the title compound (2.80 g, 97.9%) as a white solid.

TLC: Rf=0.60 (dichloromethane:methanol=9:1)

$^1$H-NMR (400 MHz): δ 0.88 (t, 9H, J=7.0 Hz, H$_3$C-octadecyloxy), 1.26-1.81 (m, 102H, —CH$_2$-octadecyloxy), 3.77-3.86 (m, 2H, —O—CH$_2$-octadecyloxy), 3.91-3.95 (m, 4H, —O—CH$_2$-octadecyloxy), 5.40 (s, 1H, H$_2$N—CH-benzhydryl), 6.58 (d, 1H, J=8.7 Hz, -benzhydryl), 6.88 (d, 1H, J=8.7 Hz, -benzhydryl), 7.20-7.37 (m, 5H, -benzhydryl)

Reference Example 7

Synthesis of 3,4,5-tris[3,4,5-tris(octadecyloxy)benzyloxy]benzyl alcohol

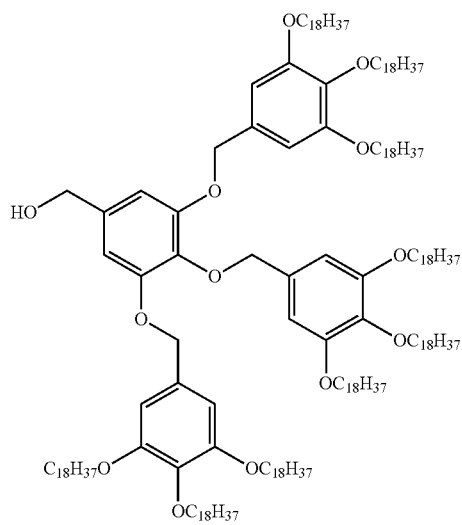

(1) Synthesis of methyl {3,4,5-tris[3,4,5-tris(octadecyloxy)benzyloxy]}benzoate

Under an argon atmosphere, methyl gallate (182 mg, 1.00 mmol), 3,4,5-tris(octadecyloxy)benzyl chloride (2.81 g, 3.01 mmol) and potassium carbonate (1.39 g, 10.1 mmol) were added to dehydrating N,N-dimethylformamide (20 mL), and the mixture was stirred at 70° C. overnight. The reaction mixture was allowed to cool to room temperature, purified water (50 mL) was added, and the precipitated solid was collected by filtration. The obtained solid was slurry-washed in acetonitrile and filtered, and the obtained solid was purified by silica gel column chromatography (dichloromethane-hexane) to give the title compound (2.31 g, 80.5%) as a white solid.

(2) Synthesis of 3,4,5-tris[3,4,5-tris(octadecyloxy)benzyloxy]benzyl alcohol

Methyl {3,4,5-tris[3,4,5-tris(octadecyloxy)benzyloxy]}benzoate (1.01 g, 350 μmol) was dissolved in dehydrating cyclopentyl methyl ether (20 mL) and, under ice-cooling, lithium aluminum hydride (31.8 mg, 840 μmol) was added, and the mixture was stirred at room temperature for 2 hr. After completion of the reaction, 0.1 mol/L aqueous hydrochloric acid was added dropwise to decompose unreacted lithium aluminum hydride and the mixture was washed with 1.0 mol/L aqueous hydrochloric acid. The organic layer was dried over sodium sulfate and filtered. The obtained filtrate was concentrated under reduced pressure, methanol was added, and the precipitated solid was collected by filtration and dried under reduced pressure to give the title compound (940 mg, 94.6%) as a white solid.

TLC: Rf=0.80 (dichloromethane:hexane=2:1)

$^1$H-NMR (400 MHz): δ 0.88 (t, 27H, J=7.0 Hz, H$_3$C-octadecyloxy), 1.26-1.75 (m, 306H, —CH$_2$-octadecyloxy), 3.77 (t, 4H, J=6.6 Hz, —O—CH$_2$-octadecyloxy), 3.87 (t, 10H, J=6.6 Hz, —O—CH$_2$-octadecyloxy), 3.92 (t, 4H, J=6.6 Hz, —O—CH$_2$-octadecyloxy), 4.57 (d, 2H, J=6.0 Hz, HO—CH$_2$-benzyl), 4.97 (s, 2H, HO-benzyl-O—CH$_2$-phenyl), 5.01 (s, 4H, HO-benzyl-O—CH$_2$-phenyl), 6.61 (s, 4H, HO-benzyl-O-benzyl), 6.63 (s, 2H, HO-benzyl-O-benzyl), 6.66 (s, 2H, HO-benzyl-O-benzyl).

Reference Example 8

Synthesis of 4,4'-bis(docosyloxy)benzhydrol

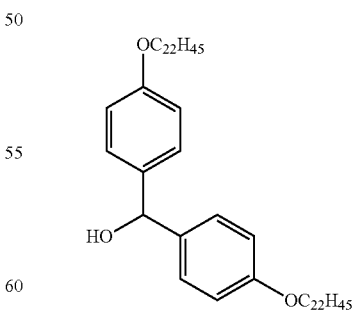

(1) Synthesis of 4,4'-didocosyloxy-benzophenone

To 4,4'-dihydroxy-benzophenone (8.2 g, 38.3 mmol) and 1-bromodocosane (31.3 g, 80.4 mmol) were added DMF (300 mL) and potassium carbonate (15.9 g, 115 mmol), and the mixture was stirred at 80° C. for 6.5 hr. After confirmation of the disappearance of the monoalkylated compound, the reaction mixture was ice-cooled, and 1N hydrochloric acid (300 mL) and water (150 mL) were slowly added to the thoroughly-stirred mixture. The slurry was filtered, and the obtained crystals were washed with water and methanol to give the title compound (28.3 g, 34.1 mmol, 89%).

$^1$H-NMR (CDCl$_3$/300 MHz) δ=0.88 (6H, t, J=6.6 Hz, OC$_{22}$H$_{45}$ C22-H), 1.1-1.6 (76H, br, OC$_{22}$H$_{45}$C3-21-H), 1.81 (4H, m, OC$_{22}$H$_{45}$C2-H), 2.04 (1H, s, —OH), 4.03 (4H, t, J=6.5 Hz, OC$_{22}$H$_{45}$C1-H), 6.94 (4H, d, J=8.8 Hz, Ph C3,3', 5,5'-H), 7.77 (4H, d, J=8.7 Hz, Ph C2,2',6,6'-H)

(2) Synthesis of 4,4'-bis(docosyloxy)benzhydrol

To 4,4'-didocosyloxy-benzophenone (28.3 g, 34.1 mmol) were added THF (300 mL) and methanol (15 mL), and the mixture was heated to 60° C. Sodium borohydride (6.10 g, 161 mmol) was slowly added, and the mixture was stirred at the same temperature for 4 hr. The reaction mixture was ice-cooled, and 1N hydrochloric acid (80 mL) was added dropwise. THF was evaporated, water (450 mL) was added, and 1N hydrochloric acid was added to adjust the pH to 5-7. The slurry was filtered, and the obtained crystals were washed with water and methanol to give the title compound (28.5 g, 34.1 mmol, 99%).

$^1$H-NMR (CDCl$_3$/300 MHz) δ 0.88 (6H, t, J=6.6 Hz, OC$_{22}$H$_{45}$C22-H), 1.1-1.6 (76H, br, OC$_{22}$H$_{45}$C3-21-H), 1.73 (4H, m, OC$_{22}$H$_{45}$C2-H), 2.04 (1H, s, —OH), 3.93 (4H, t, J=6.6 Hz, OC$_{22}$H$_{45}$C1-H), 5.76 (1H, s, HO—CHPh$_2$), 6.85 (4H, d, J=8.7 Hz, Ph C3,3',5,5'-H), 7.25 (4H, d, J=8.6 Hz, Ph C2,2',6,6'-H)

Reference Example 9

Synthesis of 4,4'-bis(docosyloxy)benzhydryl amine

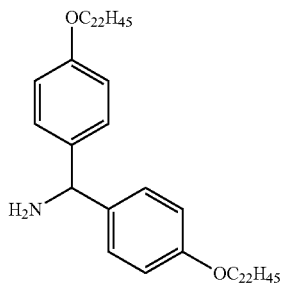

(1) Synthesis of N-(9-fluorenylmethoxycarbonyl)-bis (4-docosyloxyphenyl)methyl amine To 4,4'-bis(docosyloxy)benzhydrol (713 mg, 856 μmmol) were added toluene (15 ml), 9-fluorenylmethylcarbamate (246 mg, 1.03 mmol) and methanesulfonic acid (8.3 μl, 128 μmol), and the mixture was stirred at 100° C. for 3 hr. The disappearance of 4,4'-bis(docosyloxy)benzhydrol was confirmed, and the mixture was cooled to room temperature. 2.5% Aqueous sodium bicarbonate (10 ml) was added, and the mixture was stirred. The mixture was partitioned, and the organic layer was further washed with water (10 ml×2). The organic layer was evaporated under reduced pressure, and the residue was washed with methanol (10 ml) to give the title compound (540 mg, 512 μmol, yield 60%).

$^1$H-NMR (CDCl$_3$/300 MHz) δ 0.88 (9H, t, J=6.6, C$_{21}$H$_{42}$—CH$_3$), 1.10-1.50 (82H, br, Alkyl-H), 1.77 (4H, m, —O—CH$_2$—CH$_2$—C$_{20}$H$_{41}$), 3.93 (4H, d, J=6.6, —O—CH$_2$—C$_{21}$H$_{43}$), 4.21 (1H, br, s, fluorene C9-H), 4.43 (2H, br, d, J=6.6, fluorene-CH$_2$—O), 5.23 (1H, br, s, Fmoc-NH— or Fmoc-NH—CH), 5.85 (1H, br, s, Fmoc-NH— or Fmoc-NH—CH), 6.84 (4H, d, J=8.7, Ph C3,5-H), 7.11 (4H, d, J=8.7, Ph C2,6-H), 7.25-7.35 (2H, br, m, fluorene C2,7-H), 7.39 (2H, br, t, J=6.9, fluorene C3,6-H), 7.59 (2H, br, s, fluorene C1,8-H), 7.75 (2H, br, d, J=6.6, fluorene C4,5-H)

(2) Synthesis of 4,4'-bis(docosyloxy)benzhydryl amine

To dichloromethane (10 ml) was added DBU (1,8-diazabicyclo[5,4,0]-7-undecene, 200 μl), the compound (500 mg, 474 μmol) obtained in Reference Example 9(1) was added thereto, and the mixture was stirred at room temperature for 5 hr. 1N Hydrochloric acid (1.3 ml) was added dropwise, and the mixture was stirred. The solvent was evaporated, and the residue was washed with acetonitrile (10 ml) to give the title compound (340 mg, 408 μmol, yield 86%).

$^1$H-NMR (CDCl$_3$/300 MHz) δ 0.88 (6H, t, J=6.6 Hz, OC$_{22}$H$_{45}$C22-H), 1.1-1.6 (78H, br, OC$_{22}$H$_{45}$C3-21-H, —NH$_2$), 1.75 (4H, m, OC$_{22}$H$_{45}$ C2-H), 3.92 (4H, t, J=6.6 Hz, OC$_{22}$H$_{45}$C1-H), 5.12 (1H, s, H$_2$N—CHPh$_2$) 6.83 (4H, d, J=8.6 Hz, Ph C3,3',5,5'-H), 7.24 (4H, d, J=8.6 Hz, Ph C2,2', 6,6'-H)

Example 1

(Synthesis of Nucleoside): Synthesis of 5'-O-(4,4'-dimethoxytrityl)deoxythymidin-3'-yl-[3,4,5-tris(octadecyloxy)benzyl]succinate

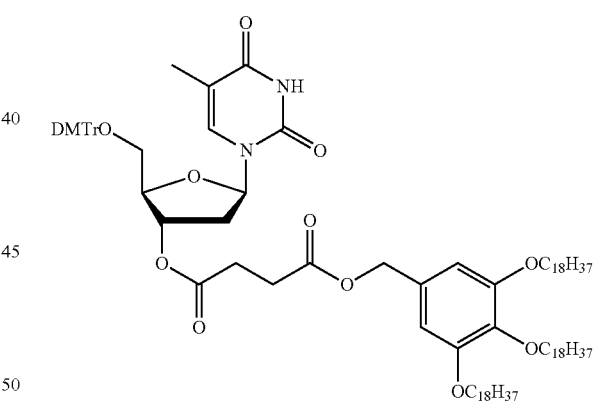

(1) Synthesis of 5'-O-(4,4'-dimethoxytrityl)deoxythymidine-3'-O-succinate

Under an argon atmosphere, 5'-O-(4,4'-dimethoxytrityl) deoxythymidine (5.00 g, 9.18 mmol), succinic anhydride (1.38 g, 13.8 mmol) and triethylamine (3.85 mL, 27.5 mmol) were dissolved in dichloromethane (95 mL), and the mixture was stirred at room temperature for 8 hr. The completion of the reaction was confirmed by thin layer chromatography, and the reaction mixture was partitioned and washed three times with 2.0M phosphoric acid-triethylamine buffer (pH 7.50). The organic layer was evaporated under reduced pressure to give a triethylamine salt (7.02 g, 98%) of 5'-O-(4,4'-dimethoxytrityl)deoxythymidine-3'-O-succinate as a colorless frothy solid.

(2) Synthesis of 5'-O-(4,4'-dimethoxytrityl)deoxythymidin-3'-yl-[3,4,5-tris(octadecyloxy)benzyl]succinate 3,4,5-Tris(octadecyloxy)benzyl alcohol (3.06 g, 3.35 mmol) was dissolved in dichloromethane (35 mL), a triethylamine salt (3.00 g, 4.02 mmol) of 5'-O-(4,4'-dimethoxytrityl)deoxythymidine-3'-O-succinate, 2-(1H-benzotriazol-1-yl)-1,1,3,3-tetramethyluronium hexafluorophosphate [HBTU] (1.98 g, 5.23 mmol), diisopropylethylamine (925 μL, 5.23 mmol) and dimethylaminopyridine (639 mg, 5.23 mmol) were added, and the mixture was stirred. The completion of the reaction was confirmed by thin layer chromatography, methanol was added, and the mixture was concentrated and suction-filtered to give 5'-O-(4,4'-dimethoxytrityl)deoxythymidin-3'-yl-[3,4,5-tris(octadecyloxy)benzyl]succinate (4.77 g, yield 93%) as a white solid.

Rf=0.78 ($CH_2Cl_2$/MeOH, 10:1).

$^1$H-NMR (400 MHz): δ=0.88 (t, 9H, Ar—C$\underline{H}_3$), 1.29 (br, s, 90H, (C$\underline{H}_2$)$_{15}$), 1.36 (s, 3H, N$^5$—C$\underline{H}_3$), 1.77 (m, 6H, Ar—OC$\underline{H}_2$C$\underline{H}_2$), 2.45 (m, 2H, 2'-$\underline{H}$), 2.67 (m, 4H, succinyl-C$\underline{H}_2$C$\underline{H}_2$), 3.48 (m, 2H, 5'-$\underline{H}$), 3.79 (s, 6H, DMTr-OC$\underline{H}_3$), 3.95 (m, 6H, Ar—OC$\underline{H}_2$), 4.12 (m, 1H, 4'-$\underline{H}$), 5.01 (s, 2H, Ar—C$\underline{H}_2$-succinyl), 5.50 (m, 1H, 3'-$\underline{H}$), 6.42 (t, 1H, 1'-$\underline{H}$), 6.53 (s, 2H, Ar—$\underline{H}$), 6.84-7.26 (m, 13H, DMTr-Ar—$\underline{H}$), 7.60 (s, 1H, N$^6$—$\underline{H}$).

Example 2

(Continuous Synthesis 1 of Dinucleotide in Solution): Synthesis of 5'-O-(4,4'-dimethoxytrityl)deoxythymidine-3'-[O-(2-cyanoethyl)]phosphoryl-deoxythymidin-3'-yl-[3,4,5-tris(octadecyloxy)benzyl]succinate

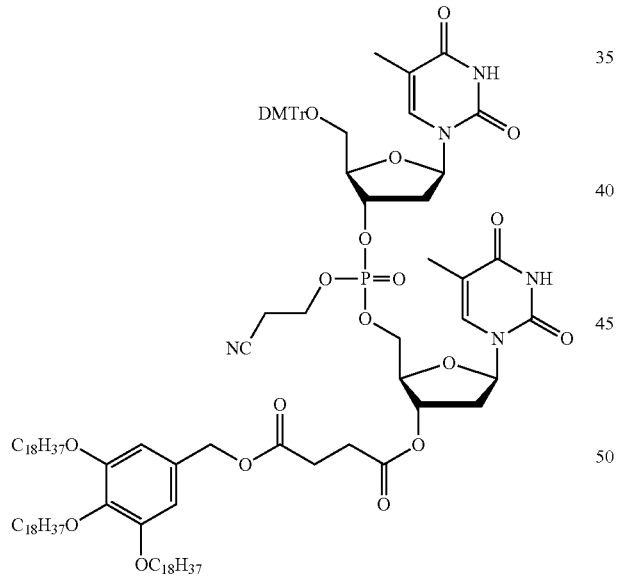

Under an argon atmosphere, 5'-O-(4,4'-dimethoxytrityl)deoxythymidin-3'-yl-[3,4,5-tris(octadecyloxy)benzyl]succinate (511 mg, 332 μmol) was dissolved in dichloromethane (5.11 mL), pyrrole (230 μL, 3.32 mmol) and trifluoroacetic acid (296 μL, 3.98 mmol) were added, and the mixture was stirred at room temperature for 15 min. The completion of the reaction was confirmed by thin layer chromatography. The reaction mixture was neutralized with pyridine (322 μL, 3.98 mmol), a solution of N-methylimidazole (158 μL, 1.99 mmol) and 5'-O-(4,4'-dimethoxytrityl)deoxythymidine-3'-[O-(2-cyanoethyl)-(N,N-diisopropyl)]-phosphoramidite (494 mg, 664 μmol) in acetonitrile were added, and the mixture was stirred at room temperature for 60 min. The completion of the reaction was confirmed by thin layer chromatography. Furthermore, 0.2M iodine pyridine/THF/$H_2O$ solution (3.32 mL) was added, and the mixture was stirred at room temperature for 10 min. A methanol solution saturated with sodium thiosulfate was poured into a reaction vessel, and the mixture was stirred at 0° C. for 10 min, suction-filtered using Kiriyama funnel, and dried to give 5'-β-(4,4'-dimethoxytrityl)deoxythymidine-3'-[O-(2-cyanoethyl)]phosphoryl deoxythymidin-3'-yl-[3,4,5-tris(octadecyloxy)benzyl]succinate (59 7 mg, 99.2%) as a white solid.

$^1$H-NMR (400 MHz): δ=0.88 (t, 9H, J=7.04 Hz, Ar—C$\underline{H}_3$), 1.26 (br, s, 90H, (C$\underline{H}_2$)$_{15}$), 1.30 (s, 3H, N$_1^5$—C$\underline{H}_3$), 1.40 (s, 3H, N$_2^5$—C$\underline{H}_3$), 1.77 (m, 6H, Ar—OC$\underline{H}_2$C$\underline{H}_2$), 2.30 (m, 2H, 2'$_1$—$\underline{H}$), 2.40 (m, 2H, 2'$_2$-$\underline{H}$), 2.68 (m, 4H, succinyl-C$\underline{H}_2$C$\underline{H}_2$), 2.75 (m, 2H, 5'$_1$—$\underline{H}$), 3.39 (m, 2H, 5'$_2$-$\underline{H}$), 3.79 (s, 6H, DMTr-OC$\underline{H}_3$), 3.94 (m, 6H, Ar—OC$\underline{H}_2$), 4.11 (m, 1H, 4'$_1$-$\underline{H}$), 4.25 (m, 4H, cyanoethyl-C$\underline{H}_2$C$\underline{H}_2$ and m, 1H, 4'$_2$-$\underline{H}$) 5.00 (s, 2H, Ar—C$\underline{H}_2$-succinyl), 5.18 (m, 1H, 3'$_2$-$\underline{H}$), 5.27 (m, 1H, 3'$_1$-$\underline{H}$), 6.24 (m, 1H, 1'$_1$-$\underline{H}$), 6.42 (m, 1H, 1'$_2$-$\underline{H}$), 6.53 (s, 2H, Ar—$\underline{H}$), 6.83-7.38 (m, 13H, DMTr-Ar—$\underline{H}$), 7.38 (m, 1H, N$^6$—$\underline{H}$), 7.53 (m, 1H, N$^6$—$\underline{H}$)

$^1$H-NMR (400 MHz): δ=0.88 (t, 9H, J=7.04 HZ, Ar—C$\underline{H}_3$), 1.26 (br, s, 90H, (C$\underline{H}_2$)$_{15}$), 1.30 (s, 3H, N$_1^5$—C$\underline{H}_3$), 1.40 (s, 3H, N$_2^5$—C$\underline{H}_3$), 1.77 (m, 6H, Ar—OC$\underline{H}_2$C$\underline{H}_2$), 2.30 (m, 2H, 2'$_1$—$\underline{H}$), 2.68 (m, 2H, 2'$_2$—H and m, 4H, succinyl-C$\underline{H}_2$C$\underline{H}_2$), 2.75 (m, 2H, 5'$_1$—$\underline{H}$), 3.53 (m, 2H, 5'$_2$-$\underline{H}$), 3.79 (s, 6H, DMTr-OC$\underline{H}_3$), 3.94 (m, 6H, Ar—OC$\underline{H}_2$), 4.11 (m, 1H, 4'$_1$—$\underline{H}$), 4.25 (m, 4H, cyanoethyl-C$\underline{H}_2$C$\underline{H}_2$ and m, 1H, 4'$_2$—$\underline{H}$), 5.01 (s, 2H, Ar—C$\underline{H}_2$-succinyl), 5.18 (m, 1H, 3'$_2$—$\underline{H}$), 5.31 (m, 1H, 3'$_1$-$\underline{H}$), 6.24 (m, 1H, 1'$_1$—$\underline{H}$), 6.42 (m, 1H, 1'$_2$—$\underline{H}$), 6.53 (s, 2H, Ar—$\underline{H}$), 6.83-7.38 (m, 13H, DMTr-Ar—$\underline{H}$), 7.38 (m, 1H, N$_1^6$—$\underline{H}$), 7.53 (m, 1H, N$_2^6$—$\underline{H}$)

Example 3

(Continuous synthesis of phosphorthioate dimer in solution): Synthesis of 5'-O-(4,4'-dimethoxytrityl)deoxythymidine-3'-[O-(2-cyanoethyl)]phosphorthionyl deoxythymidin-3'-yl-[3,4,5-tris(octadecyloxy)benzyl]succinate

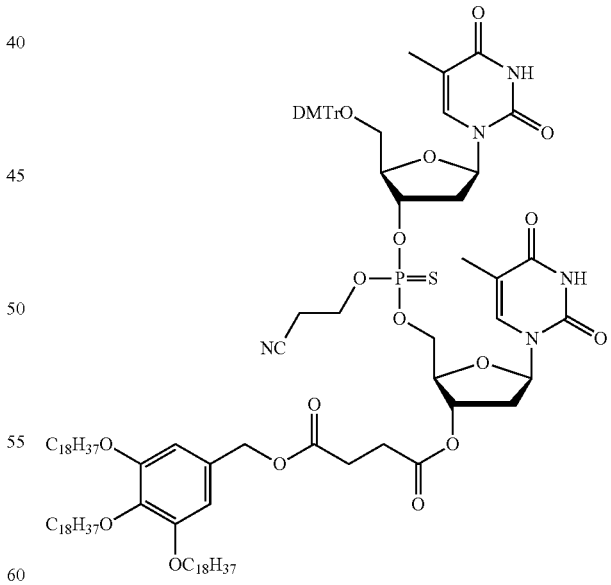

Under an argon atmosphere, 5'-O-(4,4'-dimethoxytrityl)deoxythymidin-3'-yl-[3,4,5-tris(octadecyloxy)benzyl]succinate (200 mg, 130 μmol) was dissolved in dichloromethane (3.00 mL), pyrrole (89.8 μL, 1.30 mmol) and trifluoroacetic acid (116 μL, 1.56 mmol) were added, and the mixture was stirred at room temperature for 15 min. The completion of the reaction was confirmed by thin layer chromatography. The reaction mixture was neutralized with pyridine (126 µL, 1.56 mmol), a solution of N-methylimidazole (61.8 µL, 0.779 mmol) and 5'-O-(4,4'-dimethoxytrityl)deoxythymidine-3'-[O-(2-cyanoethyl)-(N,N-diisopropyl)]-phosphoramidite (194 mg, 260 µmol) in acetonitrile was added, and the mixture was stirred at room temperature for 60 min. The completion of the reaction was confirmed by thin layer chromatography. Furthermore, 0.05M 3-((N,N-dimethylaminomethylidene)amino)-3H-1,2,4-dithiazole-5-thione pyridine/acetonitrile solution (7.79 mL) was added, and the mixture was stirred at room temperature for 30 min. A methanol solution saturated with sodium thiosulfate was poured into a reaction vessel, suction-filtered using Kiriyama funnel, and dried to give 5'-O-(4,4'-dimethoxytrityl)-deoxythymidine-3'-[O-(2-cyanoethyl)]phosphorthionyl deoxythymidin-3'-yl-[3,4,5-tris(octadecyloxy)benzyl]succinate (247 mg, 99.5%) as a white solid.

$^{1}$H-NMR (400 MHz): δ=0.88 (t, 9H, J=6.8 Hz, Ar—CH$_3$), 1.28 (br, s, 90H, (CH$_2$)$_{15}$), 1.30 (s, 3H, N$_1^5$—CH$_3$), 1.46 (s, 3H, N$_2^5$—CH$_3$), 1.73 (m, 6H, Ar—OCH$_2$CH$_2$), 2.28 (m, 2H, 2'$_1$—H), 2.41 (m, 2H, 2'$_2$—H), 2.68 (m, 2H, 5'$_1$—H and m, 4H, succinyl-CH$_2$CH$_2$), 3.44 (m, 2H, 5'$_2$-H), 3.79 (s, 6H, DMTr-OCH$_3$), 3.95 (m, 6H, Ar—OCH$_2$), 4.10 (m, 1H, 4'$_1$—H), 4.31 (m, 4H, cyanoethyl-CH$_2$CH$_2$ and m, 1H, 4'$_2$-H), 5.01 (s, 2H, Ar—CH$_2$-succinyl), 5.26 (m, 1H, 3'$_1$—H), 5.32 (m, 1H, 3'$_2$-H), 6.27 (m, 1H, 1'$_1$—H), 6.38 (m, 1H, 1'$_2$-H), 6.53 (s, 2H, Ar—H), 6.84-7.29 (m, 13H, DMTr-Ar—H), 7.29 (m, 1H, N$_1^6$—H), 7.56 (m, 1H, N$_2^6$—H)

$^{1}$H-NMR (400 MHz): δ=0.88 (t, 9H, Ar—CH$_3$), 1.28 (br, s, 90H, (CH$_2$)$_{15}$), 1.30 (s, 3H, N$_1^5$—CH$_3$), 1.46 (s, 3H, N$_2^5$—CH$_3$), 1.73 (m, 6H, Ar—OCH$_2$CH$_2$), 2.41 (m, 2H, 2'$_2$—H), 2.68 (m, 2H, 2'$_1$—H and m, 4H, succinyl-CH$_2$CH$_2$), 2.77 (m, 2H, 5'$_1$—H), 3.44 (m, 2H, 5'$_2$-H), 3.79 (s, 6H, DMTr-OCH$_3$), 3.95 (m, 6H, Ar—OCH$_2$), 4.17 (m, 1H, 4'$_1$-H), 4.31 (m, 4H, cyanoethyl-C$\overrightarrow{H_2CH_2}$ and m, 1H, 4'$_2$—H), 5.01 (s, 2H, Ar—CH$_2$-succinyl), 5.33 (m, 1H, 3'$_1$—H and m, 1H, 3'$_2$-H), 6.27 (m, 1H, 1'$_1$-H), 6.38 (m, 1H, 1'$_2$—H), 6.53 (s, 2H, Ar—H), 6.84-7.29 (m, 13H, DMTr-Ar—H), 7.29 (m, 1H, N$_1^5$—H), 7.56 (m, 1H, N$_2^5$—H)

Example 4

(continuous synthesis 2 of dinucleotide in solution): Synthesis of 5'-O-(4,4'-dimethoxytrityl)-2'-O-(tert-butyldimethylsilyl)uridine-3'-[O-(2-cyanoethyl)]phosphoryl deoxythymidin-3'-yl-[3,4,5-tris(octadecyloxy)benzyl]succinate

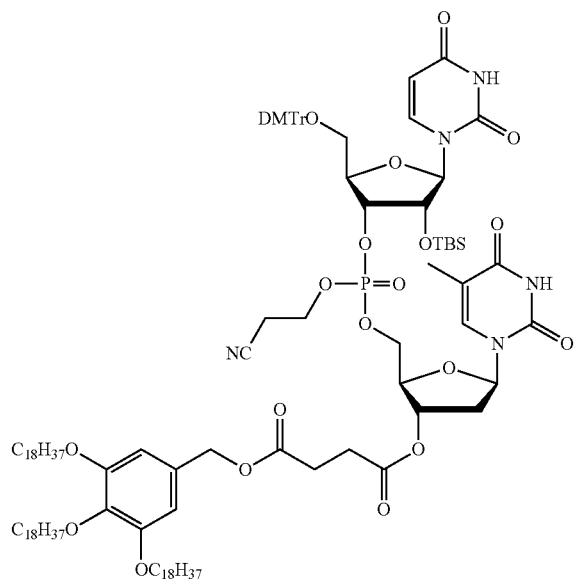

Under an argon atmosphere, 5'-O-(4,4'-dimethoxytrityl)deoxythymidin-3'-yl-[3,4,5-tris(octadecyloxy)benzyl]succinate (200 mg, 130 µmol) was dissolved in dichloromethane (3.00 mL), pyrrole (89.8 µL, 1.30 mmol) and trifluoroacetic acid (116 µL, 1.56 mmol) were added, and the mixture was stirred at room temperature for 15 min. The completion of the reaction was confirmed by thin layer chromatography. The reaction mixture was neutralized with pyridine (126 µL, 1.56 mmol), a solution of N-methylimidazole (61.8 µL, 0.779 mmol) and 5'-O-(4,4'-dimethoxytrityl)-2'-β-(tert-butyldimethylsilyl)uridine-3'-[O-(2-cyanoethyl)-(N,N-diisopropyl)]-phosphoramidite (224 mg, 260 µmol) in acetonitrile was added, and the mixture was stirred at room temperature for 60 min. The completion of the reaction was confirmed by thin layer chromatography. Furthermore, 0.2M iodine pyridine/THF/H$_2$O solution (1.33 mL) was added, and the mixture was stirred at room temperature for 10 min. A methanol solution saturated with sodium thiosulfate was poured into a reaction vessel, suction-filtered using Kiriyama funnel, and dried to give 5'-O-(4,4'-dimethoxytrityl)-2'-O-(tert-butyldimethylsilyl)uridine-3'-[O-(2-cyanoethyl)]phosphoryl deoxythymidin-3'-yl-[3,4,5-tris(octadecyloxy)benzyl]succinate (257 mg, 98.3%) as a white solid.

$^{1}$H-NMR (400 MHz): δ=0.13 (t, 6H, J=3.8 Hz, —OSi(Me$_2$)tBu), 0.88 (t, 9H, J=6.4, —OSi(Me$_2$)tBu and t, 9H, J=6.36, Ar—CH$_3$), 1.28 (br, s, 90H, (CH$_2$)$_{15}$), 1.30 (s, 3H, N$^5$—CH$_3$), 1.75 (m, 6H, Ar—OCH$_2$CH$_2$), 2.26 (m, 2H, 2'$_2$—H), 2.38 (m, 1H, 2'$_1$-H), 2.66 (m, 4H, succinyl-CH$_2$CH$_2$), 2.73 (m, 2H, 5'$_1$—H), 3.47 (m, 2H, 5'$_2$—H), 3.79 (s, 6H, DMTr-OCH$_3$), 3.94 (m, 6H, Ar—OCH$_2$), 4.25 (m, 4H, cyanoethyl-CH$_2$CH$_2$ and m, 1H, 4'$_1$—H), 4.51 (m, 1H, 4'$_2$—H), 4.93 (m, 1H, 3'$_2$—H), 5.00 (s, 2H, Ar—CH$_2$-succinyl), 5.20 (m, 1H, 3'$_1$—H), 5.25 (m, 1H, N$_1^5$—H), 5.97 (m, 1H, 1'$_1$-H), 6.21 (m, 1H, 1'$_2$-H), 6.53 (s, 2H, Ar—H), 6.85-7.28 (m, 13H, DMTr-Ar—H), 7.29 (m, 1H, N$_1^6$—H), 7.83 (m, 1H, N$_2^6$—H)

$^{1}$H-NMR (400 MHz): δ=0.13 (t, 6H, J=3.8 Hz, —OSi(Me$_2$)tBu), 0.88 (t, 9H, J=6.4, —OSi(Me$_2$)tBu and t, 9H, J=6.36, Ar—CH$_3$), 1.28 (br, s, 90H, (CH$_2$)$_{15}$), 1.30 (s, 3H, N$^5$—CH$_3$), 1.75 (m, 6H, Ar—OCH$_2$CH$_2$) 2.38 (m, 1H, 2'$_1$—H), 2.58 (m, 2H, 2'$_2$—H), 2.68 (m, 4H, succinyl-CH$_2$CH$_2$), 2.73 (m, 2H, 5'$_1$—H), 3.62 (m, 2H, 5'$_2$—H), 3.80 (s, 6H, DMTr-OCH$_3$), 3.94 (m, 6H, Ar—OC$\overrightarrow{H_2}$), 4.25 (m, 4H, cyanoethyl-CH$_2$CH$_2$ and m, 1H, 4'$_1$—H), 4.51 (m, 1H, 4'$_2$-H), 4.93 (m, 1H, 3'$_2$—H), 5.01 (s, 2H, Ar—CH$_2$-succinyl), 5.25 (m, 1H, N$_1^5$—H), 5.30 (m, 1H, 3'$_1$-H), 5.97 (m, 1H, 1'$_1$—H), 6.21 (m, 1H, 1'$_2$-H), 6.53 (s, 2H, Ar—H), 6.85-7.28 (m, 13H, DMTr-Ar—H), 7.29 (m, 1H, N$_1^6$—H), 7.83 (m, 1H, N$_2^6$—H)

Example 5

(continuous synthesis of 20mer oligonucleotide in solution): Synthesis of deoxythymidinyl-[3'→5']-deoxycytidinyl-[3'→5']-deoxycytidinyl-[3'→5']-deoxycytidinyl-[3'→5']-deoxyguanidyl-[3'→5']-deoxycytidinyl-[3'→5']-deoxycytidinyl-[3'→5']-deoxythymidinyl-[3'→5']-deoxyguanidyl-[3'→5']-deoxythymidinyl-[3'→5']-deoxyguanidyl-[3'→5']-deoxyadenylyl-[3'→5']-deoxycytidinyl-[3'→5']-deoxyadenylyl-[3'→5']-deoxythymidinyl-[3'→5']-deoxyguanidyl-[3'→5']-deoxycytidinyl-[3'→5']-deoxyadenylyl-[3'→5']-deoxythymidinyl-[3'→5']-deoxythymidine (TCCCGCCTGTGACATGCATT; SEQ ID NO: 1)

(1) Synthesis of 5'-O-(4,4'-dimethoxytrityl)-deoxythymidine 3'-[O-(2-cyanoethyl)]phosphoryl-$N^4$-benzoyl-deoxycytidine 3'-[O-(2-cyanoethyl)]phosphoryl-$N^4$-benzoyl-deoxycytidine 3'-[O-(2-cyanoethyl)]phosphoryl-$N^4$-benzoyl-deoxycytidine 3'-[O-(2-cyanoethyl)]phosphoryl-$N^2$-isobutyryl-deoxyguanosine 3'-[O-(2-cyanoethyl)]phosphoryl-$N^4$-benzoyl-deoxycytidine 3'-[O-(2-cyanoethyl)]phosphoryl-$N^4$-benzoyl-deoxycytidine 3'-[O-(2-cyanoethyl)]phosphoryl-deoxythymidine 3'-[O-(2-cyanoethyl)]phosphoryl-$N^2$-isobutyryl-deoxyguanosine 3'-[O-(2-cyanoethyl)]phosphoryl-deoxythymidine 3'-[O-(2-cyanoethyl)]phosphoryl-$N^2$-isobutyryl-deoxyguanosine 3'-[O-(2-cyanoethyl)]phosphoryl-$N^6$-benzoyl-deoxyadenosine 3'-[O-(2-cyanoethyl)]phosphoryl-$N^4$-benzoyl-deoxycytidine 3'-[O-(2-cyanoethyl)]phosphoryl-$N^6$-benzoyl-deoxyadenosine 3'-[O-(2-cyanoethyl)]phosphoryl-deoxythymidine 3'-[O-(2-cyanoethyl)]phosphoryl-$N^2$-isobutyryl-deoxyguanosine 3'-[O-(2-cyanoethyl)]phosphoryl-$N^4$-benzoyl-deoxycytidine 3'-[O-(2-cyanoethyl)]phosphoryl-$N^6$-benzoyl-deoxyadenosine 3'-[O-(2-cyanoethyl)]phosphoryl-deoxythymidine 3'-[O-(2-cyanoethyl)]phosphoryl-deoxythymidin-3'-yl-[3,4,5-tris(octadecyloxy)benzyl]succinate The operations in the same manner as in Example 2 were repeated 19 times to give the above-mentioned compound (2.55 g).

(2) Deprotection and Purification Step

The compound (100 mg, 10.3 μmol) synthesized in Example 5(1) and 30% aqueous ammonia:ethanol=3:1 solution (5.00 mL) were placed in an autoclave, and the mixture was heated at 80° C. for 2 hr, and freeze-dried. The freeze-dried product was diluted with 0.1M aqueous ammonium acetate solution, the mixture was applied to C-18 cartridge purification, and the obtained eluate was freeze-dried to give the object product, deoxythymidinyl-[3'→5]-deoxycytidinyl-[3'→5]-deoxycytidinyl-[3'→5']-deoxycytidinyl-[3'→5']-deoxyguanidyl-[3'→5']-deoxycytidinyl-[3'→5']-deoxycytidinyl-[3'→5']-deoxythymidinyl-[3'→5']-deoxyguanidyl-[3'→5']-deoxythymidinyl-[3'→5']-deoxyguanidyl-[3'→5']-deoxyadenylyl-[3'→5']-deoxycytidinyl-[3'→5']-deoxyadenylyl-[3'→5']-deoxythymidinyl-[3'→5']-deoxyguanidyl-[3'→5']-deoxycytidinyl-[3'→5']-deoxyadenylyl-[3'→5']-deoxythymidinyl-[3'→5']-deoxythymidine (TCCCGCCTGTGACATGCATT; SEQ ID NO: 1).

HPLC (shodex ODP (4.6 φ×150 mm), flow rate 1.0 mL/min, MeCN, $H_2O$ gradient: 0-15 min; 2 to 98%, 15 to 25 min; 98%, λ=254 nm): Rt=5.61 min (96.3%);

MALDI-TOF/MS: 6043.66 [M−H]$^-$

Experimental Example 1

Study of Cation Scavenger

Using the compound of Example 1 wherein the 5'-hydroxyl group is protected by 4,4'-dimethoxytrityl (hereinafter sometimes to be abbreviated as DMTr) (hereinafter sometimes to be abbreviated as a DMTr-protected compound) as a test compound, a DMTr cation scavenger candidate substance was tested and evaluated.

The DMTr-protected compound (50.0 mg, 32.5 μmol) was dissolved in dichloromethane (350 μL) to give a starting material solution, and a cation scavenger candidate substance (162 μmol) described in Table 1 was added. Trifluoroacetic acid (29.2 μL, 394 μmol) was added, and the mixture was stirred at room temperature for about 30 min until the disappearance of the spot of the DMTr-protected compound in the reaction mixture could be confirmed by both UV and color reaction under the following TLC measurement conditions.

Furthermore, the reaction mixture was neutralized with pyridine (31.8 μL, 394 μmol) and evaluation was conducted according to the following evaluation criteria under the following TLC measurement conditions.

○ (effective): when spot of DMTr-protected compound was not confirmed by both UV and color reaction x (ineffective): when spot of DMTr-protected compound was confirmed by any or both of UV and color reaction The results are shown in Table 1.

[Thin Layer Chromatography (TLC) Measurement Conditions]

The reaction mixture was spotted near the point of origin of a TLC plate (2 cm×5 cm rectangle, manufactured by Merch) by using a TLC spotting capillary tube (5 μL) (manufactured by Hirschmann Laborgeraete), developed with a developing solvent (dichloromethane/methanol=10/1), and confirmed by visual observation by UV (254 nm) and color reaction (after immersion in phosphomolybdic acid-ethanol solution, on a hot plate (about 300° C.) for 10 sec or above).

(DMTr-protected compound Rf value=0.70, DMTr-deprotected compound Rf value=0.40)

TABLE 1

| Cation scavengers | evaluation of scavenging of DMTr cation after neutralization (effective (○); ineffective (X)) | |
|---|---|---|
| methanol | ○ | non-protection state of 5'-hydroxyl group was maintained even after neutralization |
| dimethylsulfide | X | 5'-hydroxyl group was DMTr-ized after neutralization |
| anisole | X | 5'-hydroxyl group was DMTr-ized after neutralization |
| thioanisole | X | 5'-hydroxyl group was DMTr-ized after neutralization |
| m-cresol | X | 5'-hydroxyl group was DMTr-ized after neutralization |
| 1,3,5-trimethylbenzene | X | 5'-hydroxyl group was DMTr-ized after neutralization |
| 1,3-dimethoxybenzene, | X | 5'-hydroxyl group was DMTr-ized after neutralization |

TABLE 1-continued

| Cation scavengers | evaluation of scavenging of DMTr cation after neutralization (effective (○); ineffective (X)) | |
|---|---|---|
| 1,3,5-trimethoxybenzene | X | 5'-hydroxyl group was DMTr-ized after neutralization |
| triisopropylsilane | X | 5'-hydroxyl group was DMTr-ized after neutralization |
| triethylsilane | X | 5'-hydroxyl group was triethylsilylated after neutralization |
| pyrrole | ○ | non-protection state of 5'-hydroxyl group was maintained even after neutralization |
| 3-methylpyrrole | ○ | non-protection state of 5'-hydroxyl group was maintained even after neutralization |
| 2,4-dimethylpyrrole | ○ | non-protection state of 5'-hydroxyl group was maintained even after neutralization |
| indole | ○ | non-protection state of 5'-hydroxyl group was maintained even after neutralization |
| succinimide | X | 5'-hydroxyl group was DMTr-ized after neutralization |
| phthalimide | X | 5'-hydroxyl group was DMTr-ized after neutralization |

When dimethylsulfide, anisole, thioanisole, cresol, 1,3,5-trimethylbenzene, 1,3-dimethoxybenzene, 1,3,5-trimethoxybenzene, succinimide and phthalimide widely used as a cation scavenger were used, the 5'-terminal hydroxyl group was protected again by protecting group Q after neutralization, which clarifies that they do not sufficiently function as a cation scavenger. When trialkylsilane (e.g., triisopropylsilane, triethylsilane etc.), which is a conventionally-used cation scavenger, was used, trialkylsilane could not be used for the subsequent condensation step since the 5'-terminal hydroxyl group was trialkylsilylated after neutralization. Furthermore, it was found that use of methanol as a cation scavenger prevents the condensation reaction in the next step, though it irreversibly traps cation, and therefore, methanol cannot be used.

On the other hand, it was found that effective scavengers capable of maintaining the scavenging state of DMTr cation even after neutralization reaction were pyrrole derivatives such as pyrrole, 3-methylpyrrole, 2,4-dimethylpyrrole, and the like, and indole derivatives such as indole and the like.

Experimental Example 2

When Methanol was Used as Cation Scavenger

Using the compound of Example 1, wherein the 5'-hydroxyl-protecting group is 4,4'-dimethoxytrityl, as a test compound, whether or not methanol confirmed to be effective as a DMTr cation scavenger in Experimental Example 1 permits continuous synthesis of deprotection and condensation in solution was studied by the following method.

Under an argon atmosphere, 5'-O-(4,4'-dimethoxytrityl)deoxythymidin-3'-yl-[3,4,5-tris(octadecyloxy)benzyl]succinate (100 mg, 65.0 µmol) was dissolved in dichloromethane (1.5 mL), methanol (13.2 µL, 325 µmol) and trifluoroacetic acid (57.9 µL, 779 µmol) were added, and the mixture was stirred at room temperature for 15 min. The completion of the reaction was confirmed by HPLC. The reaction mixture was neutralized with pyridine (63.0 µL, 779 µmol), a solution of N-methylimidazole (30.9 µL, 390 µmol) and 5'-O-(4,4'-dimethoxytrityl)deoxythymidine-3'-[O-(2-cyanoethyl)-(N,N-diisopropyl)]-phosphoramidite (96.8 mg, 130 µmol) in acetonitrile was added, and the mixture was stirred at room temperature for 60 min and analyzed by HPLC. HPLC peak area values of the reaction system after deprotection reaction and after condensation reaction are shown in Table 2.

TABLE 2

| | HPLC peak area value (%) | |
|---|---|---|
| | test compound with deprotected DMTr | condensation product (same as Example 3 compound) |
| after deprotection | 96.9 | |
| after neutralization | 97.1 | |
| after condensation reaction | 92.6 | 3.2 |

The above-mentioned results have revealed that methanol maintained scavenging of DMTr cation even after neutralization but continuous condensation reactions in the same system do not advance condensation reaction.

Experimental Example 3

When Triethylsilane was Used as Cation Scavenger

Using the compound of Example 1, wherein the 5'-hydroxyl-protecting group is 4,4'-dimethoxytrityl, as a test compound and triethylsilane as a DMTr cation scavenger, deprotection was studied by the following method.

Under an argon atmosphere, 5'-O-(4,4'-dimethoxytrityl)deoxythymidin-3'-yl-[3,4,5-tris(octadecyloxy)benzyl]succinate (100 mg, 65.0 µmol) was dissolved in dichloromethane (1.5 ml), triethylsilane (51.7 µL, 325 µmol) and trifluoroacetic acid (57.9 µL, 779 µmol) were added, and the mixture was stirred at room temperature for 15 min. The completion of the reaction was confirmed by thin layer chromatography. The reaction mixture was neutralized with pyridine (63.0 µL, 779 µmol), and a methanol solution was supplied into a reaction vessel, suction-filtered using Kiriyama funnel, and dried. The solid obtained by drying was measured for $^1$H-NMR (below). As a result, a mixture of 5'-O-(triethylsilyl)deoxythymidin-3'-yl-[3,4,5-tris(octadecyloxy)benzyl]succinate wherein the 5'-hydroxyl group was triethylsilylated, and 5'-OH-deoxythymidin-3'-yl-[3,4,5-tris(octadecyloxy)benzyl]succinate was obtained at a proton intensity ratio at the 1'-position of 5'-triethylsilyl compound:5'-OH compound=0.26:1.00.

$^1$H-NMR (400 MHz): δ=0.68 (dd, 6H, Si(C$\underline{H}_2$CH$_3$)$_3$), 0.86 (t, 9H, Ar—C$\underline{H}_3$), 0.99 (t, 9H, (CH$_2$C$\underline{H}_3$)$_3$), 1.26 (br, s, 90H, (C$\underline{H}_2$)$_{15}$), 1.30 (s, 3H, N$^5$C$\underline{H}_3$), 1.75 (m, 6H, Ar—OCH$_2$C$\underline{H}_2$), 2.12 (m, 2H, 2'-$\underline{H}$), 2.68 (m, 6H, succinyl-C$\underline{H}_2$C$\underline{H}_2$), 3.88 (m, 2H, 5'-$\underline{H}$), 3.98 (m, 6H, Ar—OC$\underline{H}_2$), 4.07 (m, 1H, 4'-$\underline{H}$), 5.02 (s, 2H, Ar—C$\underline{H}_2$-succinyl), 5.28 (m, 1H, 3'-$\underline{H}$), 6.37 (t, 1H, 1'-$\underline{H}$), 6.54 (s, 2$\underline{H}$, Ar—$\underline{H}$), 7.62 (s, 1H, N$^6$—$\underline{H}$)

The above-mentioned results have revealed that triethylsilane is effective for DMTr cation scavenging during deprotection, but unsuitable as a DMTr cation scavenger, since it partly triethylsilylates the 5'-hydroxyl group of the deprotected compound after neutralization, and adversely affects continuous condensation steps.

Experimental Example 4

When Step of Precipitation and Isolation after Continuous Solution Reactions was Changed Using 5'-OH-deoxythymidin-3'-yl-[3,4,5-tris(octadecyloxy)benzyl]succinate as a test compound and condensation, oxidation and deprotection were continuously performed in this order in the same reaction system by the following method.

Under an argon atmosphere, 5'-OH-deoxythymidin-3'-yl-[3,4,5-tris(octadecyloxy)benzyl]succinate (79.3 mg, 52.3 μmol) was dissolved in dichloromethane (1.5 mL), a solution of 5'-β-(4,4'-dimethoxytrityl)deoxythymidine-3'-[O-(2-cyanoethyl)-(N,N-diisopropyl)]-phosphoramidite (77.9 mg, 105 μmol) and 1H-tetrazole (36.6 mg, 523 μmol) in acetonitrile was added, and the mixture was stirred at room temperature for 60 min. The completion of the reaction was confirmed by thin layer chromatography. Furthermore, 0.2M iodine pyridine/THF/$H_2O$ solution (1.1 mL) was added to the reaction mixture, and the mixture was stirred at room temperature for 10 min. After stirring, TFA (46.6 μL, 628 μmol) was added and the reaction was traced by HPLC analysis. The HPLC peak area values of the reaction system after condensation reaction and before addition of TFA or after stirring for 30 min at room temperature after addition of TFA are shown in Table 3.

TABLE 3

| | HPLC peak area value (%) | |
| --- | --- | --- |
| | condensation product wherein 5'-hydroxyl group is protected by DMTr group | condensation product wherein DMTr group is deprotected |
| before addition of TFA | 92.3 | |
| after addition of TFA | 91.0 | N.D. |

N.D.: not detected

The above-mentioned results have revealed that when a continuous solution synthesis method using iodine/pyridine as an oxidizing agent is started from the condensation reaction, the reaction system after the condensation reaction added with 2% TFA does not achieve deprotection of the DMTr group of the 5'-hydroxyl group. Therefrom it was found that a preferable order of reactions in the continuous solution synthesis of oligonucleotide in the present invention is removal (deprotection) of DMTr group, which is a temporary protecting group of 5'-hydroxyl group, condensation and oxidation, followed by precipitation by addition, after oxidation, of methanol and the like saturated with hypo, and isolation operation for solid-liquid separation.

Example 6

Synthesis of 5'-O-(4,4'-dimethoxytrityl)deoxythymidin-3'-yl-N-[3,4,5-tris(octadecyloxy)benzyl]succinamate

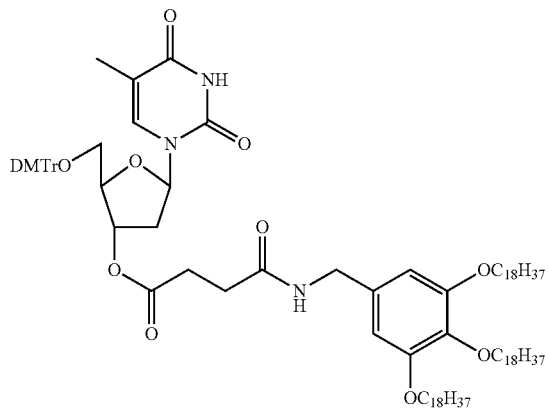

A triethylamine salt (1.45 g, 1.94 mmol) of 5'-O-(4,4'-dimethoxytrityl)deoxythymidine-3'-O-succinate and 3,4,5-tris(octadecyloxy)benzyl amine (1.02 g, 1.10 mmol) were dissolved in dehydrating dichloromethane (15 mL), 2-(1H-benzotriazol-1-yl)-1,1,3,3-tetramethyluronium hexafluorophosphate [HBTU] (2.53 g, 6.60 mmol) and N,N-diisopropylethylamine (1.17 mL, 6.60 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The organic layer was dried over sodium sulfate and filtered, and the filtrate was concentrated under reduced pressure. Methanol was added to the concentrated solution, the mixture was filtered, and the obtained solid was purified by silica gel column chromatography (dichloromethane/methanol, 1% v/v triethylamine) to give the title compound (1.22 g, 72.4%) as a white solid.

TLC: Rf=0.50 (dichloromethane:methanol=4:1)

$^1$H-NMR (400 MHz): δ 0.89 (t, 9H, J=7.0 Hz, $\underline{H_3}$C(octadecyloxy)), 1.25-1.79 (m, 102H, —$CH_2$— (octadecyloxy)), 1.35 (s, 3H, $N^5$—$CH_3$-thymidine), 2.45 (m, 2H, 2'-thymidine), 2.51 (m, 2H, succinyl), 2.70 (m, 2H, succinyl), 3.46 (m, 2H, 5'-thymidine), 3.79 (s, 6H, $\underline{H_3}$CO-DMTr), 3.79-3.95 (m, 6H, Bn—O—C$\underline{H_2}$—), 4.15 (m, 1H, 4'-thymidine), 4.32 (d, 2H, J=5.5 Hz, —NH—C$\underline{H_2}$-benzyl), 5.47 (m, 1H, 3'-thymidine), 5.72 (d, 2H, J=5.5 Hz, —NH—C$\underline{H_2}$-benzyl), 6.41 (m, 1H, 1'-Thymidine), 6.45 (s, 2H, -benzyl), 6.83 (d, 4H, J=9.0 Hz, DMTr), 7.24-7.38 (m, 9H, DMTr), 7.61 (s, 1H, $N^6$-thymidine), 7.95 (br s, $N^3$—N$\underline{H}$-thymidine)

Example 7

Synthesis of 5'-O-(4,4'-dimethoxytrityl)deoxythymidin-3'-yl-[3,5-bis(docosyloxy)benzyl]succinate

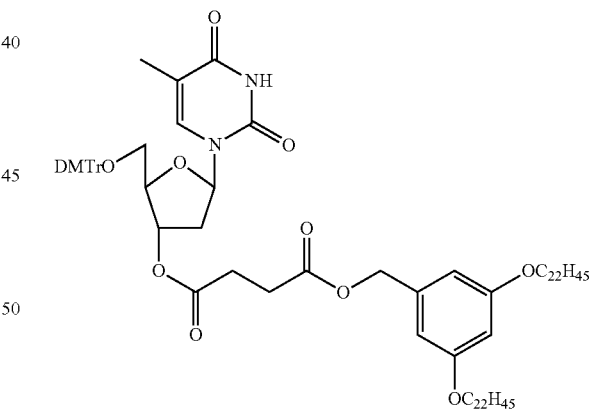

A triethylamine salt (837 mg, 1.12 mmol) of 5'-O-(4,4'-dimethoxytrityl)deoxythymidine-3'-O-succinate and 3,5-bis(docosyloxy)benzyl alcohol (500 mg, 660 μmol) were dissolved in a mixed solvent of dehydrating dichloromethane (10 mL) and dehydrating diethyl ether (10 mL), 2-(1H-benzotriazol-1-yl)-1,1,3,3-tetramethyluronium hexafluorophosphate [HBTU] (3.00 g, 7.82 mmol) and N,N-diisopropylethylamine (1.40 mL, 7.82 mmol) were added, and the mixture was stirred at 30° C. for 4 hr. The disappearance of the starting material was confirmed by thin layer chromatography, and the mixture was washed with saturated aqueous sodium hydrogen carbonate solution and saturated brine. The obtained organic layer was dried over sodium sulfate and filtered. The filtrate was concentrated under reduced pressure, and methanol was added. The precipitated solid was collected by filtration and purified by silica gel column chromatography (dichloromethane/methanol, 1% v/v triethylamine) to give the title compound (702 mg, 76.9%) as a white solid.

TLC: Rf=0.60 (dichloromethane:methanol=9:1)

$^1$H-NMR (400 MHz): δ 0.88 (t, 6H, J=7.0, H$_3$C-docosyloxy), 1.25-1.76 (m, 84H, —CH$_2$-docosyloxy), 1.35 (s, 3H, N$^5$—CH$_3$-thymidine), 2.45 (m, 2H, 2'-thymidine), 2.67 (m, 4H, succinyl), 3.46 (m, 2H, 5'-thymidine), 3.79 (s, 6H, CH$_3$O-DMTr), 3.90 (t, 4H, J=6.6 Hz, Bn—O—CH$_2$—), 4.11 (m, 1H, 4'-thymidine), 5.03 (s, 2H, NH—CH$_2$-benzyl), 5.47 (m, 1H, 3'-thymidine), 6.38 (m, 1H, 3'-thymidine), 6.85 (s, 2H, -benzyl), 6.83 (d, 4H, J=9.0, DMTr), 7.24-7.38 (m, 9H, DMTr), 7.60 (m, 1H, N$^6$-thymidine), 7.97 (br s, 1H, N$^3$—NH-thymidine)

Example 8

Synthesis of 5'-O-(4,4'-dimethoxytrityl)deoxythymidin-3'-yl-N-[3,5-bis(docosyloxy)benzyl]succinamate

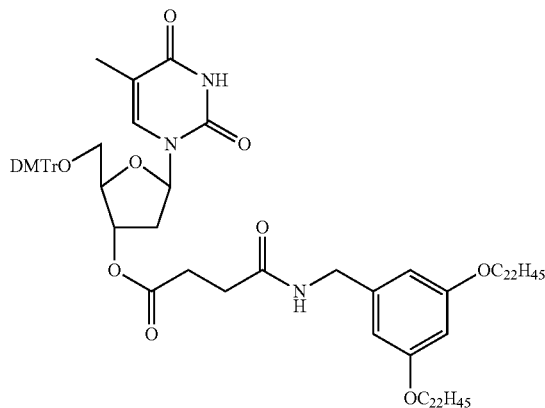

A triethylamine salt (223 mg, 299 μmol) of 5'-O-(4,4'-dimethoxytrityl)deoxythymidine-3'-O-succinate and 3,5-bis(docosyloxy)benzyl amine (133 mg, 175 μmol) were dissolved in dehydrating dichloromethane (5 mL), 2-(1H-benzotriazol-1-yl)-1,1,3,3-tetramethyluronium hexafluorophosphate [HBTU] (375 mg, 954 μmol) and N,N-diisopropylethylamine (170 μL, 954 μmol) were added, and the mixture was stirred at room temperature for 2 hr. The disappearance of the starting material was confirmed by thin layer chromatography, and the mixture was washed with saturated aqueous sodium hydrogen carbonate solution and saturated brine. The obtained organic layer was dried over sodium sulfate, filtered and concentrated under reduced pressure. Methanol was added to the filtrate, and the precipitated solid was collected by filtration. The obtained solid was dried under reduced pressure to give the title compound (205 mg, 84.6%) as a white solid.

TLC: Rf=0.40 (dichloromethane:methanol=9:1)

$^1$H-NMR (400 MHz): δ 0.88 (t, 6H, J=7.0, H$_3$C-docosyloxy), 1.25-1.75 (m, 84H, —CH$_2$-docosyloxy), 1.35 (s, 3H, N$^5$—CH$_3$-thymidine), 2.45 (m, 2H, 2'-thymidine), 2.52 (m, 2H, succinyl), 2.69 (m, 2H, succinyl), 3.46 (m, 2H, 5'-thymidine), 3.79 (s, 6H, CH$_3$O-DMTr), 3.89 (t, 4H, J=6.6 Hz, —O—CH$_2$-docosyloxy), 4.14 (m, 1H, 4'-thymidine), 4.34 (d, 2H, J=5.6 Hz, —NH—CH$_2$-benzyl), 5.47 (m, 1H, 3'-thymidine), 5.74 (t, 1H, J=5.6 Hz, —NH—CH$_2$-benzyl), 6.35 (m, 1H, 1'-thymidine), 6.38 (s, 2H, -benzyl), 6.83 (d, 4H, J=9.0 Hz, -DMTr), 7.24-7.38 (m, 9H, -DMTr), 7.61 (s, 1H, N$^6$-thymidine), 7.93 (br s, 1H, N$^3$—NH-thymidine)

Example 9

Synthesis of 5'-O-(4,4'-dimethoxytrityl)deoxythymidin-3'-yl-[2,4-bis(docosyloxy)benzyl]succinate

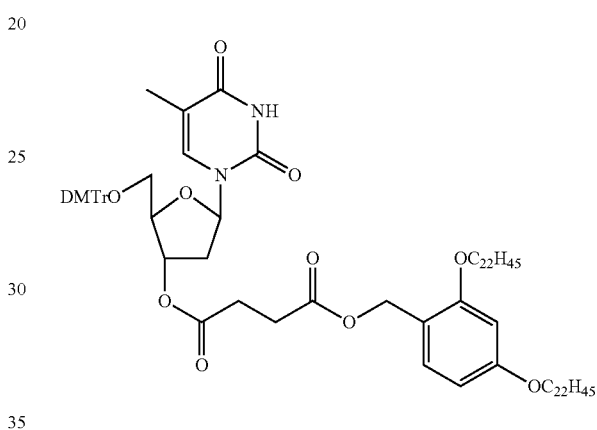

A triethylamine salt (1.69 g, 2.24 mmol) of 5'-O-(4,4'-dimethoxytrityl)deoxythymidine-3'-O-succinate and 2,4-bis(docosyloxy)benzyl alcohol (990 mg, 1.32 mmol) were dissolved in dehydrating dichloromethane (15 mL), 2-(1H-benzotriazol-1-yl)-1,1,3,3-tetramethyluronium hexafluorophosphate [HBTU] (2.77 g, 7.20 mmol) and N,N-diisopropylethylamine (1.28 mL, 7.20 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The obtained organic layer was dried over sodium sulfate, filtered and concentrated under reduced pressure. Methanol was added to the filtrate, and the precipitated solid was collected by filtration and dried to give the title compound (1.68 g, 92.0%) as a white solid.

TLC: Rf=0.70 (dichloromethane:methanol=9:1)

$^1$H-NMR (400 MHz): δ 0.88 (t, 6H, J=7.0 Hz, H$_3$C-docosyloxy), 1.25-1.75 (m, 84H, —CH$_2$-docosyloxy), 1.35 (s, 3H, N$^5$—CH$_3$-thymidine), 2.44 (m, 2H, 2'-thymidine), 2.64 (m, 4H, succinyl), 3.45 (m, 2H, 5'-thymidine), 3.79 (s, 6H, H$_3$C-DMTr), 3.92 (m, 4H, —O—CH$_2$-docosyloxy), 4.10 (m, 1H, 4'-thymidine), 5.11 (s, 2H, —O—CH$_2$-benzyl), 5.47 (m, 1H, 3'-thymidine), 6.39 (m, 1H, 1'-thymidine), 6.42 (s, 2H, -benzyl), 6.83 (d, 4H, J=8.9 Hz, -DMTr), 7.17-7.39 (m, 9H, -DMTr), 7.60 (s, 1H, N$^6$-thymidine), 7.97 (br s, 1H, N$^3$—NH-thymidine)

Example 10

Synthesis of 5'-O-(4,4'-dimethoxytrityl)deoxythymidin-3'-yl-N-[2,4-bis(docosyloxy)benzyl]succinamate

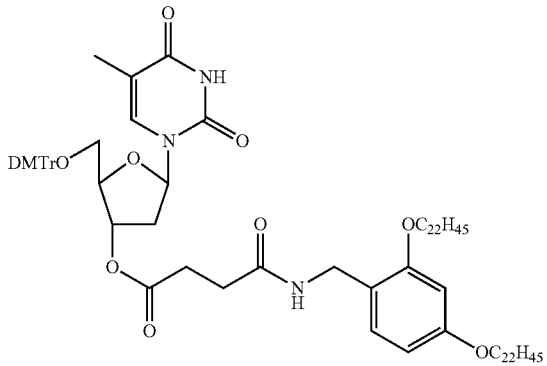

A triethylamine salt (1.70 g, 2.28 mmol) of 5'-O-(4,4'-dimethoxytrityl)deoxythymidine-3'-O-succinate and 2,4-bis(docosyloxy)benzyl amine (1.01 g, 1.32 mmol) were dissolved in dehydrating dichloromethane (15 mL), 2-(1H-benzotriazol-1-yl)-1,1,3,3-tetramethyluronium hexafluorophosphate [HBTU] (2.73 g, 7.20 mmol) and N,N-diisopropylethylamine (1.28 mL, 7.20 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The obtained organic layer was dried over sodium sulfate, filtered and concentrated under reduced pressure. Methanol was added to the filtrate, and the precipitated solid was collected by filtration and dried under reduced pressure to give the title compound (1.75 g, 96.0%) as a white solid.

TLC: Rf=0.60 (dichloromethane:methanol=9:1)

$^1$H-NMR (400 MHz): δ 0.88 (t, 6H, J=7.0 Hz, H$_3$C-docosyloxy), 1.25-1.74 (m, 84H, —CH$_2$-docosyloxy), 1.34 (s, 3H, N$^5$—CH$_3$-thymidine), 2.45 (m, 2H, 2'-thymidine), 2.46 (m, 2H, succinyl), 2.66 (m, 2H, succinyl), 3.45 (m, 2H, 5'-thymidine), 3.79 (s, 6H, H$_3$CO-DMTr), 3.89 (t, 2H, J=6.6 Hz, —O—CH$_2$-docosyloxy), 3.94 (t, 2H, J=6.6 Hz, —O—CH$_2$-docosyloxy), 4.11 (m, 1H, 4'-thymidine), 4.35 (d, 2H, J=5.7 Hz, —NH—CH$_2$-benzyl), 5.47 (m, 1H, 3'-thymidine), 5.93 (t, 1H, J=5.7 Hz, —NH—CH$_2$-benzyl), 6.38 (m, 1H, 1'-thymidine), 6.42 (s, 2H, -benzyl), 6.83 (d, 4H, J=9.0 Hz, -DMTr), 7.11-7.38 (m, 9H, -DMTr), 7.60 (s, 1H, N$^6$-thymidine), 7.96 (br s, 1H, N$^3$—NH-thymidine)

Example 11

Synthesis of 5'-O-(4,4'-dimethoxytrityl)deoxythymidin-3'-yl-N-[4,4'-bis(docosyloxy)benzhydryl]succinamate

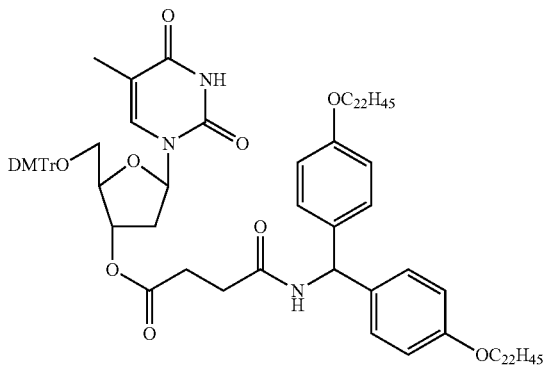

A triethylamine salt (2.02 g, 2.71 mmol) of 5'-O-(4,4'-dimethoxytrityl)deoxythymidine-3'-O-succinate and 4,4'-bis(docosyloxy)benzhydryl amine (1.25 g, 1.50 mmol) were dissolved in dehydrating dichloromethane (15 mL), 2-(1H-benzotriazol-1-yl)-1,1,3,3-tetramethyluronium hexafluorophosphate [HBTU] (3.40 g, 8.93 mmol) and N,N-diisopropylethylamine (1.56 mL, 9.00 mmol) were added, and the mixture was stirred at 40° C. overnight. The disappearance of the starting material was confirmed by thin layer chromatography, and the reaction mixture was concentrated under reduced pressure. Methanol was added to the concentrated solution, and the precipitated solid was collected by filtration. The obtained solid was purified by silica gel column chromatography (dichloromethane/methanol, 1% v/v triethylamine) to give the title compound (1.65 g, 75.3%) as a white solid.

TLC: Rf=0.70 (dichloromethane:methanol=10:1)

$^1$H-NMR (400 MHz): δ 0.88 (t, 6H, J=7.0 Hz, H$_3$C-docosyloxy), 1.25-1.76 (m, 84H, —CH$_2$-docosyloxy), 1.36 (s, 3H, N$^5$—CH$_3$-thymidine), 2.42 (m, 2H, 2'-thymidine), 2.55 (m, 2H, succinyl), 2.70 (m, 2H, succinyl), 3.45 (m, 2H, 5'-thymidine), 3.78 (s, 6H, H$_3$CO-DMTr), 3.89 (dt, 4H, J=6.7, 13.6 Hz, —O—CH$_2$-docosyloxy), 4.11 (m, 1H, 4'-thymidine), 5.48 (m, 1H, 3'-thymidine), 6.03 (d, 1H, J=7.8 Hz, —NH—CH-benzhydryl), 6.10 (d, 1H, J=7.8 Hz, —NH—CH-benzhydryl), 6.39 (m, 1H, 1'-thymidine), 6.81 (m, 4H, -benzhydryl), 6.83 (d, 4H, J=9.0 Hz, -DMTr), 7.08-7.39 (m, 9H+4H, -DMTr+-benzhydryl), 7.59 (s, 1H, N$^6$-thymidine), 7.89 (br s, 1H, N$^3$—NH-thymidine)

Example 12

Synthesis of 5'-O-(4,4'-dimethoxytrityl)deoxythymidin-3'-yl-N-[2,3,4-tris(octadecyloxy)benzhydryl]succinamate

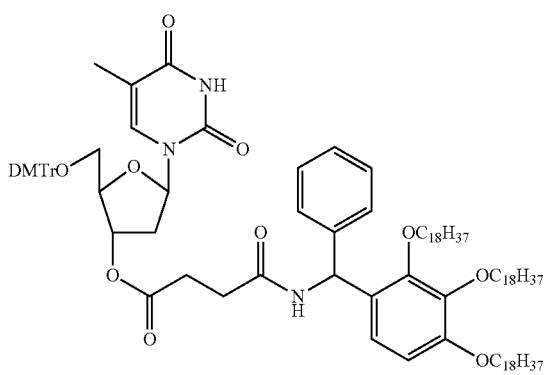

A triethylamine salt (1.29 g, 1.70 mmol) of 5'-O-(4,4'-dimethoxytrityl)deoxythymidine-3'-O-succinate and 2,3,4-tris(octadecyloxy)benzhydryl amine (1.01 g, 1.02 mmol) were dissolved in dehydrating dichloromethane (15 mL), 2-(1H-benzotriazol-1-yl)-1,1,3,3-tetramethyluronium hexafluorophosphate [HBTU] (2.31 g, 6.09 mmol) and N,N-diisopropylethylamine (1.07 mL, 6.06 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The obtained organic layer was dried over sodium sulfate, filtered and concentrated under reduced pressure. Methanol was added to the filtrate, and the precipitated solid was collected by filtration and dried under reduced pressure to give the title compound (1.14 g, 68.8%) as a white solid.

TLC: Rf=0.50 (dichloromethane:methanol=9:1)

$^1$H-NMR (400 MHz) spectra of diastereomer 1: δ 0.88 (t, 6H, J=7.0 Hz, H$_3$C-octadecyloxy), 1.16-1.80 (m, 3H+102H, N$^5$—CH$_3$-thymidine+-CH$_2$-octadecyloxy), 2.42-2.80 (m, 1H+4H, 2'-thymidine+succinyl), 3.26 (m, 2H, 2'-thymidine), 3.45 (m, 2H, 5'-thymidine), 3.78 (s, 6H, H$_3$CO-DMTr), 3.94 (m, 6H, —O—CH$_2$-octadecyloxy), 4.12 (m, 1H, 4'-thymidine), 5.50 (m, 1H, 3'-thymidine), 6.25 (d, 1H, J=8.6 Hz, —NH—CH-benzhydryl), 6.41 (m, 1H, 1'-thymidine), 6.59 (d, 1H, J=8.6 Hz, -benzhydryl), 6.74 (d, 1H, J=8.6 Hz, —NH—CH-benzhydryl), 6.83 (d, 4H, J=9.0 Hz, -DMTr), 6.90 (d, 1H, J=8.6 Hz, -benzhydryl), 7.11-7.39 (m, 9H+5H, -DMTr+-benzhydryl), 7.60 (s, 1H, N$^6$-thymidine), 8.00 (br s, 1H, N$^3$—NH-thymidine)

$^1$H-NMR (400 MHz) spectra of diastereomer 2: δ 0.88 (t, 6H, J=7.0 Hz, H$_3$C-octadecyloxy), 1.16-1.80 (m, 3H+102H, N$^5$—CH$_3$-thymidine+-CH$_2$-octadecyloxy), 2.42-2.80 (m, 1H+4H, 2'-thymidine+succinyl), 3.26 (m, 2H, 2'-thymidine), 3.45 (m, 2H, 5'-thymidine), 3.78 (s, 6H, H$_3$CO-DMTr), 3.94 (m, 6H, —O—CH$_2$-octadecyloxy), 4.12 (m, 1H, 4'-thymidine), 5.50 (m, 1H, 3'-thymidine), 6.26 (d, 1H, J=8.6 Hz, —NH—CH-benzhydryl), 6.41 (m, 1H, 1'-thymidine), 6.61 (d, 1H, J=8.6 Hz, -benzhydryl), 6.76 (d, 1H, J=8.6 Hz, —NH—CH-benzhydryl), 6.83 (d, 4H, J=9.0 Hz, -DMTr), 6.92 (d, 1H, J=8.6 Hz, -benzhydryl), 7.11-7.39 (m, 9H+5H, -DMTr+-benzhydryl), 7.60 (s, 1H, N$^6$-thymidine), 8.00 (br s, 1H, N$^3$—NH-thymidine)

Example 13

Synthesis of 5'-O-(4,4'-dimethoxytrityl)deoxythymidin-3'-yl-{3,4,5-tris[3,4,5-tris(octadecyloxy)benzyloxy]benzyl}succinate

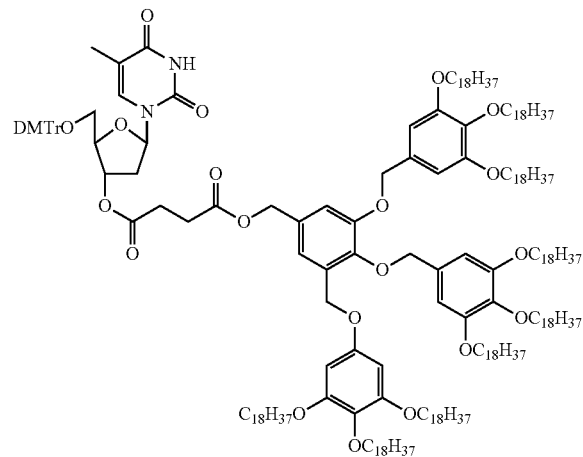

A triethylamine salt (408 mg, 548 μmol) of 5'-O-(4,4'-dimethoxytrityl)deoxythymidine-3'-O-succinate and 3,4,5-tris[3,4,5-tris(octadecyloxy)benzyloxy]benzyl alcohol (904 mg, 318 μmol) were dissolved in dehydrating dichloromethane (10 mL), 2-(1H-benzotriazol-1-yl)-1,1,3,3-tetramethyluronium hexafluorophosphate [HBTU] (1.09 g, 2.87 mmol) and N,N-diisopropylethylamine (507 μL, 2.85 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The obtained organic layer was dried over sodium sulfate, filtered and concentrated under reduced pressure. Methanol was added to the filtrate, and the precipitated solid was collected by filtration and purified by silica gel column chromatography (dichloromethane/methanol=99/2, 1% v/v triethylamine) to give the title compound (207 mg, 65.2%) as a white solid.

TLC: Rf=0.50 (dichloromethane:methanol=19:1)

$^1$H-NMR (400 MHz): δ 0.88 (t, 27H, J=6.9, H$_3$C-octadecyloxy), 1.25-1.75 (m, 306H, —CH$_2$-octadecyloxy), 1.35 (s, 3H, N$^5$—CH$_3$-thymidine), 2.47 (m, 2H, 2'-thymidine), 2.66 (m, 4H, succinyl), 3.47 (m, 2H, 5'-thymidine), 3.74 (t, 4H, J=6.3 Hz, -benzyl-O—CH$_2$-octadecyloxy), 3.78 (s, 6H, CH$_3$O-DMTr), 3.86 (t, 10H, J=6.3 Hz, -benzyl-O—CH$_2$-octadecyloxy), 3.92 (t, 4H, J=6.3 Hz, -benzyl-O—CH$_2$-octadecyloxy), 4.15 (m, 1H, 4'-thymidine), 4.99 (m, 2H+6H, —O—CH$_2$-benzyl-O—CH$_2$-benzyl-O—CH$_2$-benzyl-O—CH$_2$-benzyl), 5.48 (m, 1H, 3'-thymidine), 6.42 (m, 1H, 3'-thymidine), 6.61 (s, 6H, —O-benzyl-O-benzyl), 6.66 (s, 2H, —O-benzyl-O-benzyl), 6.82 (d, 4H, J=8.9 Hz, DMTr), 7.23-7.38 (m, 9H, DMTr), 7.60 (m, 1H, N$^6$-thymidine), 7.93 (br s, 1H, N$^3$—NH-thymidine)

Example 14

Synthesis of 5'-O-(4,4'-dimethoxytrityl)-2'-methoxyuridin-3'-yl-[3,4,5-tris(octadecyloxy)benzyl]succinate

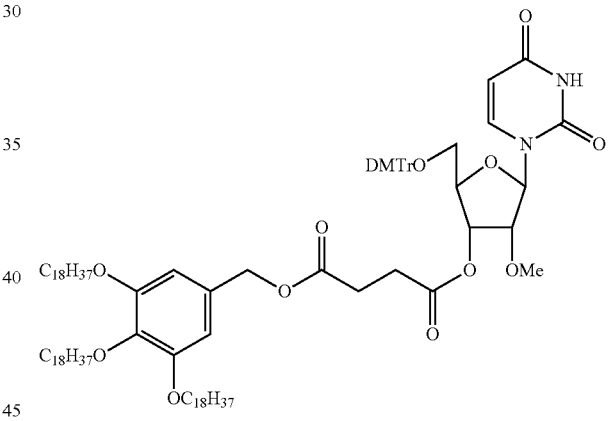

(1) Synthesis of 5'-O-(4,4'-dimethoxytrityl)-2'-s methoxyuridine-3'-O-succinate

Under an argon atmosphere, 5'-O-(4,4'-dimethoxytrityl)-2'-methoxyuridine (1.98 g, 3.57 mmol), succinic anhydride (631 mg, 6.30 mmol) and triethylamine (1.49 mL, 10.7 mmol) were dissolved in dichloromethane (30 mL), and the mixture was stirred at room temperature for 3 hr. The completion of the reaction was confirmed by thin layer chromatography, and the mixture was partition-washed three times with 2.0M phosphoric acid-triethylamine buffer (pH 7.50). The organic layer was evaporated under reduced pressure to quantitatively give a triethylamine salt (2.80 g) of the title compound as a colorless frothy solid.

(2) Synthesis of 5'-O-(4,4'-dimethoxytrityl)-2'-methoxyuridin-3'-yl-[3,4,5-tris(octadecyloxy)benzyl]succinate The compound (1.40 g, 1.84 mmol) synthesized in Example 14-(1) and 3,4,5-tris(octadecyloxy)benzyl alcohol (989 mg, 1.08 mmol) were dissolved in dehydrating dichloromethane (40 mL), 2-(1H-benzotriazol-1-yl)-1,1,3,3-tetramethyluronium hexafluorophosphate [HBTU] (2.46 g, 6.48 mmol) and N,N-diisopropylethylamine (1.13 mL, 6.48 mmol) were added, and the mixture was stirred at room temperature for 1 hr. The disappearance of the starting material was confirmed by thin layer chromatography, methanol was added to the reaction mixture, and the mixture was filtered. The obtained solid was purified by silica gel column chromatography (hexane/ethyl acetate, 1% v/v triethylamine) to give the title compound (1.41 g, 84.0%) as a white solid.

TLC: Rf=0.72 (dichloromethane:methanol=9:1)

$^1$H-NMR (400 MHz): δ 0.88 (t, 9H, J=6.6 Hz, $\underline{H}_3$C(octadecyloxy)), 1.18-1.80 (m, 102H, —C$\underline{H}_2$— (octadecyloxy)), 2.70 (m, 4H, succinyl), 3.42-3.50 (m, 1H, 5'-thymidine), 3.46 (s, 3H, 2'-OMe), 3.56-3.62 (m, 1H, 5'-thymidine), 3.79 (s, 6H, $\underline{H}_3$CO-DMTr), 3.90-4.00 (m, 6H, Bn—O—C$\underline{H}_2$—), 4.08 (m, 1H, 2'-H), 4.24 (m, 1H, 4'-H), 5.01 (s, 2H, —O—C$\underline{H}_2$-benzyl), 5.28-5.33 (m, 2H, 3'-H and N$^5$—H), 6.02 (m, 1H, 1'-H), 6.53 (s, 2H, -benzyl), 6.84 (m, 4H, DMTr), 7.24-7.38 (m, 9H, DMTr), 7.86 (d, 1H, J=8.20 Hz, N$^6$—H), 8.10 (br s, N$^3$—N$\underline{H}$)

Example 15

Synthesis of deoxycytidinyl-[3'→5']-deoxyadenylyl-[3'→5']-deoxythymidinyl-[3'→5']-deoxythymidine (5'-d[CATT]-3')

Synthesis of 5'-d[CATT]-3' using

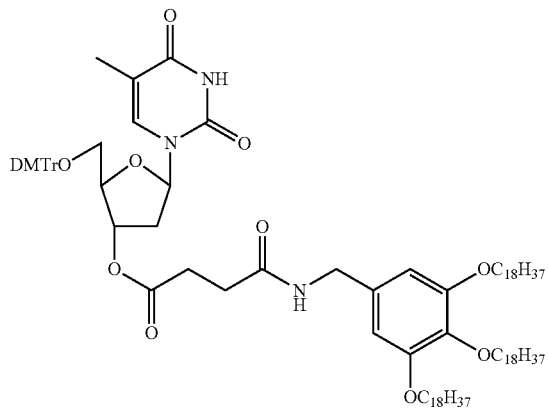

(1) Synthesis of 5'-O-(4,4'-dimethoxytrityl)deoxythymidine-3'-[O-(2-cyanoethyl)]phosphoryl-deoxythymidin-3'-yl-N-[3,4,5-tris(octadecyloxy)benzyl]succinamate The compound (302 mg, 195 μmol) synthesized in Example 6 was dissolved in dichloromethane (4.5 mL), trifluoroacetic acid (72.2 μL, 975 μmol) and pyrrole (66.9 μL, 975 μmol) were added, and the mixture was stirred for 5 min. The completion of the deprotection was confirmed by thin layer chromatography, pyridine (78.9 μL, 975 μmol) and N-methylimidazole (38.7 μL, 488 μmol) were added, and the mixture was stirred for 10 min. After neutralization, a dT-CE phosphoramidite reagent (5'-O-(4,4'-dimethoxytrityl)deoxythymidine-3'-[O-(2-cyanoethyl)-(N,N-diisopropyl)]-phosphoramidite) (435 mg, 585 μmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (5.9 mL) was added, and the mixture was stirred for 10 min. After completion of the reaction, a methanol solution saturated with sodium thiosulfate was added to the reaction mixture, and the resultant solid was collected by filtration and dried to quantitatively give the title compound (385 mg) as a white solid.

(2) Synthesis of 5'-O-(4,4'-dimethoxytrityl)-N$^6$-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[3,4,5-tris(octadecyloxy)benzyl]succinamate The compound (383 mg, 200 μmol) synthesized in Example 15-(1) was dissolved in dichloromethane (4.5 mL), trifluoroacetic acid (72.2 μL, 975 μmol) and pyrrole (66.9 μL, 975 μmol) were added, and the mixture was stirred for 5 min. The completion of the deprotection was confirmed by thin layer chromatography, pyridine (78.9 μL, 975 μmol) and N-methylimidazole (38.7 μL, 488 μmol) were added, and the mixture was stirred for 10 min. After neutralization, a dA-CE phosphoramidite reagent (5'-O-(4,4'-dimethoxytrityl)-N$^6$-benzoyl-2'-deoxyadenosine-3'-[O-(2-cyanoethyl)-(N,N-diisopropyl)]-phosphoramidite) (514 mg, 600 μmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (5.9 mL) was added, and the mixture was stirred for 10 min. After completion of the reaction, a methanol solution saturated with sodium thiosulfate was added to the reaction mixture, and the resultant solid was collected by filtration and dried to give the title compound (479 mg, 99.8%) as a white solid.

(3) Synthesis of 5'-O-(4,4'-dimethoxytrityl)-N$^4$-benzoyl-2'-deoxycytidine-3'-[O-(2-cyanoethyl)]phosphoryl-N$^6$-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[3,4,5-tris(octadecyloxy)benzyl]succinamate The compound (476 mg, 198 μmol) synthesized in Example 15-(2) was dissolved in dichloromethane (4.5 mL), trifluoroacetic acid (72.2 μL, 975 μmol) and pyrrole (66.9 μL, 975 μmol) were added, and the mixture was stirred for 5 min. The completion of the deprotection was confirmed by thin layer chromatography, pyridine (78.9 μL, 975 μmol) and N-methylimidazole (38.7 μl, 488 μmol) were added, and the mixture was stirred for 10 min. After neutralization, a dC-CE phosphoramidite reagent (5'-O-(4,4'-dimethoxytrityl)-N$^4$-benzoyl-2'-deoxycytidine-3'-[O-(2-cyanoethyl)-(N,N-diisopropyl)]-phosphoramidite) (500 mg, 600 μmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (5.9 mL) was added, and the mixture was stirred for 10 min. After completion of the reaction, a methanol solution saturated with sodium thiosulfate was added to the reaction mixture, and the resultant solid was collected by filtration and dried to give the title compound (522 mg, 91.9%) as a white solid.

(4) Synthesis of deoxycytidinyl-[3'→5']-deoxyadenylyl-[3'→5']-deoxythymidinyl-[3'→5']-deoxythymidine (5'-d[CATT]-3')

The compound synthesized in Example 15-(3) and a solution (4.0 mL) of 28% aqueous ammonia solution:ethanol=3:1 were placed in an autoclave, and the mixture was heated at 65° C. for 16 hr. The reaction mixture was concentrated by a centrifugal evaporator under reduced pressure. The mixture was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z (MALDI TOF): Anal. Calc. for $C_{39}H_{51}N_{12}O_{23}P_3$: 1148.2. Found 1147.0 (M−H)⁻

Example 16

Synthesis of deoxycytidinyl-[3'→5']-deoxyadenylyl-[3'→5']-deoxythymidinyl-(3'→5')-deoxythymidine (5'-d[CATT]-3')

Synthesis of 5'-d[CATT]-3' using

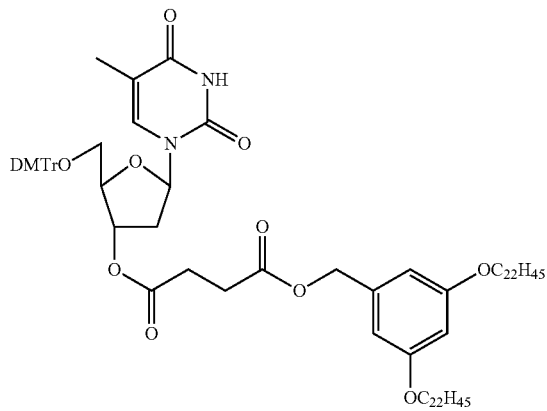

(1) Synthesis of 5'-O-(4,4'-dimethoxytrityl)-deoxythymidine-3'-[O-(2-cyanoethyl)]phosphoryl-deoxythymidin-3'-yl-(3,5-bis(docosyloxy)benzyl)succinate The compound (202 mg, 146 μmol) synthesized in Example 7 was dissolved in dichloromethane (3.0 mL), trifluoroacetic acid (53.5 μL, 723 μmol) and pyrrole (50.0 μL, 723 μmol) were added, and the mixture was stirred for 5 min. The completion of the deprotection was confirmed by thin layer chromatography, pyridine (58.4 μL, 723 μmol) and N-methylimidazole (28.6 μL, 361 μmol) were added, and the mixture was stirred for 10 min. After neutralization, a dT-CE phosphoramidite reagent (208 mg, 289 μmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.9 mL) was added, and the mixture was stirred for 10 min. After completion of the reaction, a methanol solution saturated with sodium thiosulfate was added to the reaction mixture, and the resultant solid was collected by filtration and dried to give the title compound (226 mg, 89.0%) as a white solid.

(2) Synthesis of 5'-O-(4,4'-dimethoxytrityl)-N⁶-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-[3,5-bis(docosyloxy)benzyl]succinate The compound (225 mg, 129 μmol) synthesized in Example 16-(1) was dissolved in dichloromethane (3.0 mL), trifluoroacetic acid (47.8 μL, 645 μmol) and pyrrole (44.6 μL, 645 μmol) were added, and the mixture was stirred for 5 min. The completion of the deprotection was confirmed by thin layer chromatography, pyridine (52.1 μL, 645 μmol) and N-methylimidazole (25.6 μL, 323 μmol) were added, and the mixture was stirred for 10 min. After neutralization, a dA-CE phosphoramidite reagent (334 mg, 387 μmol) dissolved in 0.25 mol/L 5-(benzylthio)-1H-tetrazole/acetonitrile solution (1.0 ml) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to quantitatively give the title compound (288 mg) as a white solid.

(3) Synthesis of 5'-O-(4,4'-dimethoxytrityl)-N⁴-benzoyl-2'-deoxycytidine-3'-[O-(2-cyanoethyl)]phosphoryl-N⁶-benzoyl-2'-deoxyadenosine-3'-[O-(2-cyanoethyl)]phosphoryl-deoxythymidine-3'-[O-(2-cyanoethyl)]-phosphoryl-deoxythymidin-3'-yl-[3,5-bis(docosyloxy)benzyl]succinate The compound (287 mg, 129 μmol) synthesized in Example 16-(2) was dissolved in dichloromethane (3.0 mL), trifluoroacetic acid (47.8 μl, 645 μmol) and pyrrole (44.6 μl, 645 μmol) were added, and the mixture was stirred for 5 min. The completion of the deprotection was confirmed by thin layer chromatography, pyridine (52.1 μL, 645 μmol) and N-methylimidazole (25.6 μL, 323 μmol) were added, and the mixture was stirred for 10 min. After neutralization, a dC-CE phosphoramidite reagent (325 mg, 387 μmol) dissolved in 0.25 mol/L 5-(benzylthio)-1H-tetrazole/acetonitrile solution (1.0 ml) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (316 mg, 91.2%) as a white solid.

(4) Synthesis of deoxycytidinyl-[3'→5']-deoxyadenylyl-[3'→5']-deoxythymidinyl-[3'→5']-deoxythymidine (5'-d[CATT]-3')

The compound synthesized in Example 16-(3) and a solution (4.0 mL) of 28% aqueous ammonia solution:ethanol=3:1 were placed in an autoclave, the mixture was heated at 65° C. for 16 hr, and concentrated by a centrifugal evaporator under reduced pressure. The concentrated solution was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z (MALDI TOF): Anal. Calc. for $C_{39}H_{51}N_{12}O_{23}P_3$: 1148.2. Found 1147.0 (M−H)⁻

Example 17

Synthesis of deoxycytidinyl-[3'→5']-deoxyadenylyl-[3'→5']-deoxythymidinyl-[3'→5']-deoxythymidine (5'-d[CATT]-3')

Synthesis of 5'-d[CATT]-3' using

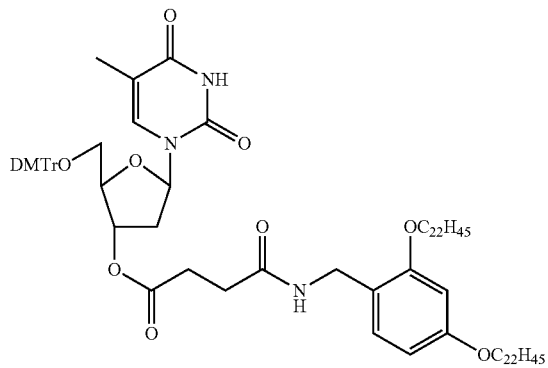

(1) Synthesis of 5'-O-(4,4'-dimethoxytrityl)-deoxythymidine-3'-[O-(2-cyanoethyl)]phosphoryl-deoxythymidin-3'-yl-N-[2,4-bis(docosyloxy)benzyl]succinamate The compound (197 mg, 143 µmol) synthesized in Example 10 was dissolved in dichloromethane (3.0 mL) under an argon atmosphere, trifluoroacetic acid (53.5 µL, 720 µmol) and pyrrole (50.0 µL, 720 µmol) were added, and the mixture was stirred for 5 min. The completion of the deprotection was confirmed by thin layer chromatography, pyridine (58.4 µL, 720 µmol) and N-methylimidazole (28.6 µL, 360 µmol) were added, and the mixture was stirred for 10 min. After neutralization, a dT-CE phosphoramidite reagent (201 mg, 289 µmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.9 mL) was added, and the mixture was stirred for 10 min. After completion of the reaction, a methanol solution saturated with sodium thiosulfate was added to the reaction mixture, and the resultant solid was collected by filtration and dried to give the title compound (248 mg, 99.9%) as a white solid.

(2) Synthesis of 5'-O-(4,4'-dimethoxytrityl)-N⁶-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[2,4-bis(docosyloxy)benzyl]succinamate The compound (235 mg, 135 µmol) synthesized in Example 17-(1) was dissolved in dichloromethane (3.0 mL) under an argon atmosphere, trifluoroacetic acid (53.5 µL, 720 µmol) and pyrrole (50.0 µL, 720 µmol) were added, and the mixture was stirred for 5 min. The completion of the deprotection was confirmed by thin layer chromatography, pyridine (58.4 µL, 720 µmol) and N-methylimidazole (28.6 µL, 360 µmol) were added, and the mixture was stirred for 10 min. After neutralization, a dA-CE phosphoramidite reagent (347 mg, 405 µmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (276 mg, 91.9%) as a white solid.

(3) Synthesis of 5'-O-(4,4'-dimethoxytrityl)-N⁴-benzoyl-2'-deoxycytidine-3'-[O-(2-cyanoethyl)]phosphoryl-N⁶-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[2,4-bis(docosyloxy)benzyl]succinamate The compound (253 mg, 94.2 µmol) synthesized in Example 17-(2) was dissolved in dichloromethane (3.0 mL) under an argon atmosphere, trifluoroacetic acid (34.9 µL, 471 µmol) and pyrrole (32.6 µL, 471 µmol) were added, and the mixture was stirred for 5 min. The completion of the deprotection was confirmed by thin layer chromatography, pyridine (38.1 µL, 471% µmol) and N-methylimidazole (18.7 µL, 235 µmol) were added, and the mixture was stirred for 10 min. After neutralization, a dC-CE phosphoramidite reagent (236 mg, 282 µmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (252 mg, 99.5%) as a white solid.

(4) Synthesis of deoxycytidinyl-[3'→5']-deoxyadenylyl-[3'→5']-deoxythymidinyl-[3'→5']-deoxythymidine (5'-d[CATT]-3')

The compound synthesized in Example 17-(3) and a solution (4.0 mL) of 28% aqueous ammonia solution:ethanol=3:1 were placed in an autoclave, the mixture was heated at 65° C. for 16 hr, and concentrated by a centrifugal evaporator under reduced pressure. The concentrated solution was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z (MALDI TOF): Anal. Calc. for $C_{39}H_{51}N_{12}O_{23}P_3$: 1148.24. Found 1149.63 (M+H)⁺

Example 18

Synthesis of deoxycytidinyl-[3'→5']-deoxyadenylyl-[3'→5']-deoxythymidinyl-[3'→5']-deoxythymidine (5'-d[CATT]-3')

Synthesis of 5'-d[CATT]-3' using

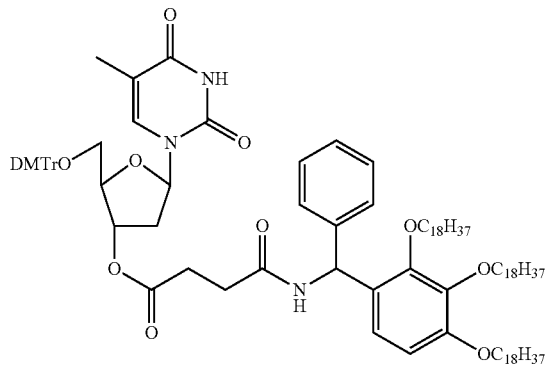

(1) Synthesis of 5'-O-(4,4'-dimethoxytrityl)-deoxythymidine-3'-[O-(2-cyanoethyl)]phosphoryl-deoxythymidin-3'-yl-N-[2,3,4-tris(octadecyloxy)benzhydryl]succinamate The compound (401 mg, 246 μmol) synthesized in Example 12 was dissolved in dichloromethane (3.0 mL) under an argon atmosphere, trifluoroacetic acid (91.0 μl, 1.23 mmol) and pyrrole (85.0 μL, 1.23 mmol) were added, and the mixture was stirred for 5 min. The completion of the deprotection was confirmed by thin layer chromatography, pyridine (99.5 μL, 1.23 mmol) and N-methylimidazole (48.8 μl, 615 μmol) were added, and the mixture was stirred for 10 min. After neutralization, a dT-CE phosphoramidite reagent (373 mg, 492 μmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (4.9 mL) was added, and the mixture was stirred for 10 min. After completion of the reaction, a methanol solution saturated with sodium thiosulfate was added to the reaction mixture, and the resultant solid was collected by filtration and dried to give the title compound (491 mg, 95.7%) as a white solid.

(2) Synthesis of 5'-O-(4,4'-dimethoxytrityl)-$N^6$-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[2,3,4-tris(octadecyloxy)benzhydryl]succinamate The compound (228 mg, 115 μmol) synthesized in Example 18-(1) was dissolved in dichloromethane (3.0 mL) under an argon atmosphere, trifluoroacetic acid (42.6 μL, 575 μmol) and pyrrole (39.8 μL, 575 μmol) were added, and the mixture was stirred for 5 min. The completion of the deprotection was confirmed by thin layer chromatography, pyridine (46.5 μL, 575 μmol) and N-methylimidazole (22.9 μL, 288 μmol) were added, and the mixture was stirred for 10 min. After neutralization, a dA-CE phosphoramidite reagent (296 mg, 345 μmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.9 ml) was added, and the mixture was stirred for 10 min. After completion of the reaction, a methanol solution saturated with sodium thiosulfate was added to the reaction mixture, and the resultant solid was collected by filtration and dried to give the title compound (269 mg, 94.1%) as a white solid.

(3) Synthesis of 5'-O-(4,4'-dimethoxytrityl)-$N^4$-benzoyl-2'-deoxycytidine-3'-[O-(2-cyanoethyl)]phosphoryl-$N^6$-benzoyl-2'-deoxyadenosine-3'-[O-(2-cyanoethyl)]phosphoryl-deoxythymidine-3'-[O-(2-cyanoethyl)]phosphoryl-deoxythymidin-3'-yl-N-[2,3,4-tris(octadecyloxy)benzhydryl]succinamate The compound (254 mg, 102 μmol) synthesized in Example 18-(2) was dissolved in dichloromethane (3.0 mL) under an argon atmosphere, trifluoroacetic acid (37.8 μL, 510 μmol) and pyrrole (35.3 μL, 510 μmol) were added, and the mixture was stirred for 5 min. The completion of the deprotection was confirmed by thin layer chromatography, pyridine (41.2 μL, 510 μmol) and N-methylimidazole (20.2 μL, 255 μmol) were added, and the mixture was stirred for 10 min. After neutralization, a dC-CE phosphoramidite reagent (254 mg, 306 μmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.1 mL) was added, and the mixture was stirred for 10 min. After completion of the reaction, a methanol solution saturated with sodium thiosulfate was added to the reaction mixture, and the resultant solid was collected by filtration and dried to give the title compound (293 mg, 97.3%) as a white solid.

(4) Synthesis of deoxycytidinyl-[3'→5']-deoxyadenylyl-[3'→5']-deoxythymidinyl-[3'→5']-deoxythymidine (5'-d[CATT]-3')

The compound synthesized in Example 18-(3) and a solution (4.0 mL) of 28% aqueous ammonia solution:ethanol=3:1 were placed in an autoclave, the mixture was heated at 65° C. for 16 hr, and concentrated by a centrifugal evaporator under reduced pressure. The concentrated solution was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z (MALDI TOF): Anal. Calc. for $C_{39}H_{51}N_{12}O_{23}P_3$: 1148.24. Found 1146.8 (M−H)$^-$

Example 19

Synthesis of 5'-O-(4,4'-dimethoxytrityl)-2'-fluorouridine-3'-[O-(2-cyanoethyl)]phosphoryl-deoxythymidin-3'-yl-[3,4,5-tris(octadecyloxy)benzyl]succinate

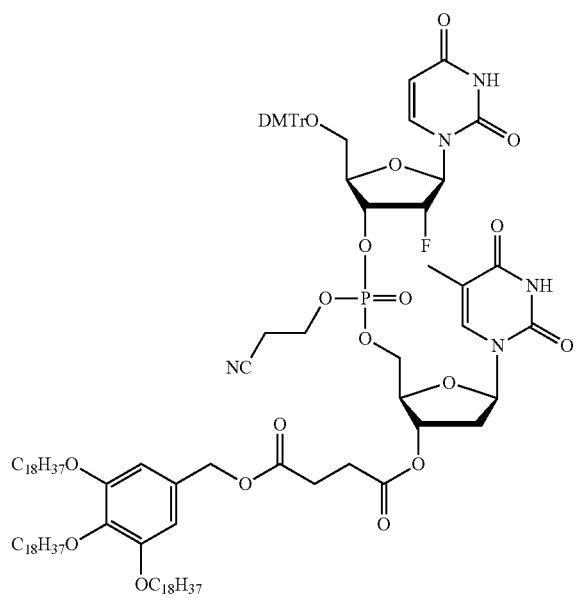

5'-O-(4,4'-dimethoxytrityl)-deoxythymidin-3'-yl-[3,4,5-tris(octadecyloxy)benzyl]succinate (214 mg, 138 μmol) was dissolved in dichloromethane (3.0 mL) under an argon atmosphere, trifluoroacetic acid (96.3 μL, 1.38 mmol) and pyrrole (90.0 μL, 1.38 mmol) were added, and the mixture was stirred for 5 min. The completion of the deprotection was confirmed by thin layer chromatography, pyridine (105 μL, 1.38 mmol) and N-methylimidazole (51.6 μL, 690 μmol) were added, and the mixture was stirred for 10 min. After neutralization, a 2'-F-U-CE phosphoramidite reagent (5'-O-(4,4'-dimethoxytrityl)-2'-fluorouridine-3'-[O-(2-cyanoethyl)-(N,N-diisopropyl)]-phosphoramidite) (390 mg, 520 μmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (243 mg, 93.2%) as a white solid.

m/z (ESI-MS): Anal. Calc. for $C_{108}H_{163}FN_5O_{20}P$: 1900.16. Found 1919.19 $(M+NH_4)^+$

Example 20

Synthesis of 5'-O-(4,4'-dimethoxytrityl)-2'-methoxyuridine-3'-[O-(2-cyanoethyl)]phosphoryl-2'-methoxyuridin-3'-yl-[3,4,5-tris(octadecyloxy)benzyl]succinate

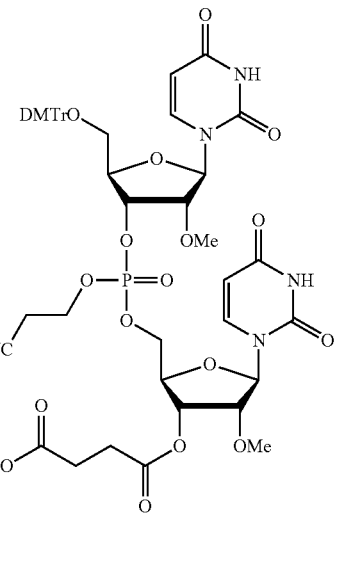

5'-O-(4,4'-dimethoxytrityl)-2'-methoxyuridin-3'-yl-[3,4,5-tris(octadecyloxy)benzyl]succinate (202 mg, 129 μmol) was dissolved in dichloromethane (3.0 mL) under an argon atmosphere, trifluoroacetic acid (96.3 μL, 1.38 mmol) and pyrrole (90.0 μL, 1.38 mmol) were added, and the mixture was stirred for 5 min. The completion of the deprotection was confirmed by thin layer chromatography, pyridine (105 μL, 1.38 mmol) and N-methylimidazole (51.6 μL, 690 μmol) were added, and the mixture was stirred for 10 min. After neutralization, a 2'-OMe-U-CE phosphoramidite reagent (5'-O-(4,4'-dimethoxytrityl)-2'-methoxyuridine-3'-[O-(2-cyanoethyl)-(N,N-diisopropyl)]-phosphoramidite) (402 mg, 528 μmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (237 mg, 95.7%) as a white solid.

m/z (ESI-MS): Anal. Calc. for $C_{109}H_{166}N_5O_{22}P$: 1929.48. Found 1947.21 $(M+NH_4)$

Example 21

Synthesis of 5'-O-(4,4'-dimethoxytrityl)-2'-fluorouridine-3'-[O-(2-cyanoethyl)]phosphoryl-2'-methoxyuridin-3'-yl-[3,4,5-tris(octadecyloxy)benzyl]succinate

Example 22

Synthesis of 5'-O-(4,4'-dimethoxytrityl)-2'-methoxyuridine-3'-[O-(2-cyanoethyl)]phosphoryl-deoxythymidin-3'-yl-[3,4,5-tris(octadecyloxy)benzyl]succinate

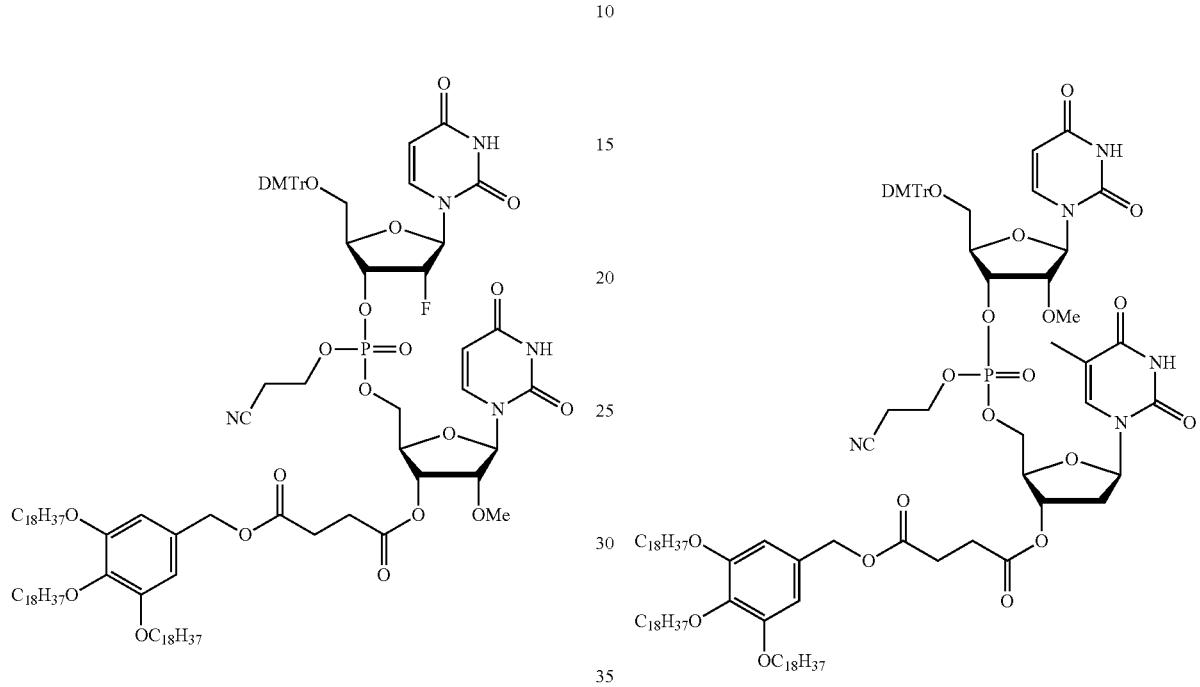

5'-O-(4,4'-Dimethoxytrityl)-2'-methoxyuridin-3'-yl-[3,4,5-tris(octadecyloxy)benzyl]succinate (197 mg, 127 µmol) was dissolved in dichloromethane (3.0 mL) under an argon atmosphere, trifluoroacetic acid (96.3 µL, 1.38 mmol) and pyrrole (90.0 µL, 1.38 mmol) were added, and the mixture was stirred for 5 min. The completion of the deprotection was confirmed by thin layer chromatography, pyridine (105 µL, 1.38 mmol) and N-methylimidazole (51.6 µL, 690 µmol) were added, and the mixture was stirred for 10 min. After neutralization, a 2'-F-U-CE phosphoramidite reagent (404 mg, 539 µmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (228 mg, 94.7%) as a white solid.

m/z (ESI-MS): Anal. Calc. for $C_{108}H_{163}FN_5O_{21}P$: 1917.44. Found 1935.18 (M+NH$_4$)+

5'-O-(4,4'-Dimethoxytrityl)-deoxythymidin-3'-yl-[3,4,5-tris(octadecyloxy)benzyl]succinate (214 mg, 138 µmol) was dissolved in dichloromethane (3.0 mL) under an argon atmosphere, trifluoroacetic acid (96.3 µL, 1.38 mmol) and pyrrole (90.0 µL, 1.38 mmol) were added, and the mixture was stirred for 5 min. The completion of the deprotection was confirmed by thin layer chromatography, pyridine (105 µL, 1.38 mmol) and N-methylimidazole (51.6 µL, 690 µmol) were added, and the mixture was stirred for 10 min. After neutralization, a 2'-OMe-U-CE phosphoramidite reagent (396 mg, 520 µmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (3.9 mL) was added, and the mixture was stirred for 10 min. After completion of the reaction, a methanol solution saturated with sodium thiosulfate was added to the reaction mixture, and the resultant solid was collected by filtration and dried to give the title compound (246 mg, 94.0%) as a white solid.

m/z (ESI-MS): Anal. Calc. for $C_{109}H_{166}N_5O_{21}P$: 1912.18. Found 1931.21 (M+NH$_4$)$^+$

Example 23

One Pot Reaction Using 2,4,6-Trimethylpyridine as Neutralization Base

Synthesis of 5'-O-(4,4'-dimethoxytrityl)-deoxythymidine-3'-[O-(2-cyanoethyl)]phosphoryl-deoxythymidin-3'-yl-[3,4,5-tris(octadecyloxy)benzyl]succinate Under an argon atmosphere, 5'-O-(4,4'-dimethoxytrityl)-deoxythymidin-3'-yl-[3,4,5-tris(octadecyloxy)benzyl]succinate (200 mg, 130 µmol) was dissolved in dichloromethane (3.0 mL), trifluoroacetic acid (96.3 µL, 1.30 mmol) and pyrrole (90.0 µL, 1.30 mmol) were added, and the mixture was stirred for 5 min. The completion of the deprotection was confirmed by thin layer chromatography, 2,4,6-trimethylpyridine (171 µL, 1.30 mmol) and N-methylimidazole (48.6 µL, 650 µmol) were added, and the mixture was stirred for 10 min. After neutralization, a dT-CE phosphoramidite reagent (193 mg, 260 µmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.6 mL) was added, and the mixture was stirred for 10 min. After m completion of the reaction, a methanol solution saturated with sodium thiosulfate was added to the reaction mixture, and the resultant solid was collected by filtration and dried to give the title compound (241 mg, 96.9%) as a white solid.

m/z (ESI-MS): Anal. Calc. for $C_{109}H_{166}N_5O_{20}P$: 1896.19. Found 1915.23 $(M+NH_4)^+$

Example 24

One Pot Reaction Using Trifluoromethanesulfonic Acid as Deprotection Reagent and Benzimidazole as Neutralization Reagent Synthesis of 5'-O-(4,4'-dimethoxytrityl)-deoxythymidine-3'-[O-(2-cyanoethyl)]phosphoryl-deoxythymidin-3'-yl-[3,4,5-tris(octadecyloxy)benzyl]succinate Under an argon atmosphere, 5'-O-(4,4'-dimethoxytrityl)-deoxythymidin-3'-yl-[3,4,5-tris(octadecyloxy)benzyl]succinate (200 mg, 130 µmol) was dissolved in dichloromethane (3.0 mL), trifluoromethanesulfonic acid (5.75 µL, 65.0 µmol) and pyrrole (90.0 µL, 1.30 mmol) were added, and the mixture was stirred for 5 min. The completion of the deprotection was confirmed by thin layer chromatography, benzimidazole (7.68 mg, 65.0 µmol) was added, and the mixture was stirred for 10 min. After neutralization, a dT-CE phosphoramidite reagent (193 mg, 260 µmol) dissolved in 0.25 mol/L 5-(benzylthio)-1H-tetrazole/acetonitrile solution (1.0 mL) was added to the reaction mixture, and the mixture was stirred for 10 min. 0.2 mol/L Iodine pyridine/tetrahydrofuran/water=49/49/2 solution (2.6 mL) was added, and the mixture was stirred for 10 min. After completion of the reaction, a methanol solution saturated with sodium thiosulfate was added to the reaction mixture, and the resultant solid was collected by filtration and dried to give the title compound (248 mg, 98.6%) as a white solid.

m/z (ESI-MS): Anal. Calc. for $C_{109}H_{166}N_5O_{20}P$: 1896.19. Found 1915.23 $(M+NH_4)^+$

Example 25

One Pot Reaction Using 90% Aqueous Acetonitrile Solution as Precipitation Solvent Synthesis of 5'-O-(4,4'-dimethoxytrityl)-deoxythymidine-3'-[O-(2-cyanoethyl)]phosphoryl-deoxythymidin-3'-yl-[3,4,5-tris(octadecyloxy)benzyl]succinate Under an argon atmosphere, 5'-O-(4,4'-dimethoxytrityl)-deoxythymidin-3'-yl-[3,4,5-tris(octadecyloxy)benzyl]succinate (200 mg, 130 µmol) was dissolved in dichloromethane (3.0 mL), trifluoroacetic acid (96.3 µL, 1.30 mmol) and pyrrole (90.0 µL, 1.30 mmol) were added, and the mixture was stirred for 5 min. The completion of the deprotection was confirmed by thin layer chromatography, pyridine (105 µL, 1.30 mmol) and N-methylimidazole (51.6 µL, 650 µmol) were added, and the mixture was stirred for 10 min. After neutralization, a dT-CE phosphoramidite reagent (193 mg, 260 µmol) dissolved in 0.25 mol/L 5-(benzylthio)-1H-tetrazole/acetonitrile solution (1.5 mL) was added to the reaction mixture, and the mixture was stirred for 10 min. 0.2 mol/L Iodine pyridine/tetrahydrofuran/water=49/49/2 solution (2.6 mL) was added, and the mixture was stirred for 10 min. After completion of the reaction, a 90% aqueous acetonitrile solution saturated with sodium thiosulfate was added to the reaction mixture, and the resultant solid was collected by filtration and dried to give the title compound (248 mg, 99.6%) as a white solid.

m/z (ESI-MS): Anal. Calc. for $C_{109}H_{166}N_5O_{20}P$: 1896.19. Found 1915.22 $(M+NH_4)^+$

INDUSTRIAL APPLICABILITY

The present invention provides a method of producing an n+p-mer oligonucleotide efficiently in a high yield, which includes use of, as a starting material, an n-mer oligonucleotide wherein the 3'-terminal hydroxyl group is protected by a pseudo solid phase protecting group, and the 5'-terminal hydroxyl group is protected by a temporary protecting group, and (1) a deprotection step of the 5'-terminal hydroxyl group protected by a temporary protecting group, (2) a 5'-terminal elongation step by the addition of a p-mer oligonucleotide wherein the 3'-position is phosphoramidited, and (3) an oxidation step or a sulfurization step of a phosphite triester moiety, by adding a particular cation scavenger during the deprotection step of a 5'-terminal hydroxyl group protected by a temporary protecting group, applying a neutralization treatment after completion of the deprotection reaction, and using a particular oxidizing agent or sulfurizing agent in the oxidation step or sulfurization step, and the present invention further provides RNA, DNA, nucleic acid medicine and the like. In addition, an oligonucleotide automatic synthesis program and an oligonucleotide automatic synthesis apparatus, which utilize the production method of oligonucleotide of the present invention can also be developed.

According to "GENOME CHEMISTRY" SEKINE, Mitsuo and SAITO, Isao ed., Kodansha Scientific, 1-3 (2003)", a general phosphoramidite method is known to include the following as a basic unit.

STEP1: deprotection step (removal of 5' hydroxyl-protecting group of chain elongation resultant product), STEP2: condensation step (step of condensing nucleoside-3'-phosphoramidite wherein various functional groups are protected and protected nucleotide), STEP3: capping step (step of capping unreacted 5'-hydroxyl group), and STEP4: oxidation step (step of obtaining nucleoside phosphate triester compound by oxidation).

When the "improved continuous phosphoramidite method" is defined as "a method comprising (STEP 1) deprotection step, (STEP 2) condensation step and (STEP 4) oxidation step as a basic unit, which continuously performs STEPs 1, 2, 4 in a solution, without an isolation and purification step after STEPs 1, 2", the production method of oligonucleotide of the present invention can also be defined as follows.

[1] A production method of oligonucleotide by an improved continuous phosphoramidite method, comprising at least one kind of cation scavenger selected from a pyrrole derivative and an indole derivative in a deprotection step.

[2] The production method of [1], further comprising an organic base after the deprotection step and before a condensation step.

[3] The production method of [1] or [2], further comprising using an oxidizing agent or a sulfurizing agent in the oxidation step.

[4] The production method of any one of [1] to [3], further comprising crystallization and isolation of the oxidized compound or sulfurated compound in a polar solvent after the oxidation step.

[5] The production method of [4], further comprising deprotection of all protecting groups.

Thus, it is highly significant that the co-presence of at least one kind of cation scavenger selected from a pyrrole derivative and an indole derivative affords an improved continuous phosphoramidite method that does not require an isolation and purification step after STEPs 1 and 2, or a capping step.

This application is based on patent application No. 2011-110872 filed in Japan and US provisional application No. 61/486,949, the contents of which are incorporated in full herein.

Although the present invention have been presented or described by referring to preferred embodiments of this invention, it will, however, be understood by those of ordinary skill in the art that various modifications may be made to the forms and details without departing from the scope of the invention as set forth in the appended claims. Accordingly, all such modifications are intended to be included within the scope of this invention.

All patents, patent publications and other publications identified or referenced herein are incorporated in full herein by this reference in their entireties.

We claim:

1. A method of producing an oligonucleotide, comprising:
   reacting, in a non-polar solvent:
   (a) an n-mer oligonucleotide, wherein n is an integer of one or more, wherein the n-mer oligonucleotide has a 3'-hydroxyl group protected by a solubilizing protecting group and a 5'-hydroxyl group protected by a temporary protecting group removable under an acidic condition,
   (b) an acid, and
   (c) at least one kind of cation scavenger selected from the group consisting of a pyrrole derivative and an indole derivative,
   to remove said temporary protecting group of said 5'-hydroxyl group, to obtain a reaction mixture;
   neutralizing said reaction mixture with an organic base, to obtain a neutralized reaction mixture comprising an n-mer oligonucleotide in which the temporary protecting group at the 5'-hydroxyl group has been removed;
   mixing with said neutralized reaction mixture a p-mer oligonucleotide, wherein p is an integer of one or more, wherein the p-mer oligonucleotide has a 3'-hydroxyl group phosphoramidited and a 5'-hydroxyl group protected by a temporary protecting group removable under an acidic condition,
   such that a phosphite triester group is formed via the 5'-hydroxyl group of the n-mer oligonucleotide and the p-mer oligonucleotide is condensed with said n-mer oligonucleotide in which the temporary protecting group of the 5'-hydroxyl group has been removed to obtain a reaction mixture including a protected precursor of a n+p-mer oligonucleotide;
   mixing an oxidizing agent or a sulfurizing agent with said reaction mixture including the protected precursor to convert the phosphite triester group of said protected precursor to a phosphate triester group or a thiophosphate triester group;
   precipitating the protected precursor from the reaction mixture;
   separating the protected precursor that has been precipitated; and
   removing all of the protecting groups in the protected precursor.

2. A method according to claim 1, wherein p is 1.

3. A method according to claim 1, wherein the precipitating comprises mixing a polar solvent with the reaction mixture including the protected precursor, and the separating comprises performing solid-liquid separation.

4. A method according to claim 3, wherein the removing comprises performing at least one of an acid treatment, an alkali treatment and a catalytic reduction.

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 1
tcccgcctgt gacatgcatt          20

5. A method according to claim 1, wherein said temporary protecting group is a dimethoxytrityl group or a monomethoxytrityl group.

6. A method according to claim 1, wherein said non-polar solvent is a solvent selected from the group consisting of a halogenated solvent, an aromatic solvent, an ester solvent, an aliphatic solvent, a non-polar ether solvent, and a mixture thereof.

7. A method according to claim 1, wherein said non-polar solvent is a solvent selected from the group consisting of dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and a mixture thereof.

8. A method according to claim 3, wherein said polar solvent is an alcohol solvent or a nitrile solvent.

9. A method according to claim 3, wherein said polar solvent is methanol or acetonitrile.

10. A method according to claim 1, wherein said pyrrole derivative or said indole derivative is at least one member selected from the group consisting of pyrrole, 3-methylpyrrole, 2,4-dimethylpyrrole, indole, 4-methylindole, 5-methylindole, 6-methylindole, 7-methylindole, 5,6-dimethylindole, and 6,7-dimethylindole.

11. A method according to claim 1, wherein said oxidizing agent is iodine, (1S)-(+)-(10-camphorsulfonyl)oxaziridine, tert-butyl hydroperoxide, 2-butanone peroxide, 1,1-dihydroperoxycyclododecane, bis(trimethylsilyl)peroxide, or m-chloroperbenzoic acid.

12. A method according to claim 1, wherein said sulfurizing agent is 3-((N,N-dimethylaminomethylidene)amino)-3H-1,2,4-dithiazole-5-thione, 3H-1,2-benzodithiol-3-one-1,1-dioxide, 3H-1,2-benzodithiol-3-one, phenylacetyl disulfide, tetraethylthiuram disulfide, 3-amino-1,2,4-dithiazole-5-thione, or sulfur.

13. A method according to claim 1, wherein said acid is trifluoroacetic acid, dichloroacetic acid, trifluoromethanesulfonic acid, trichloroacetic acid, methanesulfonic acid, hydrochloric acid, acetic acid, or p-toluenesulfonic acid.

14. A method according to claim 1, wherein said organic base is at least one member selected from the group consisting of pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole, and 5-nitrobenzimidazole.

15. A method of producing an oligonucleotide by a continuous phosphoramidite method, comprising conducting at least one deprotection step in the presence of at least one cation scavenger selected from a pyrrole derivative and an indole derivative.

16. A solubilizing protecting group represented by formula (I):

wherein
L is a group represented by formula (a1):

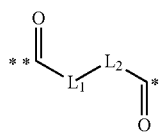

wherein * indicates the bonding position to Y;
** indicates the bonding position to a group to be protected;

$L_1$ is an unsubstituted or substituted divalent $C_{1-22}$ hydrocarbon group; and $L_2$ is a single bond, or a group represented by C(=O)N(R$^2$)—R$^1$—N(R$^3$)* wherein  indicated the bonding position to $L_1$, * indicates the bonding position to C=O, $R^1$ is an unsubstituted or substituted $C_{1-22}$ alkylene group, and $R^2$ and $R^3$ are each independently a hydrogen atom or an unsubstituted or substituted $C_{1-22}$ alkyl group, or $R^2$ and $R^3$ are optionally joined to form an unsubstituted or substituted $C_{1-22}$ alkylene ring, Y is an oxygen atom or NR wherein R is a hydrogen atom, an alkyl group or an aralkyl group, and Z is a group represented by formula (a2):

wherein * indicates the bonding position to Y;

$R^4$ is a hydrogen atom, or when $R_b$ is a group represented by formula (a3), $R^4$ is optionally a single bond or —O— in combination with $R^6$ to form a fluorenyl group or a xanthenyl group together with ring B;

each $R^5$ in the number of k is independently an organic group having an aliphatic hydrocarbon group having 10 to 40 carbon atoms;

k is an integer of 1 to 4;

ring A optionally further has, in addition to $OR^5$ in the number of k, one or more substituents selected from the group consisting of a halogen atom, a $C_{1-6}$ alkyl group optionally substituted by a halogen atom, and a $C_{1-6}$ alkoxy group optionally substituted by a halogen atom;

$R_a$ is a hydrogen atom; and $R_b$ is a hydrogen atom, or a group represented by formula (a3):

wherein * indicates a bonding position;

j is an integer of 0 to 4;

each $R^7$ in the number of j is independently an organic group having an aliphatic hydrocarbon group having 10 to 40 carbon atoms;

$R^6$ is a hydrogen atom, or optionally a single bond or —O— in combination with $R^4$ to form a fluorenyl group or a xanthenyl group together with ring A; and ring B optionally further has, in addition to $OR^7$ in the number of j, one or more substituents selected from the group consisting of a halogen atom, a $C_{1-6}$ alkyl group optionally substituted by a halogen atom, and a $C_{1-6}$ alkoxy group optionally substituted by a halogen atom.

17. A nucleotide represented by formula (II):

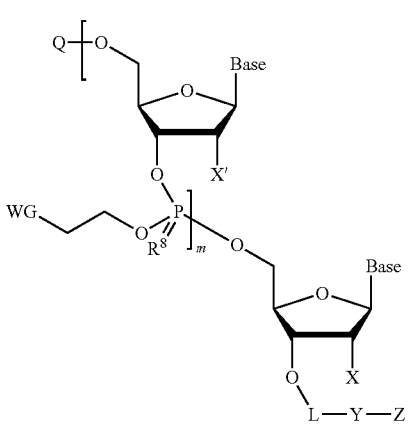

wherein m is an integer of 0 to 49,

Base in the number of m+1 are each independently an optionally protected nucleic acid base, Q is a hydrogen atom, or a temporary protecting group removable under acidic conditions, X is a hydrogen atom, a halogen atom, or an optionally protected hydroxyl group, X' in the number of m are each independently a hydrogen atom, a halogen atom, or an optionally protected hydroxyl group, $R^8$ in the number of m are each independently an oxygen atom or a sulfur atom, WG in the number of m are each independently an electron-withdrawing group, L is a group represented by formula (a1):

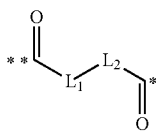

wherein * indicates the bonding position to Y;

** indicates the bonding position to a 3'-hydroxy group of the nucleotide;

$L_1$ is an optionally substituted divalent $C_{1-22}$ hydrocarbon group; and $L_2$ is a single bond, or a group represented by C(=O)N($R^2$)—$R^1$—N($R^3$)* wherein * indicates the bonding position to $L_1$, * indicates the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom, or NR wherein R is a hydrogen atom, an alkyl group or an aralkyl group, and Z is a group represented by formula (a2):

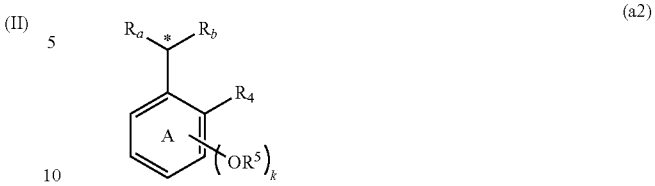

wherein * indicates the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

each $R^5$ in the number of k is independently an organic group having an aliphatic hydrocarbon group having 10 to 40 carbon atoms;

k is an integer of 1 to 4;

ring A optionally further has, in addition to $OR^5$ in the number of k, one or more substituents selected from the group consisting of a halogen atom, a $C_{1-6}$ alkyl group optionally substituted by a halogen atom, and a $C_{1-6}$ alkoxy group optionally substituted by halogen atom;

$R_a$ is a hydrogen atom; and $R_b$ is a hydrogen atom, or a group represented by formula (a3):

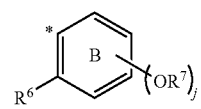

wherein * indicates a bonding position;

j is an integer of 0 to 4;

each $R^7$ in the number of j is independently an organic group having an aliphatic hydrocarbon group having 10 to 40 carbon atoms;

$R^6$ is a hydrogen atom, or optionally a single bond or —O— in combination with $R^4$ to form a fluorenyl group or a xanthenyl group together with ring A; and ring B optionally further has, in addition to OR' in the number of j, one or more substituents selected from the group consisting of a halogen atom, a $C_{1-6}$ alkyl group optionally substituted by a halogen atom, and a $C_{1-6}$ alkoxy group optionally substituted by halogen atom.

18. The nucleotide according to claim 17, wherein m is 0.

19. A nucleotide according to claim 17, wherein
L in formula (II) is a succinyl group, and
$R^5$ and/or $R^7$ are/is an alkyl group having 10 to 40 carbon atoms.

20. A nucleotide according to claim 17, wherein
L in formula (II) is a succinyl group, and
$R_a$ and $R_b$ are both hydrogen atoms, and
$R^5$ is an alkyl group having 10 to 40 carbon atoms.

21. A nucleotide according to claim 17, wherein
L in formula (II) is a succinyl group, and
$R^5$ and/or $R^7$ are/is an alkyl group having 12 to 30 carbon atoms.

22. A nucleotide according to claim 17, wherein
L in the formula (II) is a succinyl group, and
Y—Z is a group selected from the group consisting of
a 3,4,5-tri(octadecyloxy)benzyloxy group,
a 3,5-di(docosyloxy)benzyloxy group,
a 3,5-di[3',4',5'-tri(octadecyloxy)benzyloxy]benzyloxy group, a 3,4,5-tri[3',4',5'-tri(octadecyloxy)benzyloxy]benzyloxy group,
a 3,4,5-tri(octadecyloxy)benzylamino group,
a 2,4-di(docosyloxy)benzylamino group,
a 3,5-di(docosyloxy)benzylamino group,
a di(4-docosyloxyphenyl)methylamino group,
a 4-methoxy-2-[3',4',5'-tri(octadecyloxy)benzyloxy]benzylamino group,
a 4-methoxy-2-[3',4',5'-tri(octadecyloxy)cyclohexylmethyloxy]benzylamino group,
a 2,4-di(dodecyloxy)benzylamino group,
a phenyl(2,3,4-tri(octadecyloxy)phenyl)methylamino group,
a di[4-(12-docosyloxydodecyloxy)phenyl]methylamino group,
a 3,5-di[3',4',5'-tri(octadecyloxy)benzyloxy]benzylamino group, and
a 3,4,5-tri[3',4',5'-tri(octadecyloxy)benzyloxy]-benzylamino group.

23. A nucleotide according to claim 17, wherein Q is a monomethoxytrityl group or a dimethoxytrityl group.

24. A method of producing a protected precursor of an oligonucleotide, comprising:
reacting, in a non-polar solvent:
(a) an n-mer oligonucleotide, wherein n is an integer of one or more, wherein the n-mer oligonucleotide has a 3'-hydroxyl group protected by a solubilizing protecting group and a 5'-hydroxyl group protected by a temporary protecting group removable under an acidic condition,
(b) an acid, and
(c) at least one kind of cation scavenger selected from the group consisting of a pyrrole derivative and an indole derivative,
to remove said temporary protecting group of said 5'-hydroxyl group, to obtain a reaction mixture;
neutralizing said reaction mixture with an organic base, to obtain a neutralized reaction mixture comprising an n-mer oligonucleotide in which the temporary protecting group at the 5'-hydroxyl group has been removed;
mixing with said neutralized reaction mixture a p-mer oligonucleotide, wherein p is an integer of one or more, wherein the p-mer oligonucleotide has a 3'-hydroxyl group phosphoramidited and a 5'-hydroxyl group protected by a temporary protecting group removable under an acidic condition, such that a phosphite triester group is formed via the 5'-hydroxyl group of the n-mer oligonucleotide and the p-mer oligonucleotide is condensed with said n-mer oligonucleotide in which the temporary protecting group of the 5'-hydroxyl group has been removed to obtain a reaction mixture including a protected precursor of a n+p-mer oligonucleotide; and
mixing an oxidizing agent or a sulfurizing agent with said reaction mixture including the protected precursor to convert the phosphite triester group of said protected precursor to a phosphate triester group or a thiophosphate triester group.

25. A method according to claim 24, wherein p is 1.

26. A method according to claim 24, wherein said temporary protecting group is a dimethoxytrityl group or a monomethoxytrityl group.

27. A method according to claim 24, wherein said non-polar solvent is a solvent selected from the group consisting of a halogenated solvent, an aromatic solvent, an ester solvent, an aliphatic solvent, a non-polar ether solvent, and a mixture thereof.

28. A method according to claim 24, wherein said non-polar solvent is a solvent selected from the group consisting of dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and a mixture thereof.

29. A method according to claim 24, wherein said pyrrole derivative or said indole derivative is at least one member selected from the group consisting of pyrrole, 3-methylpyrrole, 2,4-dimethylpyrrole, indole, 4-methylindole, 5-methylindole, 6-methylindole, 7-methylindole, 5,6-dimethylindole, and 6,7-dimethylindole.

30. A method according to claim 24, wherein said oxidizing agent is iodine, (1S)-(+)-(10-camphorsulfonyl)oxaziridine, tert-butyl hydroperoxide, 2-butanone peroxide, 1,1-dihydroperoxycyclododecane, bis(trimethylsilyl)peroxide, or m-chloroperbenzoic acid.

31. A method according to claim 24, wherein said sulfurizing agent is 3-((N,N-dimethylaminomethylidene)amino)-3H-1,2,4-dithiazole-5-thione, 3H-1,2-benzodithiol-3-one-1,1-dioxide, 3H-1,2-benzodithiol-3-one, phenylacetyl disulfide, tetraethylthiuram disulfide, 3-amino-1,2,4-dithiazole-5-thione, or sulfur.

32. A method according to claim 24, wherein said acid is trifluoroacetic acid, dichloroacetic acid, trifluoromethanesulfonic acid, trichloroacetic acid, methanesulfonic acid, hydrochloric acid, acetic acid, or p-toluenesulfonic acid.

33. A method according to claim 24, wherein said organic base is at least one member selected from the group consisting of pyridine, 2,4,6-trimethylpyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole, and 5-nitrobenzimidazole.

* * * * *